US012679884B2

(12) United States Patent
Gu et al.

(10) Patent No.: US 12,679,884 B2
(45) Date of Patent: Jul. 14, 2026

(54) RED LIGHT-CONTROLLED PROTEIN DIMERIZATION SYSTEMS

(71) Applicant: University of Washington, Seattle, WA (US)

(72) Inventors: Liangcai Gu, Seattle, WA (US); Zhimin Huang, Seattle, WA (US); Xiao Zhang, Seattle, WA (US)

(73) Assignee: UNIVERSITY OF WASHINGTON, Seattle, WA (US)

( * ) Notice: Subject to any disclaimer, the term of this patent is extended or adjusted under 35 U.S.C. 154(b) by 753 days.

(21) Appl. No.: 17/997,582

(22) PCT Filed: Jun. 17, 2021

(86) PCT No.: PCT/US2021/037762
§ 371 (c)(1),
(2) Date: Oct. 31, 2022

(87) PCT Pub. No.: WO2021/257790
PCT Pub. Date: Dec. 23, 2021

(65) Prior Publication Data
US 2023/0167167 A1     Jun. 1, 2023

Related U.S. Application Data

(60) Provisional application No. 63/041,688, filed on Jun. 19, 2020.

(51) Int. Cl.
C07K 16/1267          (2026.01)

(52) U.S. Cl.
CPC ...... C07K 16/1267 (2013.01); C07K 2317/22 (2013.01); C07K 2317/569 (2013.01); C07K 2317/92 (2013.01); C07K 2317/94 (2013.01)

(58) Field of Classification Search
None
See application file for complete search history.

(56) References Cited

FOREIGN PATENT DOCUMENTS

WO          2014014206          1/2014
WO      WO-2023231931 A1 *  12/2023  ............. A61K 38/28

OTHER PUBLICATIONS

Stanton, B. Z.; Chory, E. J.; Crabtree, G. R. Chemically induced proximity in biology and medicine. Science 2018, 359, eaao5902.
Stierl, M.; Stumpf, P.; Udwari, D.; Gueta, R.; Hagedorn, R.; Losi, A.; Gartner, W.; Petereit, L.; Efetova, M.; Schwarzel, M.; Oertner, T. G.; Nagel, G.; Hegemann, P., Light modulation of cellular cAMP by a small bacterial photoactivated adenylyl cyclase, bPAC, of the soil bacterium Beggiatoa. J. Biol. Chem. 2011, 286, 1181-1188.

Strickland, D.; Moffat, K.; Sosnick, T. R., Light-activated DNA binding in a designed allosteric protein. Proc. Natl. Acad. Sci. U. S. A. 2008, 105, 10709-10714.
Takala, H.; Bjorling, A.; Berntsson, O.; Lehtivuori, H.; Niebling, S.; Hoernke, M.; Kosheleva, I.; Henning, R.; Menzel, A.; Ihalainen, J. A.; Westenhoff, S. Signal amplification and transduction in phytochrome photosensors. Nature 2014, 509, 245-248.
Takala et al. "Light-induced Changes in the Dimerization Interface of Bacteriophytochromes". J Biol Chem 290(26):16383-92, (May 2013).
Terpe et al. "Overview of tag protein fusions: from molecular and biochemical fundamentals to commercial systems". Appl Microbiol Biotechnol 60(5):523-33, (Jan. 2003).
Tischer et al. "Illuminating cell signaling with optogenetic tools". Nat Rev Mol Cell Biol15(8):551-8, (Jul. 2014).
Toettcher et al. "Using optogenetics to interrogate the dynamic control of signal transmission by the Ras/Erk module". Cell 155(6):1422-34, (Dec. 2013).
Tyanova et al. "The Perseus computational platform for comprehensive analysis of (prote)omics data". Nat Methods 13(9):731-40, (Jun. 2016).
Van Oers et al. "ZAP-70 is constitutively associated with tyrosine-phosphorylated TCR zeta in murine thymocytes and lymph node T cells". Immunity 1(8):675-85, (Nov. 1994).
Vizcaino et al. "2016 update of the PRIDE database and its related tools". Nucleic Acids Res 44(D1):D447-56, (Nov. 2015).
Wagner, J. R.; Zhang, J. R.; Brunzelle, J. S.; Vierstra, R. D.; Forest, K. T. High resolution structure of Deinococcus bacteriophytochrome yields new insights into phytochrome architecture and evolution. J. Biol. Chem. 2007, 282, 12298-12309.
Wagner et al. Mutational analysis of Deinococcus radiodurans bacteriophytochrome reveals key amino acids necessary for the photochromicity and proton exchange cycle of phytochromes. J. Biol. Chem. 2008, 283, 12212-12226.
Wang, X.; Chen, X. J.; Yang, Y., Spatiotemporal control of gene expression by a light-switchable transgene system. Nat. Methods 2012, 9, 266-U64.
Weiss et al. "Signal transduction by lymphocyte antigen receptors". Cell76(2):263-74, (Jan. 1994).
Weissleder, R. A clearer vision for in vivo imaging. Nat. Biotechnol. 2001, 19, 316-317.
Weissleder, R.; Ntziachristos, V. Shedding light onto live molecular targets. Nat. Med. 2003, 9, 123-128.
Williams et al. "Genetic evidence for differential coupling of Syk family kinases to the T-cell receptor: reconstitution studies in a ZAP-70-deficient Jurkat T-cell line". Mol Cell Biol18(3):1388-99, (Mar. 1998).
Winkler, A.; Heintz, U.; Lindner, R.; Reinstein, J.; Shoeman, R. L.; Schlichting, I. A ternary AppA-PpsR-DNA complex mediates light regulation of photosynthesis-related gene expression. Nat. Struct. Mol. Biol. 2013, 20, 859-867.
Wu, D.; Hu, Q.; Yan, Z.; Chen, W.; Yan, C. Y.; Huang, X.; Zhang, J.; Yang, P. Y.; Deng, H. T.; Wang, J. W.; Deng, X. W.; Shi, Y. G., Structural basis of ultraviolet-B perception by UVR8. Nature 2012, 484, 214-U96.

(Continued)

*Primary Examiner* — Marianne P Allen
(74) *Attorney, Agent, or Firm* — MCDONNELL BOEHNEN HULBERT & BERGHOFF LLP

(57) ABSTRACT

*Deinococcus radiodurans* phytochrome (DrBphP) light form-binding antibodies are disclosed and their use in light-induced dimerization systems.

18 Claims, 18 Drawing Sheets

Specification includes a Sequence Listing.

(56) References Cited

OTHER PUBLICATIONS

Wu, C. Y.; Roybal, K. T.; Puchner, E. M.; Onuffer, J.; Lim, W. A. Remote control of therapeutic T cells through a small molecule-gated chimeric receptor. Science 2015, 350, aab4077.

Xia, Y. Z.; Li, K.; Li, J. J.; Wang, T. Q.; Gu, L. C.; Xun, L. Y. (2019) T5 exonuclease-dependent assembly offers a low-cost method for efficient cloning and site-directed mutagenesis. Nucleic Acids Res. 47, e15.

Yang, X.; Kuk, J.; Moffat, K. Crystal structure of Pseudomonas aeruginosa bacteriophytochrome: Photoconversion and signal transduction. Proc. Natl. Acad. Sci. U. S. A. 2008, 105, 14715-14720.

Yazawa, M.; Sadaghiani, A. M.; Hsueh, B.; Dolmetsch, R. E., Induction of protein-protein interactions in live cells using light. Nat. Biotechnol. 2009, 27, 941-U105.

Yuan, H.; Dragnea, V.; Wu, Q.; Gardner, K. H.; Bauer, C. E., Mutational and structural studies of the PixD BLUF output signal that affects light-regulated interactions with PixE. Biochemistry 2011, 50, 6365-6375.

Zhang et al. "Transduction of bone marrow-derived mesenchymal stem cells by using lentivirus vectors pseudotyped with modified RD114 envelope glycoproteins". J Virol 78(3):1219-29, (Feb. 2004).

Zhang et al. The Microbial Opsin Family of Optogenetic Tools. Cell 2011, 147, 1446-1457.

Zhou, X. X.; Chung, H. K.; Lam, A. J.; Lin, M. Z., Optical control of protein activity by Ffuorescent protein domains. Science 2012, 338, 810-814.

Zoltowski, B. D.; Schwerdtfeger, C.; Widom, J.; Loros, J. J.; Bilwes, A. M.; Dunlap, J. C.; Crane, B. R., Conformational switching in the fungal light sensor vivid. Science 2007, 316, 1054-1057.

Davis, S. J.; Vener, A. V.; Vierstra, R. D., Bacteriophytochromes: Phytochrome-like photoreceptors from nonphotosynthetic eubacteria. Science 1999, 286, 2517-2520.

Kolar et al. "OptoBase: A Web Platform for Molecular Optogenetics". ACS Synth Biol 7(7):1825-1828, (Jul. 2018).

Krogan et al. "Global landscape of protein complexes inthe yeast Saccharomyces cerevisiae". Nature 440 (7084):637-43, (Mar. 2006).

Levskaya, A.; Chevalier, A. A.; Tabor, J. J.; Simpson, Z. B.; Lavery, L. A.; Levy, M.; Davidson, E. A.; Scouras, A.; Ellington, A. D.; Marcotte, E. M.; Voigt, C. A., Engineering Escherichia coli to see light—These smart bacteria photograph a light pattern as a high-definition chemical image. Nature 2005, 438, 441-442.

Levskaya et al. "Spatiotemporal control of cell signalling using a light-switchable protein interaction". Nature 461(7266):997-1001, (Sep. 2009).

Lievens, S.; Lemmens, I.; Tavernier, J. Mammalian two-hybrids come of age. Trends Biochem. Sci. 2009, 34, 579-588.

Lindner, R.; Hartmann, E.; Tarnawski, M.; Winkler, A.; Frey, D.; Reinstein, J.; Meinhart, A.; Schlichting, I., Photoactivation mechanism of a bacterial light-regulated adenylyl cyclase. J. Mol. Biol. 2017, 429, 1336-1351.

Lork et al. "Ubiquitination and phosphorylation of the CARD11-BCL10-MALT1 signalosome in T cells". Cell Immunol. 340:103877, (Dec. 2018).

Losi, A.; Polverini, E.; Quest, B.; Gartner, W., First evidence for phototropin-related blue-light receptors in prokaryotes. Biophys. J. 2002, 82, 2627-2634.

Masuda, S.; Nakatani, Y.; Ren, S. K.; Tanaka, M., Blue light-mediated manipulation of transcription factor activity in vivo. ACS Chem. Biol. 2013, 8, 2649-2653.

Mayer, G.; Heckel, A. Biologically active molecules with a "light switch". Angew. Chem. Int. Ed. Engl. 2006, 45, 4900-4921.

Mizuno, H.; Mal, T. K.; Walchli, M.; Kikuchi, A.; Fukano, T.; Ando, R.; Jeyakanthan, J.; Taka, J.; Shiro, Y.; Ikura, M.; Miyawaki, A., Light-dependent regulation of structural flexibility in a photochromic fluorescent protein. Proc. Natl. Acad. Sci. U. S. A. 2008, 105, 9227-9232.

Moglich, A.; Moffat, K., Structural basis for light-dependent signaling in the dimeric LOV domain of the photosensor YtvA. J. Mol. Biol. 2007, 373, 112-126.

Moglich, A.; Ayers, R. A.; Moffat, K., Design and signaling mechanism of light-regulated histidine kinases. J. Mol. Biol. 2009, 385, 1433-1444.

Motta-Mena, L. B.; Reade, A.; Mallory, M. J.; Glantz, S.; Weiner, O. D.; Lynch, K. W.; Gardner, K. H., An optogenetic gene expression system with rapid activation and deactivation kinetics. Nat. Chem. Biol. 2014, 10, 196-202.

Moutel, S.; Bery, N.; Bernard, V.; Keller, L.; Lemesre, E.; de Marco, A.; Ligat, L.; Rain, J. C.; Favre, G.; Olichon, A.; Perez, F. NaLi-H1: A universal synthetic library of humanized nanobodies providing highly functional antibodies and Intrabodies. eLife 2016, 5, e16228.

Muller et al. "A red/far-red light-responsive bi-stable toggle switch to control gene expression in mammalian cells". Nucleic Acids Res 41(7):e77, (Jan. 2013).

Muyldermans, S. Nanobodies: natural single-domain antibodies. Annu. Rev. Biochem. 2013, 82, 775-797.

Nakasako, M.; Zikihara, K.; Matsuoka, D.; Katsura, H.; Tokutomi, S., Structural basis of the LOV1 dimerization of Arabidopsis phototropins 1 and 2. J. Mol. Biol. 2008, 381, 718-733.

Nash, A. I.; McNulty, R.; Shillito, M. E.; Swartz, T. E.; Bogomolni, R. A.; Luecke, H.; Gardner, K. H., Structural basis of photosensitivity in a bacterial light-oxygen-voltage/helix-turn-helix (LOV-HTH) DNA-binding protein. Proc. Natl. Acad. Sci. U. S. A. 2011, 108, 9449-9454.

Nelson, D. C.; Lasswell, J.; Rogg, L. E.; Cohen, M. A.; Bartel, B., FKF1, a clock-controlled gene that regulates the transition to flowering in Arabidopsis. Cell 2000, 101, 331-340.

Niu, J.; Ben Johny, M.; Dick, I. E.; Inoue, T. Following optogenetic dimerizers and quantitative prospects. Biophys. J. 2016, 111, 1132-1140.

Okajima, K.; Yoshihara, S.; Fukushima, Y.; Geng, X. X.; Katayama, M.; Higashi, S.; Watanabe, M.; Sato, S.; Tabata, S.; Shibata, Y.; Itoh, S.; Ikeuchi, M., Biochemical and functional characterization of BLUF-type flavin-binding proteins of two species of cyanobacteria. J. Biochem. 2005, 137, 741-750.

Ong, N. T.; Olson, E. J.; Tabor, J. J. Engineering an E. coli near-infrared light sensor. ACS Synth. Biol. 2018, 7, 240-248.

Pardo et al. "Assignment of protein interactions from affinity purification/mass spectrometry data". J Proteome Res 11(3):1462-74, (Mar. 2012).

Parks et al. "Release of proteins and peptides from fusion proteins using a recombinant plant virus proteinase". Anal Biochem 216(2):413-7, (Feb. 1994).

Piechura et al. "SILAC for the study of mammalian cell lines and yeast protein complexes". Methods Mol Biol 893:201-21, (2012).

Pina et al. "Challenges and opportunities in the purification of recombinant tagged proteins". Biotechnol Adv 32(2):366-81, (Mar.-Apr. 2014).

Qian et al. "Dominant-negative zeta-associated protein 70 inhibits T cell antigen receptor signaling". J Exp Med. 183(2): 611-620, (Feb. 1996).

Ramakrishnan, P.; Tabor, J. J., Repurposing synechocystis PCC6803 UirS-UirR as a UV-violet/green photoreversible transcriptional regulatory tool in E. coli. ACS Synth. Biol. 2016, 5, 733-740.

Redchuk, T. A.; Omelina, E. S.; Chernov, K. G.; Verkhusha, V. V. Near-infrared optogenetic pair for protein regulation and spectral multiplexing. Nat. Chem. Biol. 2017, 13, 633-639.

Redchuk, T. A.; Karasev, M. M.; Verkhusha, P. V.; Donnelly, S. K.; Hulsemann, M.; Virtanen, J.; Moore, H. M.; Vartiainen, M. K.; Hodgson, L.; Verkhusha, V. V. (2020) Optogenetic regulation of endogenous proteins. Nat. Commun. 11, 605.

Reimann et al. "Myofibrillar Z-discs Are a Protein Phosphorylation Hot Spot with Protein Kinase C (PKCα) Modulating Protein Dynamics". Mol Cell Proteomics 16(3):346-367, (Dec. 2016).

Reis, J. M.; Xu, X. L.; McDonald, S.; Woloschuk, R. M.; Jaikaran, A. S. I.; Vizeacoumar, F. S.; Woolley, G. A.; Uppalapati, M. Discovering selective binders for photoswitchable proteins using phage display. ACS Synth. Biol. 2018, 7, 2355-2364.

Reiser et al. "Transduction of nondividing cells using pseudotyped defective high-titer HIV type 1 particles". Proc Natl Acad Sci U S A. 93(26): 15266-15271, (Dec. 1996).

(56)         References Cited

OTHER PUBLICATIONS

Rigaut et al. "A Generic Protein Purification Method for Protein Complex Characterization and Proteome Exploration". Nature Biotech. 17(10):1030-2, (Nov. 1999).

Rockwell, N. C.; Su, Y. S.; Lagarias, J. C. Phytochrome structure and signaling mechanisms. Annu. Rev. Plant Biol. 2006, 57, 837-858.

Roncagalli et al. "Quantitative proteomics analysis of signalosome dynamics in primary T cells identifies the surface receptor CD6 as a Lat adaptor-independent TCR signaling hub". Nat Immunol. 15(4):384-392, (Mar. 2014).

Roose et al. "T cell receptor-independent basal signaling via Erk and Abl kinases suppresses RAG gene expression" PLoS Biol 1(2):E53, (Nov. 2003).

Ryu, M. H.; Moskvin, O. V.; Siltberg-Liberles, J.; Gomelsky, M., Natural and engineered photoactivated nucleotidyl cyclases for optogenetic applications. J. Biol. Chem. 2010, 285, 41501-41508.

Salomon, M.; Christie, J. M.; Knieb, E.; Lempert, U.; Briggs, W. R., Photochemical and mutational analysis of the FMN-binding domains of the plant blue light receptor, phototropin. Biochemistry 2000, 39, 9401-9410.

Schamel et al. "Organization of the resting TCR in nanoscale oligomers". Immunol Rev251(1):13-20, (Jan. 2013).

Scheib, U.; Stehfest, K.; Gee, C. E.; Korschen, H. G.; Fudim, R.; Oertner, T. G.; Hegemann, P., The rhodopsin-guanylyl cyclase of the aquatic fungus Blastocladiella emersonii enables fast optical control of cGMP signaling. Sci. Signal. 2015, 8.

Scheuermann, T. H.; Brautigam, C. A. (2015) High-precision, automated integration of multiple isothermal titration calorimetric thermograms: New features of NITPIC. Methods 76, 87-98.

Skrlec, K.; Strukelj, B.; Berlec, A. Non-immunoglobulin scaffolds: a focus on their targets. Trends Biotechnol. 2015, 33, 408-418.

Sharrock, R. A.; Quail, P. H., Novel phytochrome sequences in *Arabidopsis thaliana*: structure, evolution, and differential expression of a plant regulatory photoreceptor family. Genes Dev. 1989, 3, 1745-1757.

Shimizu-Sato, S.; Huq, E.; Tepperman, J. M.; Quail, P. H. A light-switchable gene promoter system. Nat. Biotechnol. 2002, 20, 1041-1044.

Shu, X. K.; Royant, A.; Lin, M. Z.; Aguilera, T. A.; Lev-Ram, V.; Steinbach, P. A.; Tsien, R. Y., Mammalian expression of infrared fluorescent proteins engineered from a bacterial phytochrome. Science 2009, 324, 804-807.

Smith et al. "Unearthing the transition rates between photoreceptor conformers". BMC Syst Biol 10(1):110, (Nov. 2016).

Song, J. Y.; Cho, H. S.; Cho, J. I.; Jeon, J. S.; Lagarias, J. C.; Park, Y. I., Near-UV cyanobacteriochrome signaling system elicits negative phototaxis in the cyanobacterium *Synechocystis* sp PCC 6803. Proc. Natl. Acad. Sci. U. S. A. 2011, 108, 10780-10785.

Spencer, D. M.; Wandless, T. J.; Schreiber, S. L.; Crabtree, G. R. Controlling signal transduction with synthetic ligands. Science 1993, 262, 1019-1024.

Abe, K.; Miyake, K.; Nakamura, M.; Kojima, K.; Ferri, S.; Ikebukuro, K.; Sode, K., Engineering of a green-light inducible gene expression system in *Synechocystis* sp PCC6803. Microb. Biotechnol. 2014, 7, 177-183.

Adrian et al. "A Phytochrome-Derived Photoswitch for Intracellular Transport". ACS Synth Biol 6(7):1248-1256, (Mar. 2017).

Ali, A. M.; Reis, J. M.; Xia, Y.; Rashid, A. J.; Mercaldo, V.; Walters, B. J.; Brechun, K. E.; Borisenko, V.; Josselyn, S. A.; Karanicolas, J.; Woolley, G. A., Optogenetic inhibitor of the transcription factor CREB. Chem. Biol. 2015, 22, 1531-1539.

Au-Yeung et al. "The structure, regulation, and function of ZAP-70". Immunol Rev. 228(1):41-57, (Mar. 2009).

Baca, M.; Borgstahl, G. E. O.; Boissinot, M.; Burke, P. M.; Williams, D. R.; Slater, K. A.; Getzoff, E. D., Complete chemical structure of photoactive yellow protein: novel thioester-linked 4-hydroxycinnamyl chromophore and photocycle chemistry. Biochemistry 1994, 33, 14369-14377.

Balagopalan et al. "The Linker for Activation of T Cells (LAT) Signaling Hub: From Signaling Complexes to Microclusters". J Biol Chem. 290(44): 26422-26429, (Sep. 2015).

Bellini, D.; Papiz, M. Z. Structure of a bacteriophytochrome and light-stimulated protomer swapping with a gene repressor. Structure 2012, 20, 1436-1446.

Beyer et al. "Red Light-Regulated Reversible Nuclear Localization of Proteins in Mammalian Cells and Zebrafish". ACS Synth Biol 4(9):951-8, (Mar. 2015).

Beyer et al. "Generic and reversible opto-trapping of biomolecules". Acta Biomater 79:276-282, (Aug. 2018).

Bhoo, S. H.; Davis, S. J.; Walker, J.; Karniol, B.; Vierstra, R. D. Bacteriophytochromes are photochromic histidine kinases using a biliverdin chromophore. Nature 2001, 414, 776-779.

Blain-Hartung, M.; Rockwell, N. C.; Moreno, M. V.; Martin, S. S.; Gan, F.; Bryant, D. A.; Lagarias, J. C., Cyanobacteriochrome-based photoswitchable adenylyl cyclases (cPACs) for broad spectrum light regulation of cAMP levels in cells. J. Biol. Chem. 2018, 293, 8473-8483.

Burgie, E. S.; Bussell, A. N.; Walker, J. M.; Dubiel, K.; Vierstra, R. D., Crystal structure of the photosensing module from a red/far-red light-absorbing plant phytochrome. Proc. Natl. Acad. Sci. U. S. A. 2014, 111, 10179-10184.

Chan et al. "ZAP-70: a 70 kd protein-tyrosine kinase that associates with the TCR zeta chain". Cell 71(4):649-62, (Nov. 1992).

Chen, D.; Gibson, E. S.; Kennedy, M. J., A light-triggered protein secretion system. J. Cell Biol. 2013, 201, 631-640.

Chernov, K. G.; Redchuk, T. A.; Omelina, E. S.; Verkhushaa, V. V. Near-infrared fluorescent proteins, biosensors, and optogenetic tools engineered from phytochromes. Chem. Rev. 2017, 117, 6423-6446.

Chevalier et al. Massively parallel de novo protein design for targeted therapeutics. Nature 2017, 550, 74-79.

Christie, J. M.; Salomon, M.; Nozue, K.; Wada, M.; Briggs, W. R. LOV (light, oxygen, or voltage) domains of the blue-light photoreceptor phototropin (nph1): Binding sites for the chromophore flavin mononucleotide. Proc. Natl. Acad. Sci. U. S. A. 1999, 96, 8779-8783.

Choi et al. "Maximizing binary interactome mapping with a minimal number of assays". Nat. Commun. 2019, 10, 3907.

Cox et al. "MaxQuant enables high peptide identification rates, individualized p.p.b.-range mass accuracies and proteome-wide protein quantification". Nat Biotechnol 26(12):1367-72, (Nov. 2008).

Cox et al. "Andromeda: a peptide search engine integrated into the MaxQuant environment". J Proteome Res 10(4):1794-805, (Feb. 2011).

Cox et al. "Accurate Proteome-wide Label-free Quantification by Delayed Normalization and Maximal Peptide Ratio Extraction, Termed MaxLFQ*". Mol Cell Proteomics. 13(9): 2513-2526, (Jun. 2014).

Essen, L. O.; Mailliet, J.; Hughes, J., The structure of a complete phytochrome sensory module in the Pr ground state. Proc. Natl. Acad. Sci. U. S. A. 2008, 105, 14709-14714.

Gibson et al. "Enzymatic assembly of DNA molecules up to several hundred kilobases". Nat Methods 6(5):343-5, (Apr. 2009).

Gingras et al. "Analysis of protein complexes using mass spectrometry". Nat Rev Mol Cell Biol 8(8):645-54, (Aug. 2007).

Guntas, G.; Hallett, R. A.; Zimmerman, S. P.; Williams, T.; Yumerefendi, H.; Bear, J. E.; Kuhlman, B. Engineering an improved light-induced dimer (iLID) for controlling the localization and activity of signaling proteins. Proc. Natl. Acad. Sci. U. S. A. 2015, 112, 112-117.

Guo, H. W.; Yang, W. Y.; Mockler, T. C.; Lin, C. T., Regulations of flowering time by *Arabidopsis* photoreceptors. Science 1998, 279, 1360-1363.

Halavaty, A. S.; Moffat, K., N- and C-terminal flanking regions modulate light-induced signal transduction in the LOV2 domain of the blue light sensor phototropin 1 from Avena sativa. Biochemistry 2007, 46, 14001-14009.

Heintzen, C.; Loros, J. J.; Dunlap, J. C., The PAS protein VIVID defines a clock-associated feedback loop that represses light input, modulates gating, and regulates clock resetting. Cell 2001, 104, 453-464.

Hirose, Y.; Shimada, T.; Narikawa, R.; Katayama, M.; Ikeuchi, M., Cyanobacteriochrome CcaS is the green light receptor that induces

(56) References Cited

OTHER PUBLICATIONS the expression of phycobilisome linker protein. Proc. Natl. Acad. Sci. U. S. A. 2008, 105, 9528-9533.

Horner et al. "Light-Controlled Affinity Purification of Protein Complexes Exemplified by the Resting ZAP70 Interactome". Front Immunol 10:226, (Feb. 2019).

Huang, Z. L.; Wu, Y. Q.; Allen, M. E.; Pan, Y. J.; Kyriakakis, P.; Lu, S. Y.; Chang, Y. J.; Wang, X.; Chien, S.; Wang, Y. X. Engineering light-controllable CAR T cells for cancer immunotherapy. Sci. Adv. 2020, 6, eaay920.

Huang et al. "Creating Red Light-Switchable Protein Dimerization Systems as Genetically Encoded Actuators with High Specificity". ACS Synth Biol 9(12):3322-3333, (Nov. 2020).

Hughes, J.; Lamparter, T.; Mittmann, F.; Hartmann, E.; Gartner, W.; Wilde, A.; Borner, T., A prokaryotic phytochrome. Nature 1997, 386, 663-663.

Huttlin et al. "Architecture of the human interactome defines protein communities and disease networks". Nature 545(7655):505-509, (May 2017).

Iwashima et al. "Sequential interactions of the TCR with two distinct cytoplasmic tyrosine kinases". Science 263 (5150):1136-9, (Feb. 1994).

Jobsis, F. F. Noninvasive, infrared monitoring of cerebral and myocardial oxygen sufficiency and circulatory parameters. Science 1977, 198, 1264-1267.

Kabemiuk, A. A.; Shemetov, A. A.; Verkhusha, V. V. A bacterial phytochrome-based optogenetic system controllable with near-infrared light. Nat. Methods 2016, 13, 591-597.

Kainrath, S.; Stadler, M.; Reichhart, E.; Distel, M.; Janovjak, H., Green-light-induced inactivation of receptor signaling using cobalamin-binding domains. Angew. Chem. Int. Ed. Engl. 2017, 56, 4608-4611.

Kang, S.; Davidsen, K.; Gomez-Castillo, L.; Jiang, H.; Fu, X.; Li, Z.; Liang, Y.; Jahn, M.; Moussa, M.; DiMaio, F.; Gu, L. COMBINES-CID: An efficient method for de novo engineering of highly specific chemically induced protein dimerization systems. J. Am. Chem. Soc. 2019, 141, 10948-10952.

Katz et al. "A cycle of Zap70 kinase activation and release from the TCR amplifies and disperses antigenic stimuli". Nat Immunol. 18(1):86-95, (Nov. 2016).

Keefe et al. "One-step purification of recombinant proteins using a nanomolar-affinity streptavidin-binding peptide, the SBP-Tag". Protein Expr Purif23(3):440-6, (Dec. 2001).

Kennedy, M. J.; Hughes, R. M.; Peteya, L. A.; Schwartz, J. W.; Ehlers, M. D.; Tucker, C. L. Rapid blue-light-mediated induction of protein interactions in living cells. Nat. Methods 2010, 7, 973-975.

Khanna et al. "A novel molecular recognition motif necessary for targeting photoactivated phytochrome signaling to specific basic helix-loop-helix transcription factors". Plant Cell. 16(11):3033-44, (Oct. 2004).

Kim et al. "Epitope mapping of monoclonal antibodies for the Deinococcus radiodurans bacteriophytochome". Protein Sci 23(6):812-8, (Apr. 2014).

Klemm, J. D.; Schreiber, S. L.; Crabtree, G. R. Dimerization as a regulatory mechanism in signal transduction. Annu. Rev. Immunol. 1998, 16, 569-592.

Klewer, L.; Wu, Y. W. Light-induced dimerization approaches to control cellular processes. Chem.: Eur. J. 2019, 25, 12452-12463.

Kliebenstein, D. J.; Lim, J. E.; Landry, L. G.; Last, R. L., *Arabidopsis* UVR8 regulates ultraviolet-B signal transduction and tolerance and contains sequence similarity to human Regulator of Chromatin Condensation 1. Plant Physiol. 2002, 130, 234-243.

Knop et al. "Epitope tagging of yeast genes using a PCR-based strategy: more tags and improved practical routines". Yeast 15(10B):963-72, (Jul. 1999).

Kojadinovic, M.; Laugraud, A.; Vuillet, L.; Fardoux, J.; Hannibal, L.; Adriano, J. M.; Bouyer, P.; Giraud, E.; Vermeglio, A. Dual role for a bacteriophytochrome in the bioenergetic control of Rhodopsdeudomonas palustris: Enhancement of photosystem synthesis and limitation of respiration. Biochim. Biophys. Acta 2008, 1777, 163-172.

Kolar, K.; Weber, W. Synthetic biological approaches to optogenetically control cell signaling. Curr. Opin. Biotechnol. 2017, 47, 112-119.

* cited by examiner a
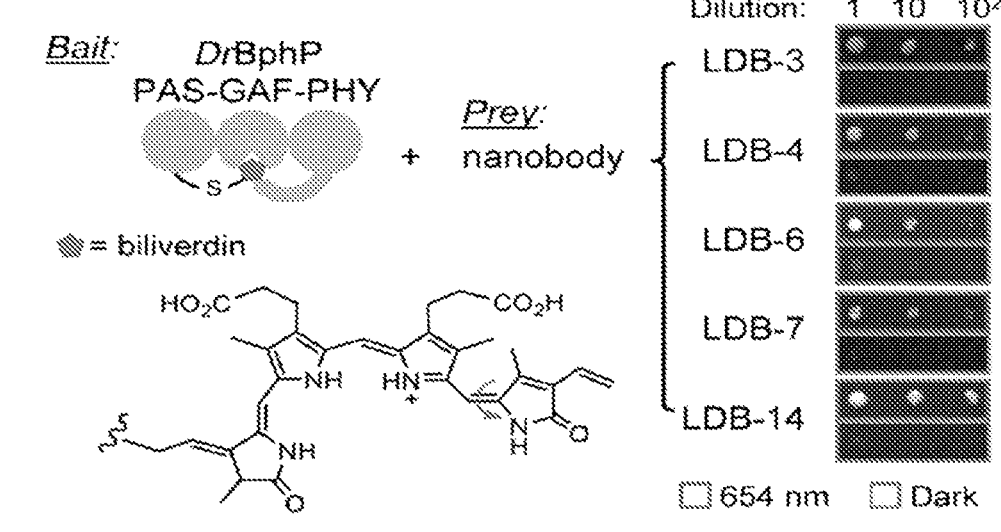
b
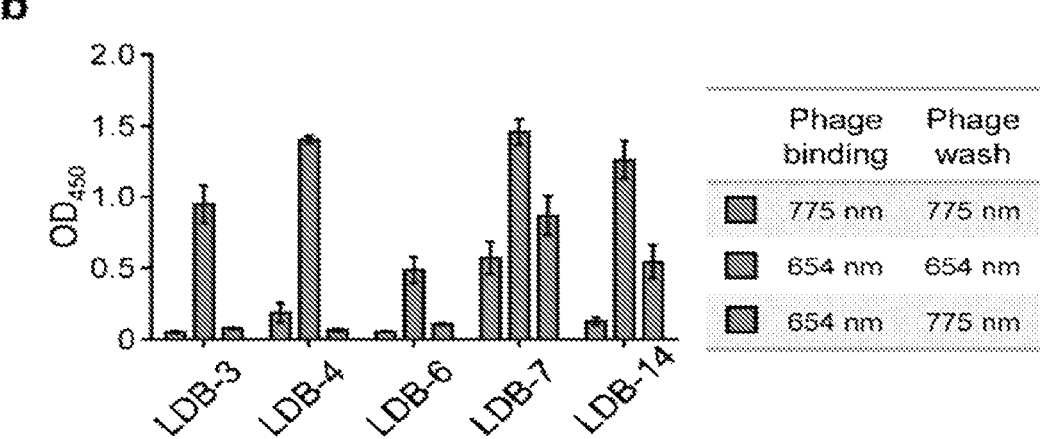
Figure 2 a
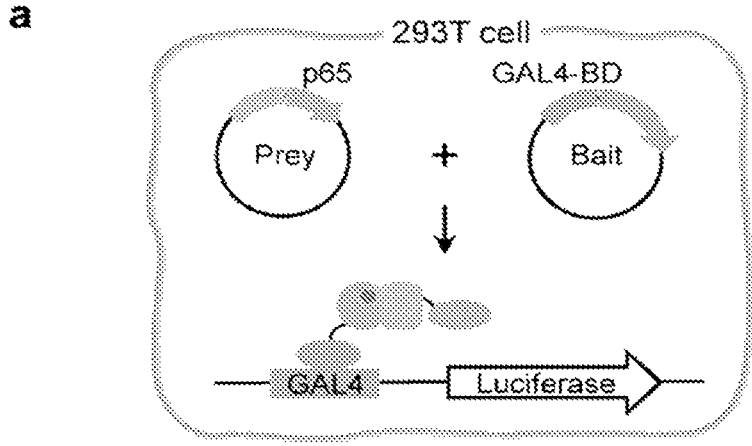
b
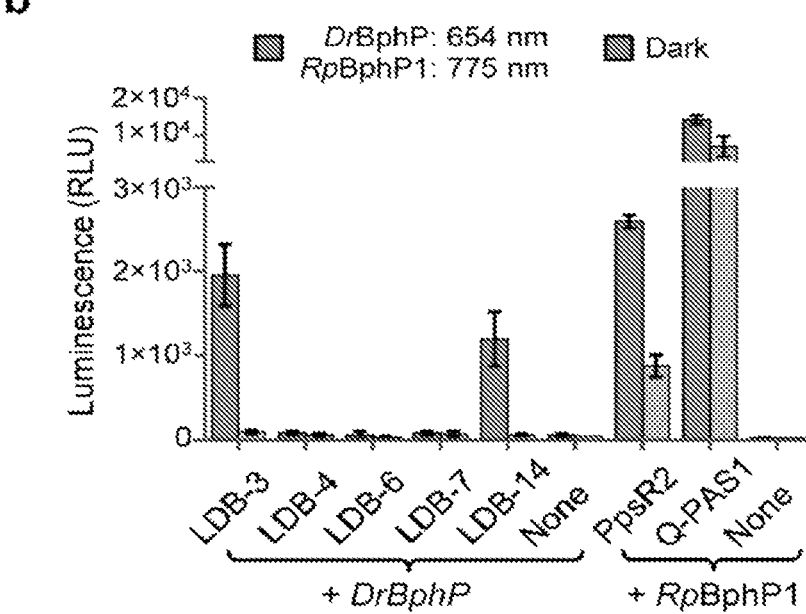
Figure 3 a
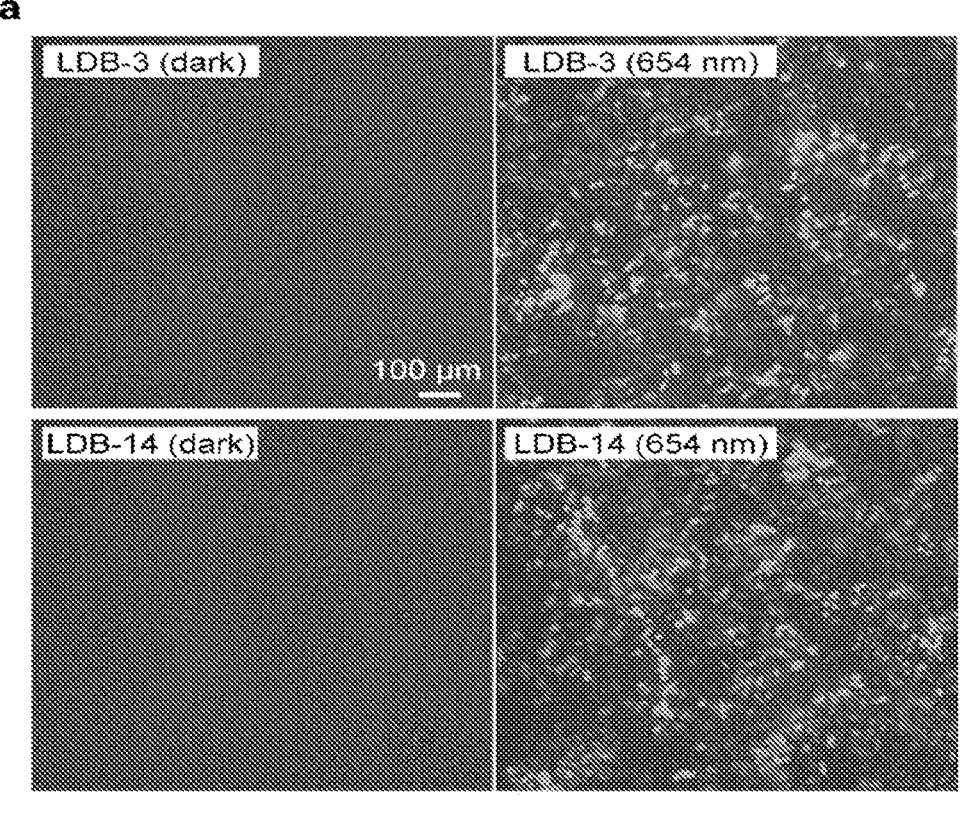
b
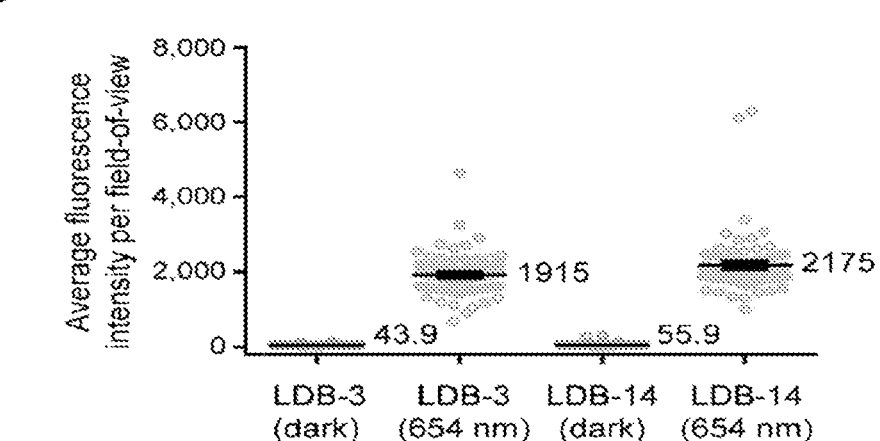
Figure 6 a
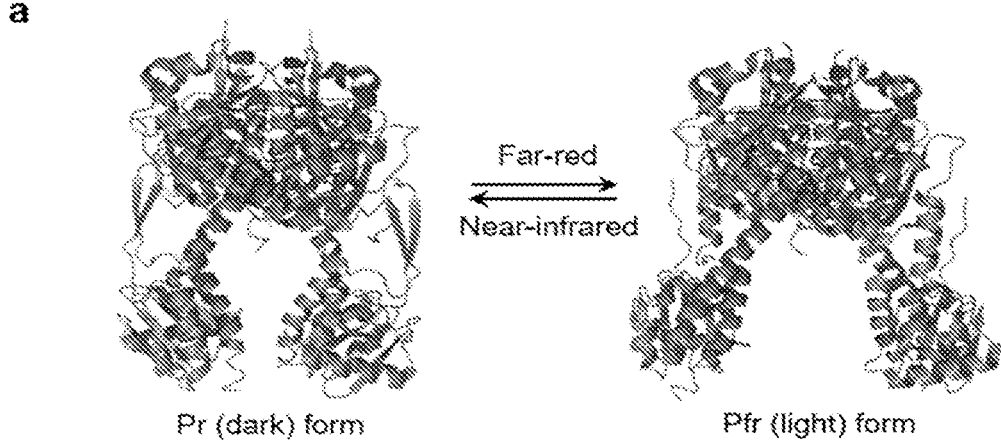
Pr (dark) form                    Pfr (light) form
b
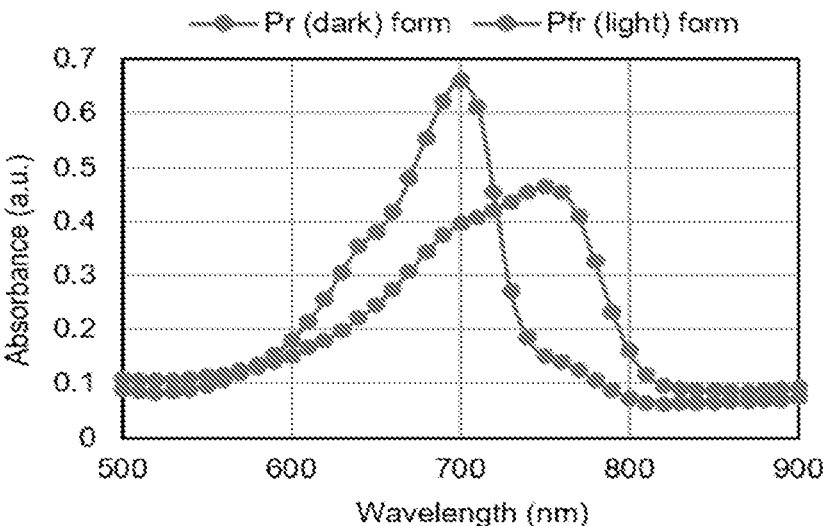
Figure 9 a
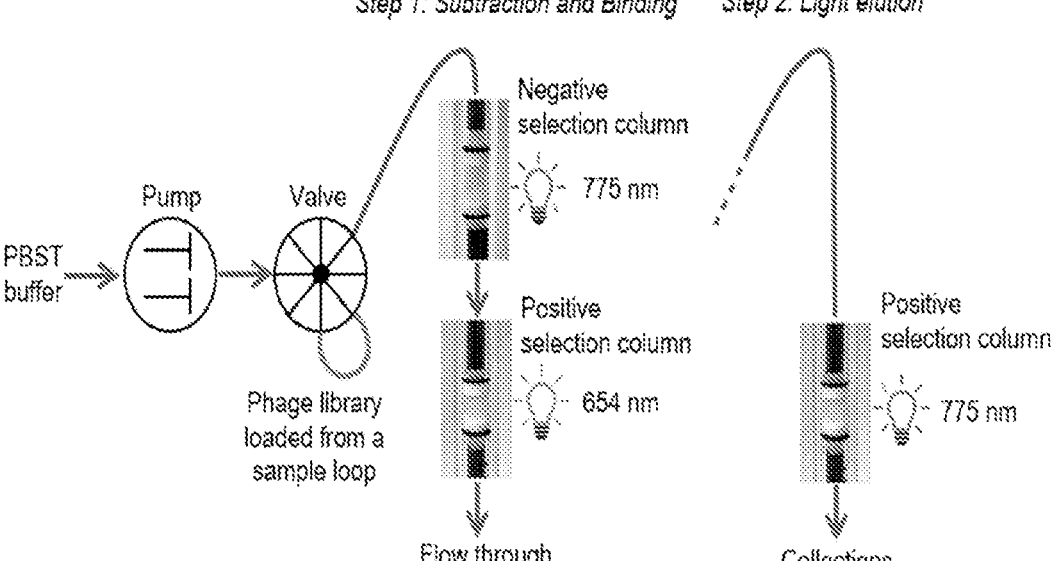
b
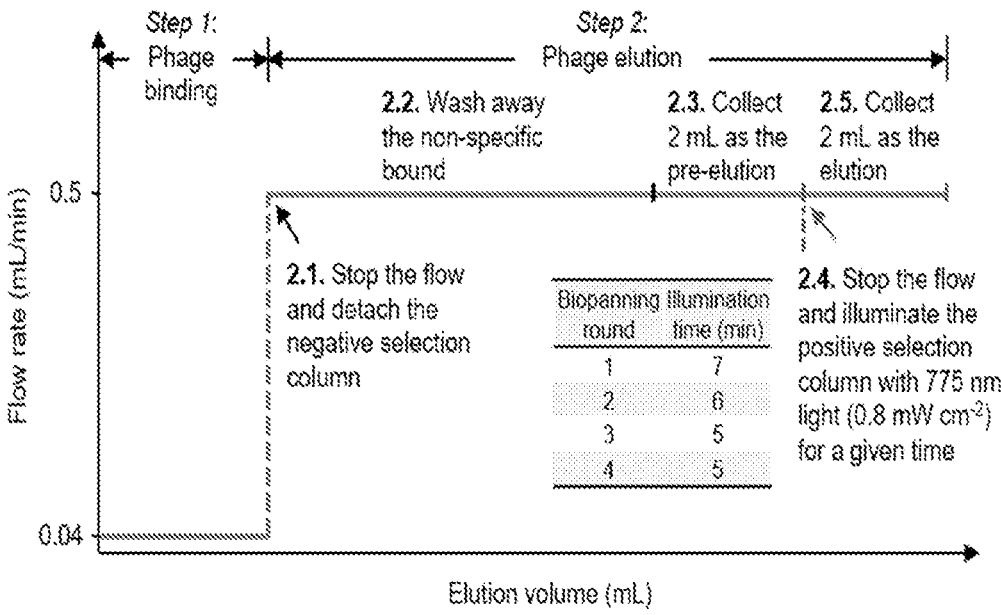
Figure 10

Selected nanobody     *Dr*BphP
sub-library     (PAS-GAF-PHY)

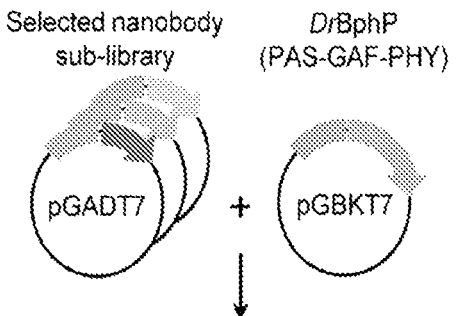

pGADT7    +    pGBKT7

1. Plate and grow co-transformed
   yeast on SD/-Ade/-His/-Leu/-Trp
   plates under a light condition for 4-5
   days;

2. Pick and grow colonies in 1-mL
   SD/-Leu/-Trp medium in 96-well
   plates under the light condition for
   24 h;

3. Replica spot 1 μL cells to SD/–
   Ade/–His/–Leu/–Trp plates, grow
   them under the light and dark
   conditions for 2 to 3 days, and
   select clones significantly growing
   faster under the light condition.

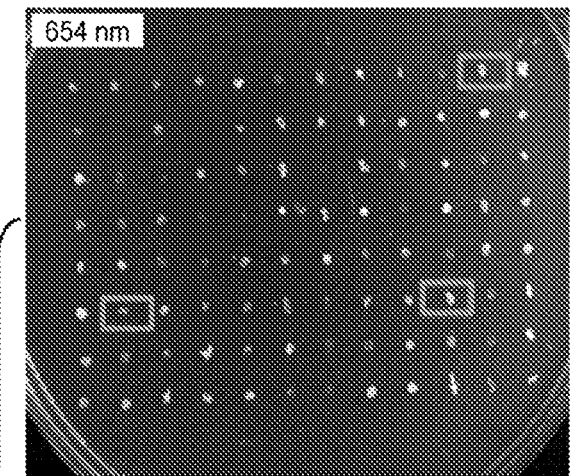

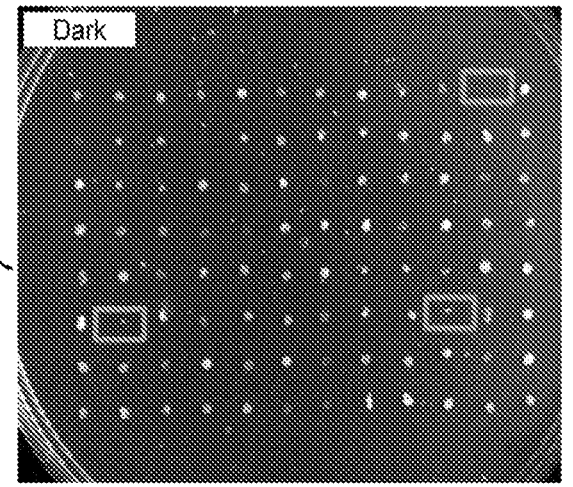

Figure 11

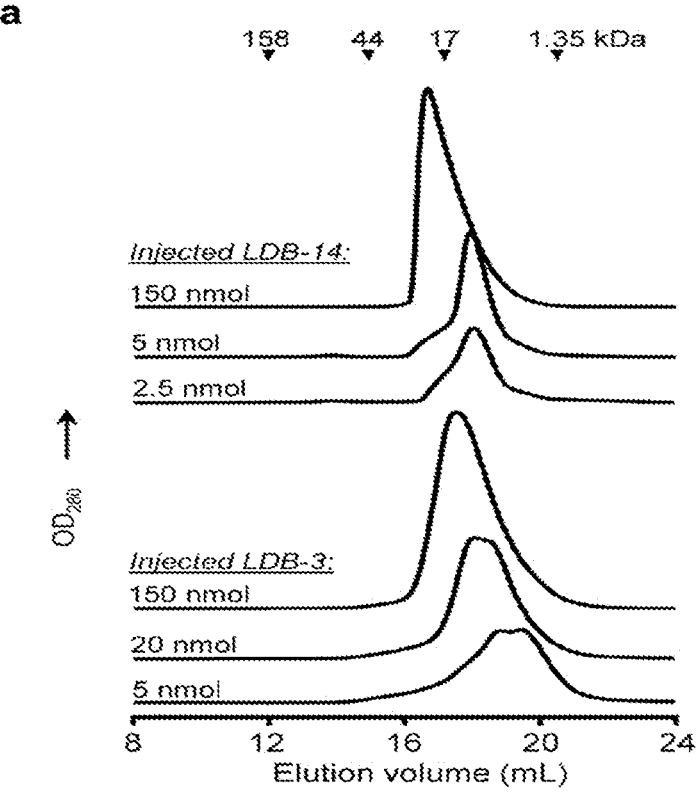
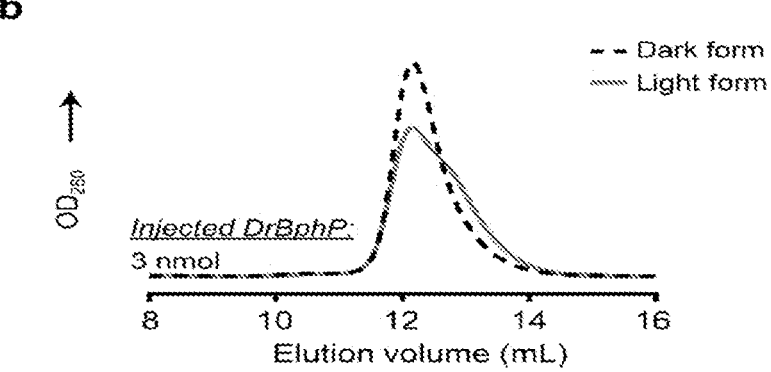
Figure 13

1. Production of a biotinylated conformation switcher (_2-3 weeks_)

2. Phage display selection of a combinatorial binder library to obtain a sub-library of enriched dimerization binders (typically 2 to 4 rounds, _1-2 weeks_)

3. Yeast two-hybrid screening of the sub-library to obtain dimerization binder hits (_3-4 weeks_)

4. Expression and purification of dimerization binder hits (_1-2 week_)

5. _In vitro_ binding specificity validation by ELISA or other methods (_2 days to 1 week_)

6. Functional validation of biosensor candidates by a mammalian two-hybrid assay (_~1 week_)

Test LID biosensors for applications

Figure 18

RED LIGHT-CONTROLLED PROTEIN DIMERIZATION SYSTEMS

CROSS REFERENCE

This application is a U.S. national phase of International Application No. PCT/US2021/037765, filed on Jun. 17, 2021, which claims priority to U.S. Provisional Application Ser. No. 63/041,688, filed Jun. 19, 2020, both of which are incorporated by reference herein in their entirety.

FEDERAL FUNDING STATEMENT

This invention was made with government support under Grant No. R35 GM128918, awarded by the National Institutes of Health. The government has certain rights in the invention.

SEQUENCE LISTING STATEMENT

A computer readable form of the Sequence Listing is filed with this application by electronic submission and is incorporated into this application by reference in its entirety. The Sequence Listing is contained in the file created on Jan. 29, 2026 having the file name "20-946-WO-US_a-mended_2026-01-29.txt" and is 32,424 bytes in size.

BACKGROUND

Protein dimerization systems that can be controlled by red light with increased tissue penetration depth are highly needed tool for clinical applications such as cell and gene therapies. However, existing red light-induced dimerization systems are all based on phytochrome photoreceptors and naturally occurring binding partners with complex structures and suboptimal in vivo performance, limiting mammalian applications.

SUMMARY

In one aspect, the disclosure provides Deinococcus radiodurans bacteriophytochrome (DrBphP) light form-binding antibodies, comprising a set of complementarity-determining regions (CDRs) selected from the group consisting of:
(a) SEQ ID NO:1 (CDR1), SEQ ID NO:2 (CDR2), and SEQ ID NO:3 (CDR3); or
(b) SEQ ID NO:4 (CDR1), SEQ ID NO:5 (CDR2), and SEQ ID NO:6 (CDR3).
In various embodiments, the antibody may be a monoclonal antibody, wherein the antibody is selected from the group consisting of humanized antibody, chimeric antibody, Fab', F(ab')$_2$, Fab, Fv, rIgG, recombinant single chain Fv fragments (scFv), single-domain antibody (nanobody), bivalent or bispecific molecule, diabody, triabody, and tetrabody. In one embodiment, the antibody comprises a single-domain antibody.

In a further embodiment, the antibody comprises an amino acid sequence at least 40%, 45%, 50%, 55%, 60%, 65%, 70%, 75%, 80%, 85%, 90%, 91%, 92%, 93%, 94%, 95%, 96%, 97%, 98%, 99%, or 100% identical along the length of the amino acid sequence of SEQ ID NO: 9 or SEQ ID NO:10.

In further aspects, the disclosure provides nucleic acids encoding the antibodies of the disclosure, expression vectors comprising the nucleic acids operatively linked to a control sequence, cells comprising the antibody, nucleic acid, or expression vector of any preceding claim, and kits comprising:
(a) the antibody, nucleic acid, expression vector, and/or cell of any of preceding claim; and
(b) a photosensory module of Deinococcus radiodurans bacteriophytochrome (DrBphP), including but not limited to a polypeptide at least 70%, 75%, 80%, 85%, 90%, 91%, 92%, 93%, 94%, 95%, 96%, 97%, 98%, 99%, or 100% identical to the amino acid sequence of SEQ ID NO: 11, wherein optional residues in parentheses may be present or absent and are not considered when determining the percent identity when absent, a nucleic acid encoding such a photosensory module of DrBphP, an expression vector comprising the nucleic acid encoding such a photosensory module of DrBphP operatively linked to a control sequence, and/or cell comprising the photosensory module of DrBphP, the nucleic acid encoding the photosensory module of DrBphP, and/or the expression vector comprising the nucleic acid encoding a photosensory module of DrBphP operatively linked to a control sequence.

The disclosure further provides methods for use of the antibodies, kits, nucleic acids, expression vectors, or host cell of any embodiment or combination of embodiments disclosed herein for any suitable purpose, including but not limited to use as a light induced dimerization (LID) system for any purpose, including but not limited to control light activated gene expression and spatiotemporal activation of chimeric antigen receptor T (CAR-T) cells, etc.

In another aspect, the disclosure provides methods for making a light induced dimerization (LID) system, comprising
(a) phage display to enrich binders that only bind to the light form of a conformation switcher (i.e.: changes conformation when exposed to light); and
(b) yeast two-hybrid (Y2H) screening of the enriched sub-library to select for in vivo LID activity. In one embodiment, the method comprises
(a) screening a synthetic combinatorial polypeptide library with a light form of a conformation switcher to identify binding polypeptides; and
(b) screening a synthetic combinatorial polypeptide library with a dark form of a conformation switcher (conformation assumed when not exposed to light) to identify dimerization polypeptides in the library that (i) bind to the light form of a conformation switcher, and (ii) do not bind to the dark form of a conformation switcher.

DESCRIPTION OF THE FIGURES

FIG. 2($a$-$b$). Y2H and single phage ELISA analyses of dimerization binder candidates. (a) Y2H assay with the biliverdin-bound DrBphP photosensory module as a bait and nanobodies as preys. A serial dilution of Y2HGold cells resuspended in 0.9% NaCl were spotted on SD/-Ade/-His/-Leu/-Trp plates and grown under the 654-nm illumination (0.03 mW/cm$^2$) or in the dark. A representative result from three independent experiments is shown on the right. (b) ELISA analysis of nanobody binding specificity and reversibility. Phage-displayed nanobodies were bound to DrBphP immobilized in microtiter plates, which were illuminated with the 654-nm (0.3 mW/cm$^2$) or 775-nm (0.2 mW/cm$^2$)

lights during the binding and wash steps. Data represent mean values of 3 measurements; error bars, standard deviation.

FIG. 3(*a-b*). Nanobody specificity validation in mammalian cells. (a) Schematic of the M2H assay. DrBphP and nanobody genes were inserted into the bait and prey plasmids, respectively. (b) Specificity comparison of LID systems. HEK293T cells were transiently co-transfected with the bait, prey, and GAL4UAS-luciferase reporter plasmids (~0.25 µg each) in a 0.5 mL culture. None, the negative control transfected with only the bait and the luciferase reporter plasmids. Cells were cultured under the illumination (654-nm (0.2 mW/cm$^2$) or 775-nm (0.2 mW/cm$^2$)) or in the dark for 24 hours before measuring luciferase levels. Different from DrBphP, RpBphP1 is required to be converted to the light form by a NIR (e.g., 775-nm) light. Data represent mean values of 3 measurements; error bars, standard deviation.

Figure 4:
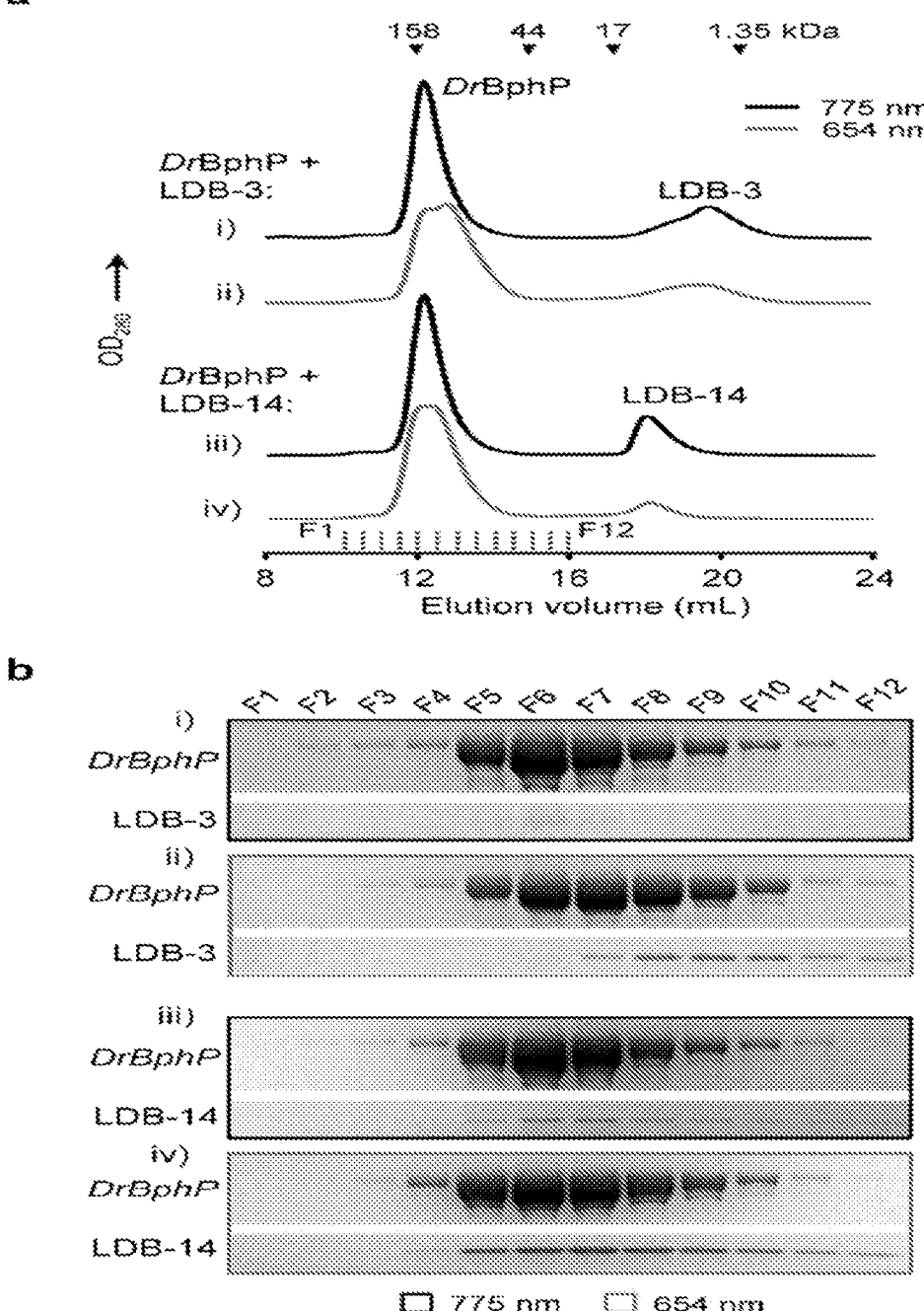

FIG. 4(*a-b*). Detection of light-induced DrBphP-nanobody complexes (a) Analytical SEC. ~6 µM (final concentration) DrBphP after the 654-nm (0.2 mW/cm$^2$) or 775-nm (0.8 mW/cm$^2$) illumination for 5 min were incubated with ~5 µM (final concentration) LDB-3 or LDB-14 in the dark. 500 µL mixtures were loaded onto a Superdex™ 200 Increase 10/300 GL column pre-equilibrated with 1×PBS buffer and eluted at 0.75 mL/min at 4° C. Elution volumes of protein standards are marked by triangles. Fractions (500 µL each; marked by dash lines) were collected and concentrated by trichloroacetic acid precipitation for SDS-PAGE analysis (b). Only gel regions showing DrBphP and nanobody bands are shown.

Figure 5:
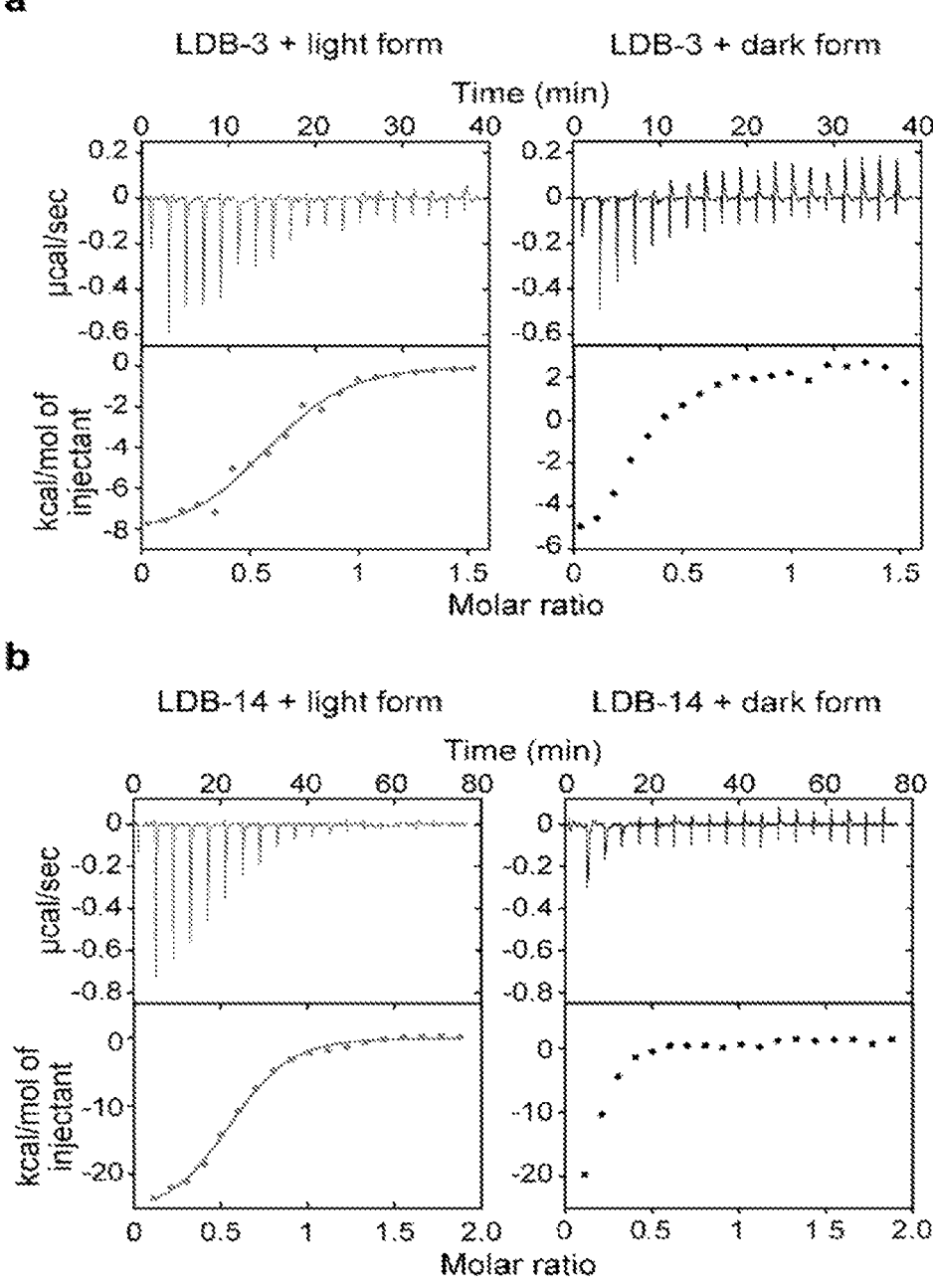

FIG. 5(*a-b*). ITC thermographs of the nanobody binding. 80 µM LDB-3 (a) and 50 µM LDB-14 (b) were titrated into 10 µM and 5 µM DrBphP, respectively. The light and dark forms were converted by the 654-nm (0.2 mW/cm$^2$) and 775-nm (0.2 mW/cm$^2$) lights, respectively. The raw data (top) and the integration of heats (bottom) for each titration are shown.

FIG. 6(*a-b*). Red light-induced expression of GFP. (a) Representative overlaid brightfield and fluorescence images of GFP-expressing HEK293T cells. Cells were transduced with a lentiviral GFP expression vector and then co-transfected with the LID plasmids after 654-nm (0.2 mW/cm$^2$) illumination or in the dark for 48 hours. (b) Comparison of GFP fluorescence intensities in fields-of-view (FOVs). Data represent mean values of 78 FOVs; error bars, standard error of the mean (SEM).

Figure 7:
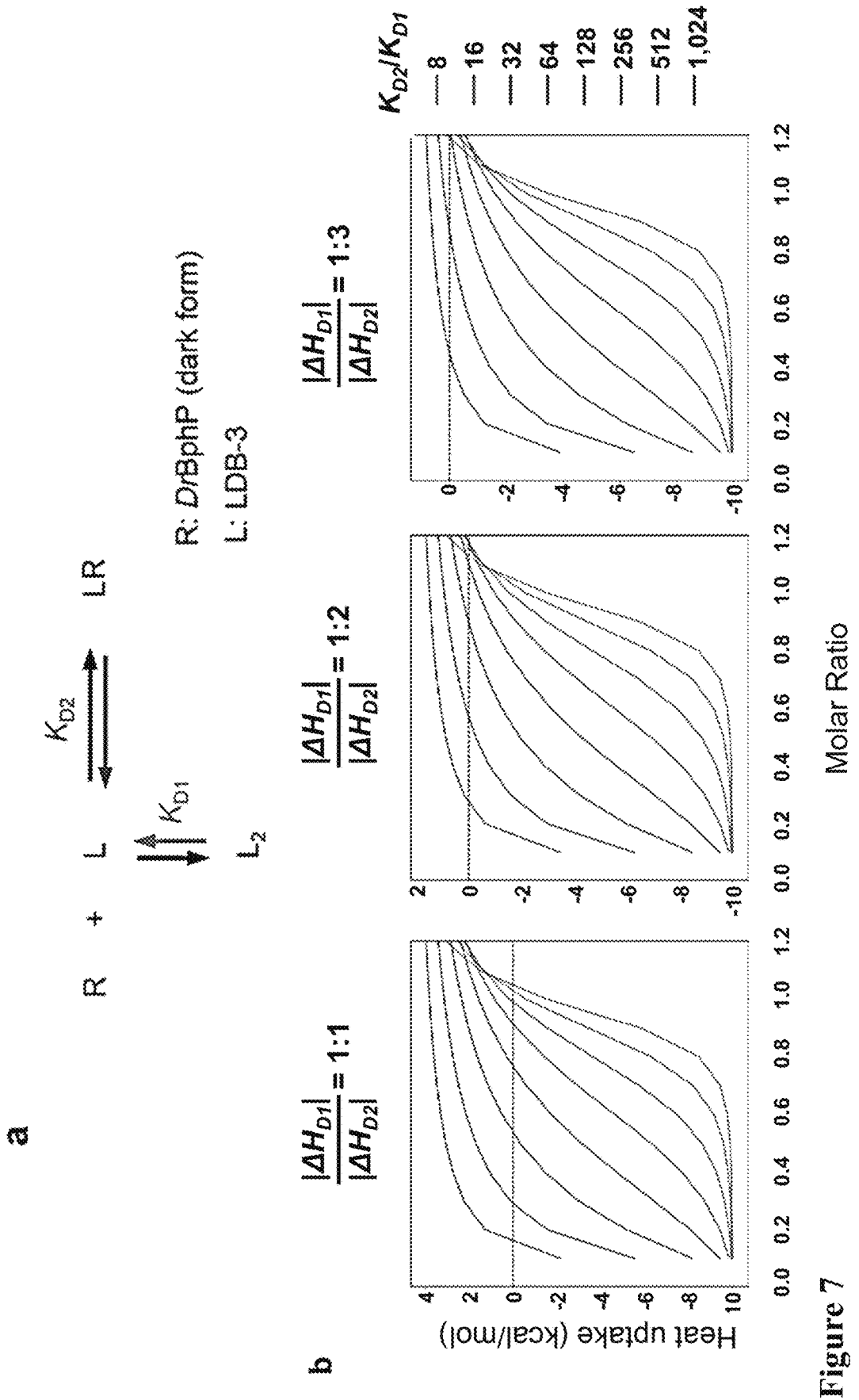

FIG. 7. (a) Two-state equilibrium model used in the thermodynamic simulation. (b) Thermographs showing the integration of heat transfer in simulated titration experiments.

Figure 8:
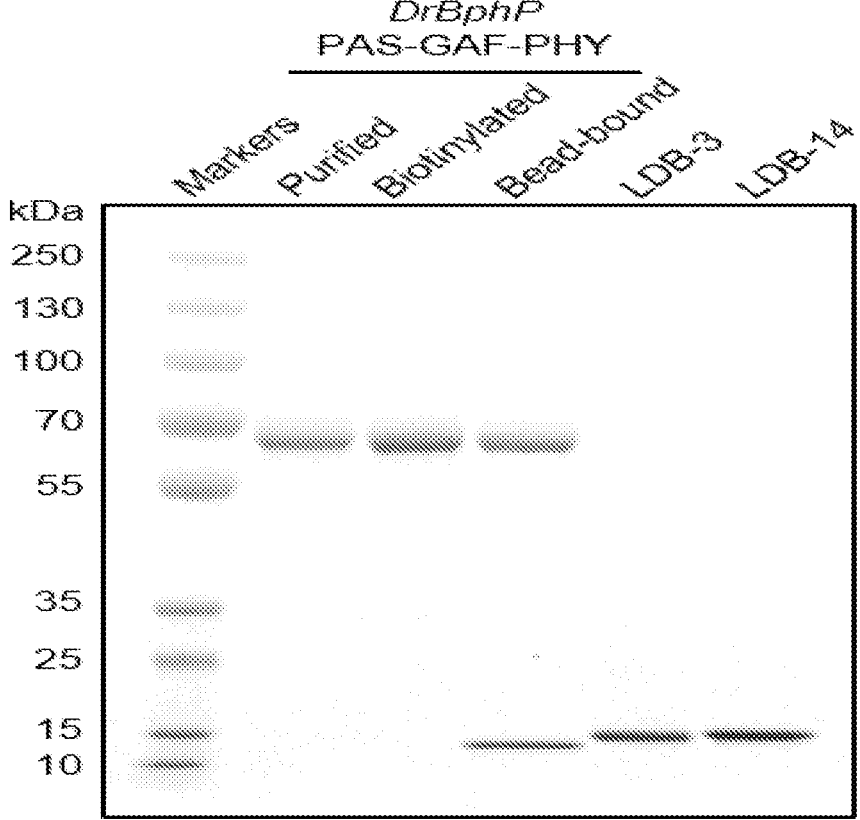

FIG. 8. SDS-PAGE analysis of purified DrBphP and nanobodies. Proteins were purified by nickel affinity and SEC chromatography. To examine in vitro biotinylation efficiency by BirA, the biotinylated protein was bound to streptavidin beads (Dynabeads™ M-280 Streptavidin, Thermo Fisher Scientific) and the bound protein (lane 4) was compared with the input protein (lane 3). The lower band in the lane 4 was streptavidin released from the beads when boiling the sample in an SDS loading buffer.

FIG. 9(*a-b*). Structures and spectra of the dark and light forms of DrBphP. (a) Structures of DrBphP dark and light forms previously reportedshowing the biliverdin chromophore bound to a tri-domain photosensory module and conformational changes of a tongue motif interacting with the biliverdin binding pocket. (b) Absorption spectra of the dark and light states of the biotinylated DrBphP after the 775-nm (0.3 mW/cm$^2$, 10 min) and 654-nm (0.5 mW/cm$^2$, 2 min) illuminations, respectively.

FIG. 10(*a-b*). Column chromatography-based phage display selection. (a) Two-step biopanning FPLC setup. (b) Flow rate and illumination time setup. In the Step 1, 2 mL phage-displayed nanobodies were loaded to two connected transparent glass columns (HR 5/5, GE Healthcare) packed with 0.4 and 0.2 mL streptavidin agarose resin (Pierce). Before divided into the two columns, the resin was incubated with 1.2 mL 20 µM biotinylated DrBphP in the dark for 30 min. Next, DrBphP in the first (negative selection) and second (positive selection) columns were converted to the dark and light forms by the 775-nm (0.3 mW/cm$^2$, 10 min) and 654-nm (0.5 mW/cm$^2$, 2 min) illumination, respectively. After the phage injection, the flow rate was set to be 0.04 mL/min and then decreased to 0 when the UV 280 nm baseline was stable (i.e., non-bound phages were washed out). In the Step 2, the first column was removed, and phages were eluted from the second column by the 775-nm (0.8 mW/cm$^2$) illumination for a given time. A pre-elution fraction was collected as a control for the phage count comparison with a light elution fraction to estimate the ratio of phages specifically eluted by the light to those non-specifically eluted (refer to Table 3).

FIG. 11. Yeast two-hybrid screening. Phage display-enriched nanobodies, as preys, were subcloned to pGADT7 encoding a GAL4 AD domain. DrBphP, as a bait, was inserted to pGBKT7 encoding a GAL4 DNA-binding domain. The right panel shows a representative result of two replica spotted plates incubated in the dark or under the 654-nm illumination.

Figure 12:
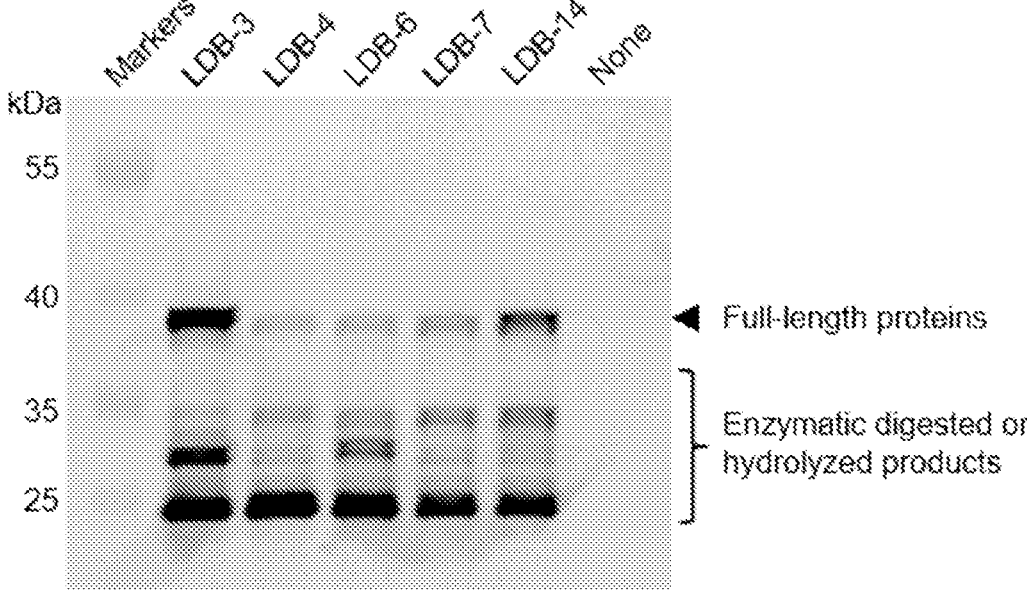

FIG. 12. In-gel detection of fluorescently labelled nanobodies expressed in HEK293T cells. Cells were transiently transfected with plasmids encoding SNAP-tagged nanobody fusions. Proteins in supernatants of sonication-lysed cells were specifically labeled with SNAP-Surface 649 and analyzed by SDS-PAGE and fluorescence imaging with an Odyssey CLx™ imaging system.

FIG. 13(*a-b*). Analytical SEC analyses of (a) nanobodies at different concentrations and (b) DrBphP in the light and dark forms. Proteins were loaded to a Superdex™ 200 Increase 10/300 GL column pre-equilibrated with 1× PBS and eluted at a flow rate of 0.75 mL/min at 4° C.

Figure 14:
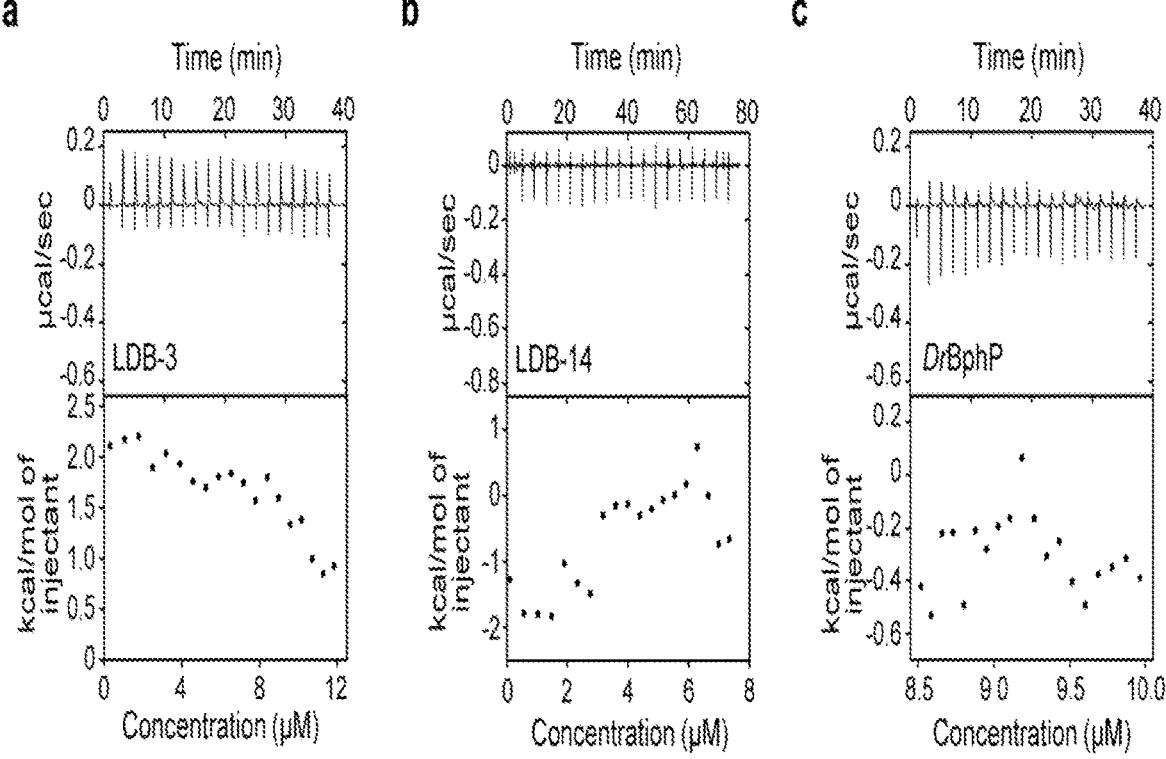

FIG. 14(*a-c*). ITC analysis of the titration of (a) 80 µM LDB-3 or (b) 50 µM LDB-14 into 1×PBS buffer, and (c) the titration of 1× PBS buffer into 10 µM DrBphP. The raw data (top) and the integration of heats (bottom) for each titration are shown.

Figure 15:
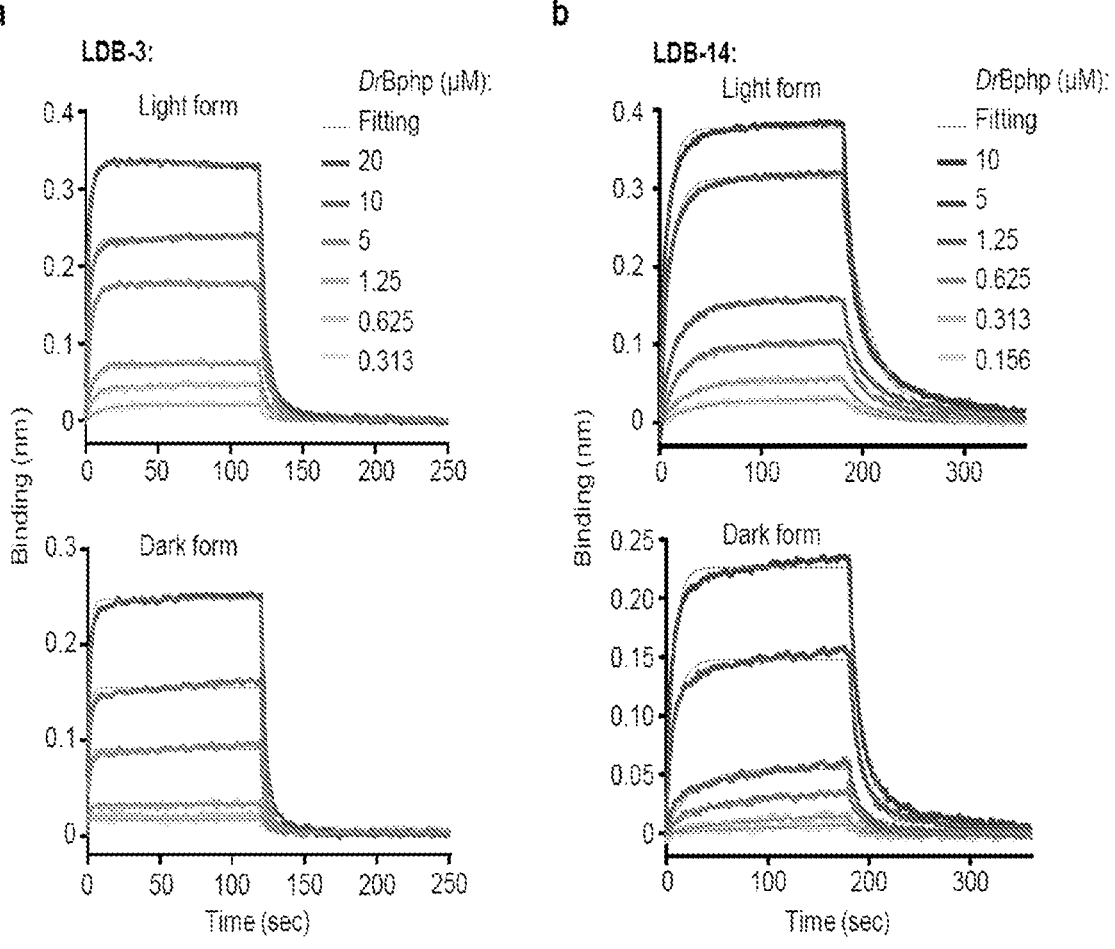

FIG. 15(*a-b*). BLI analysis of LDB-3 and LDB-14 binding kinetics. BLI sensorgrams show DrBphP binding to LDB-3 (a) and LDB-14 (b). Nanobodies were immobilized on Streptavidin biosensors and interacted with DrBphP after the 654-nm (light form) or 775-nm (dark form) illumination. Data were fitted using a global 1:1 model.

Figure 16:
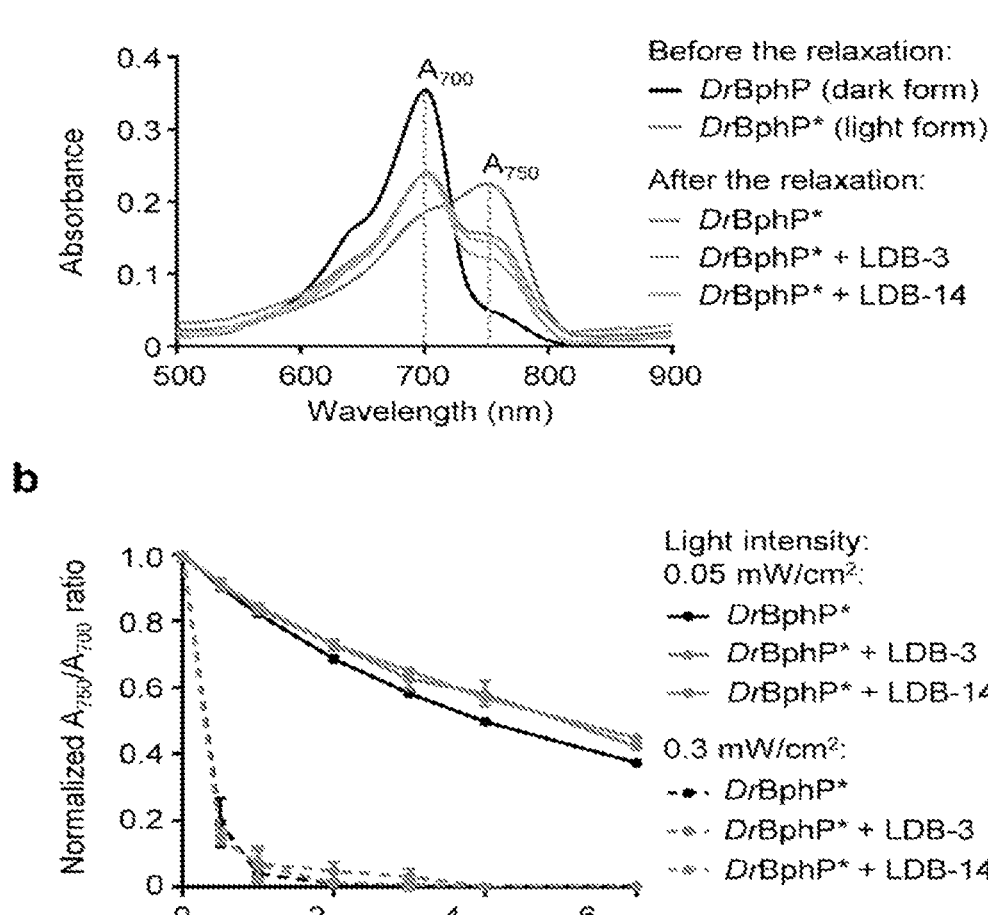

FIG. 16(*a-b*). Inhibition of DrBphP relaxation to the dark form by the nanobody binding. (a) Representative absorption spectra of the photoconverted light and dark forms and after the thermal relaxation by 775-nm illumination with or without LDB-3 or LDB-14 binding. (b) Time-course analysis of thermal relaxation rates of unbound and nanobody-bound light-form DrBphP by the 775-nm illumination. 400 µl 5 µM (final concentration) light-form DrBphP (after the 654-nm illumination at 0.5 mW/cm$^2$ for 2 min) was incubated with 5 µM (final concentration) LDB-3 or LDB-14 for 10 min before the thermal relaxation.

Figure 17:
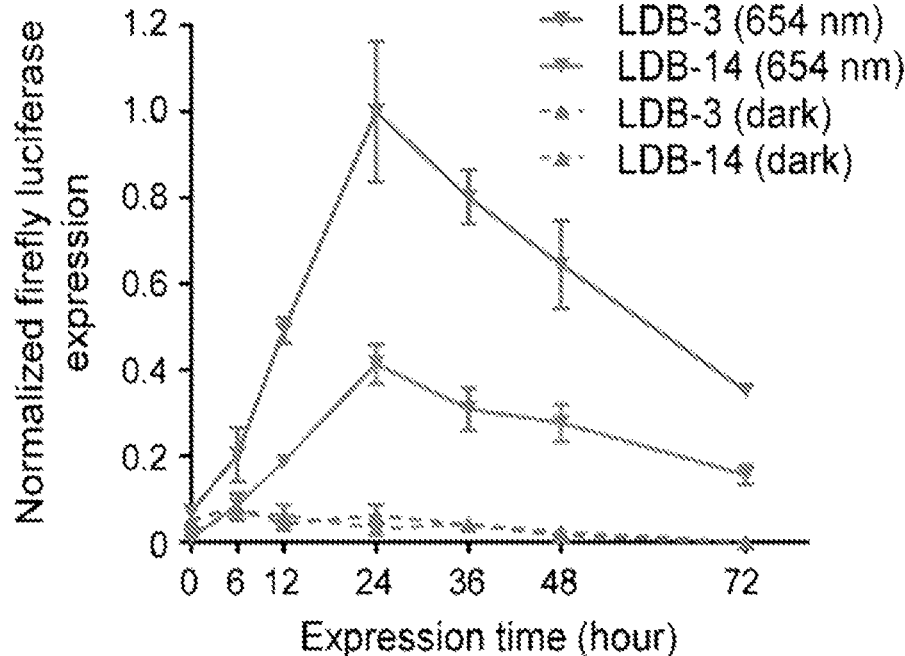

FIG. 17. Time-course analysis of red light-induced luciferase expression. HEK293T cells were co-transfected with the bait, prey, and GAL4UAS-luciferase reporter plasmids (~0.25 μg each) in a 0.5 mL culture. Transfected cells were incubated under the 654-nm (0.2 mW/cm²) illumination or in the dark. Data represent mean values of 3 measurements; error bars, standard deviation.

FIG. 18. Flowchart and timeline of COMBINES-LID.

DETAILED DESCRIPTION

In a first aspect, the disclosure provides Deinococcus radiodurans bacteriophytochrome (DrBphP) light form-binding antibodies, comprising a set of complementarity-determining regions (CDRs) selected from the group consisting of a CDR1, CDR2, and CDR3 combination selected from the group consisting of:

(a) SEQ ID NO:1 (CDR1), SEQ ID NO:2 (CDR2), and SEQ ID NO:3 (CDR3); or (b) SEQ ID NO:4 (CDR1), SEQ ID NO:5 (CDR2), and SEQ ID NO:6 (CDR3).

Table 6 provides the CDR sequences.

TABLE 6

CDR sequences of light-induced dimerization (LID) binder clones

| Row | IDs | CDR1 | CDR2 | CDR3 |
|---|---|---|---|---|
| 1 | LDB-3 | FTWDHYI (SEQ ID NO: 1) | ENGDAWN (SEQ ID NO: 2) | IGFDVPSGR SWQGSHFWM (SEQ ID NO: 3) |
| 2 | LDB-14 | TTSRWES (SEQ ID NO: 4) | WQNNSVP (SEQ ID NO: 5) | AQHNFLGHR (SEQ ID NO: 6) |

As described herein, the antibodies herein can be used, for example, as the effector protein in a light-induced dimerization (LID) system as described in detail in the examples that follow. As detailed in therein, a light inducted dimerization (LID) system comprises two separate proteins or domains which serve as a sensor and an effector (dimerization binder). The antibodies of the present disclosure can, for example, serve as the effector protein when a sensor comprises the photosensory module of Deinococcus radiodurans bacteriophytochrome (DrBphP). The antibodies of the present disclosure specifically bind to DrBphP in its light form, and can be used, in non-limiting examples, to control light activated gene expression and spatiotemporal activation of chimeric antigen receptor T (CAR-T) cells.

As disclosed herein, "antibody" refers to immunoglobulin molecules and immunologically active portions of immunoglobulin molecules, i.e., molecules that contain the one of the listed CDR sets and binds to DrBphP in its light form, as described in detail in the examples. As such, the term antibody encompasses not only whole antibody molecules, but also antibody fragments as well as variants (including derivatives) of antibodies and antibody fragments. Such antibody or antibody fragments thereof may include, but are not limited to a monoclonal antibody, humanized antibody, chimeric antibody, Fab', F(ab')₂, Fab, Fv, rIgG, recombinant single chain Fv fragments (scFv), single-domain antibody (nanobody), bivalent or bispecific molecule, diabody, triabody, and tetrabody, or fragments thereof. In one specific embodiment, the antibody comprises a single-domain antibody. In any embodiment herein, the antibodies may be recombinant antibodies.

The antibodies may comprise a suitable scaffold sequence by which to appropriately present the 3 CDRs. Any scaffold sequence may be used, as deemed suitable for an intended use. In one embodiment, the scaffold comprises an amino acid sequence at least 40%, 45%, 50%, 55%, 60%, 65%, 70%, 75%, 80%, 85%, 90%, 91%, 92%, 93%, 94%, 95%, 96%, 97%, 98%, 99%, or 100% identical to the following amino acid sequence: EVQLQASGGGFVQPGGSLRLS-CAASG (SEQ ID NO: 46)-(CDR1)-MGWFRQAPGK-EREFVSAIS (SEQ ID NO: 47)-(CDR2)-YY-ADSVKGRFTISRDNSKNTVYLQMNSLRAEDTAT-YYCA (SEQ ID NO: 48)-(CDR3)-YWGQGTQVTVSS (SEQ ID NO:49).

In another embodiment, the scaffold comprises an amino acid sequence at least 40%, 45%, 50%, 55%, 60%, 65%, 70%, 75%, 80%, 85%, 90%, 91%, 92%, 93%, 94%, 95%, 96%, 97%, 98%, 99%, or 100% identical to the following amino acid sequence: EVX1LQASGGGFX2X3PGGSLRLSX4AASG (SEQ ID NO: 50)-(CDR1)-MGWX5RQX6PX7KEREFVSAIS (SEQ ID NO: 51)-(CDR2)-YYX8DX9VKGRFTISRDNX10KNTX11YLQMX1-2SLX13X14EDTAX15YYCX16 (SEQ ID NO: 52)-(CDR3)-YWGQGTQVTVSS (SEQ ID NO: 49); wherein X1 is K, Q, N, R, D, or E;

X2 is D, G, E, A, V, L, or I;

X3 is L, F, W, G, A, V, L, or I;

X4 is K, R, D, E, N, or Q,

X5 is V, P, G, A, L, I, or M;

X6 is T, A, S, G, V, L, or I;

X7 is E, G, D, A, V, L, or I;

X8 is P, A, M, G, V, L, or I;

X9 is T, or S;

X10 is A, S, M, G, V, L, or I;

X11 is L, V, G, A, or I;

X12 is S, N, Q, or T;

X13 is K, R, D, or E;

X14 is S, A, T, G, V, L, or I;

X15 is M, T, V, L, or I;

X16 is V, G, L, I, or A.

In each of these embodiments, the CDR1, CDR2, and CDR3 is a set of CDRs provided in Table 6 (i.e.: CDR1 is SEQ ID NO:1, CDR2 is SEQ ID NO:2, and CDR3 is SEQ ID NO: 3; or CDR1 is SEQ ID NO:4, CDR2 is SEQ ID NO:5, and CDR3 is SEQ ID NO:6). The defined sequences comprise a camelid-based universal scaffold, with the three variable complementarity-determining regions (CDRs) interspersed.

In one embodiment the percent identity requirement is based only on the scaffold sequence (i.e.: not including identity with the CDR sequence). In another embodiment, the percent identity requirement is based on the scaffold sequence and a set of CDRs.

In one embodiment, the antibody comprises an amino acid sequence at least 40%, 45%, 50%, 55%, 60%, 65%, 70%, 75%, 80%, 85%, 90%, 91%, 92%, 93%, 94%, 95%, 96%, 97%, 98%, 99%, or 100% identical along the length of the amino acid sequence of SEQ ID NO: 9 or SEQ ID NO:10.

```
LDB-3
EVQLQASGGGFVQPGGSLRLSCAASGFTWDHYIMGWFRQAPGKEREFVSAISENGDAWNY        60

LDB-14
EVQLQASGGGFVQPGGSLRLSCAASGTTSRWESMGWFRQAPGKEREFVSAISWQNNSVPY        60
*************************      *******************      *
                             CDR3

LDB-3
YADSVKGRFTISRDNSKNTVYLQMNSLRAEDTATYYCAIGFDVPSGRSWQGSHFWMYWGQ       120

LDB-14
YADSVKGRFTISRDNSKNTVYLQMNSLRAEDTATYYCAAQH------NFLGH---RYWGQ       120
*************************************       ***
LDB-3

GTQVTVSS (SEQ ID NO: 9)                                            128

LDB-14
GTQVTVSS (SEQ ID NO: 10)                                           219
```

The antibodies can tolerate significant substitutions in the scaffold residues. In some embodiments, a given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are known. Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser(S), Thr (T), Cys (C), Tyr (Y), Asn (N), Gln (Q); (3) acidic: Asp (D), Glu (E); (4) basic: Lys (K), Arg (R), His (H). Alternatively, naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class. Particular conservative substitutions include, for example; Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

In all of these embodiments, the percent identity requirement does not include any additional functional domain that may be incorporated in the polypeptide. In all embodiments, any N-terminal methionine residue is optional and may be present or absent, and is not considered when determining percent identity.

In another embodiment of any of the above embodiments, the antibodies further comprise one or more functional domains. As used herein, a "functional domain" is any polypeptide of interest that might be fused or covalently bound to the polypeptides of the disclosure. In non-limiting embodiments, such functional domains may comprise one or more polypeptide antigens, polypeptide therapeutics, enzymes (e.g., Cre recominase), detectable domains (ex: fluorescent proteins or fragments thereof), DNA binding proteins, transcription factors, membrane receptors (e.g., T cell receptors) and their binding regulators, etc. The one or more functional domains may be fused at any appropriate regions within the polypeptides of the disclosure, including but not limited to at the N-terminus or at the C-terminus of the polypeptide.

In a further embodiment, a plurality of the antibodies are bound to a solid support. Any suitable solid support may be used, including but not limited to paper, nitrocellulose, beads, cell culture plates, nanoparticles, etc.

The antibodies of the disclosure may include additional residues at the N-terminus, C-terminus, internal to the polypeptide, or a combination thereof; these additional residues are not included in determining the percent identity of the polypeptides of the invention relative to the reference polypeptide. Such residues may be any residues suitable for an intended use, including but not limited to detectable proteins or fragments thereof (also referred to as "tags"). As used herein, "tags" include general detectable moieties (i.e.: fluorescent proteins, antibody epitope tags, etc.), therapeutic agents, purification tags (His tags, etc.), linkers, ligands suitable for purposes of purification, ligands to drive localization of the polypeptide, peptide domains that add functionality to the polypeptide of the disclosure.

The antibodies can include genetically coded and non-genetically coded amino acids, chemically or biochemically modified or derivatized amino acids, and modified peptide backbones. The recombinant antibodies may comprise L-amino acids+glycine, D-amino acids+glycine (which are resistant to L-amino acid-specific proteases in vivo), or a combination of D- and L-amino acids+glycine. The recombinant antibodies described herein may be chemically synthesized or recombinantly expressed. The recombinant antibodies may be linked to other compounds to promote an increased half-life in vivo, such as by PEGylation, HESylation, PASylation, glycosylation, or may be produced as an Fc-fusion or in deimmunized variants. Such linkage can be covalent or non-covalent as is understood by those of skill in the art.

In another aspect, the disclosure provides nucleic acids encoding the antibody of any embodiment or combination of embodiments of the disclosure. The nucleic acid sequence may comprise single stranded or double stranded RNA or DNA in genomic or cDNA form, or DNA-RNA hybrids, each of which may include chemically or biochemically modified, non-natural, or derivatized nucleotide bases. Such nucleic acid sequences may comprise additional sequences useful for promoting expression and/or purification of the encoded polypeptide, including but not limited to poly A sequences, modified Kozak sequences, and sequences encoding epitope tags, export signals, and secretory signals, nuclear localization signals, and plasma membrane localization signals. It will be apparent to those of skill in the art, based on the teachings herein, what nucleic acid sequences will encode the polypeptides of the disclosure.

In another aspect, the disclosure provides expression vectors comprising the nucleic acid of any embodiment or combination of embodiments of the disclosure, operatively linked to a control sequence. "Expression vector" includes vectors that operatively link a nucleic acid coding region or gene to any control sequences capable of effecting expression of the gene product. "Control sequences" operatively linked to the nucleic acid sequences of the disclosure are nucleic acid sequences capable of effecting the expression of the nucleic acid molecules. The control sequences need not be contiguous with the nucleic acid sequences, so long as they function to direct the expression thereof. Thus, for example, intervening untranslated yet transcribed sequences can be present between a promoter sequence and the nucleic acid sequences and the promoter sequence can still be considered "operably linked" to the coding sequence. Other such control sequences include, but are not limited to, polyadenylation signals, termination signals, and ribosome binding sites. Such expression vectors can be of any type, including but not limited plasmid and viral-based expression vectors. The control sequence used to drive expression of the disclosed nucleic acid sequences in a mammalian system may be constitutive (driven by any of a variety of promoters, including but not limited to, CMV, SV40, RSV, actin, EF) or inducible (driven by any of a number of inducible promoters including, but not limited to, tetracycline, ecdysone, steroid-responsive). The expression vector must be replicable in the host organisms either as an episome or by integration into host chromosomal DNA. In various embodiments, the expression vector may comprise a plasmid, viral-based vector, or any other suitable expression vector.

In a further aspect, the disclosure provides cells that comprises the antibody, nucleic acid, or expression vector (i.e.: episomal or chromosomally integrated) of any embodiment or combination of embodiments. The host cells can be either prokaryotic or eukaryotic.

In another aspect, the disclosure provides kit, comprising:
(a) the antibody, nucleic acid, expression vector, and/or cell of any of any embodiment or combination of embodiments disclosed herein; and
(b) a photosensory module of Deinococcus radiodurans bacteriophytochrome (DrBphP), including but not limited to a polypeptide at least 70%, 75%, 80%, 85%, 90%, 91%, 92%, 93%, 94%, 95%, 96%, 97%, 98%, 99%, or 100% identical to the amino acid sequence of SEQ ID NO: 11, wherein optional residues in parentheses may be present or absent and are not considered when determining the percent identity when absent, a nucleic acid encoding such a photosensory module of DrBphP, an expression vector comprising the nucleic acid encoding such a photosensory module of DrBphP operatively linked to a control sequence, and/or cell comprising the photosensory module of DrBphP, the nucleic acid encoding the photosensory module of DrBphP, and/or the expression vector comprising the nucleic acid encoding a photosensory module of DrBphP operatively linked to a control sequence.

Any suitable expression vector may be used as deemed appropriate for an intended purpose, including but not limited to pcDNA3 or pBAD plasmids. Any suitable cell may be used as deemed appropriate for an intended purpose, including but not limited to HEK293T cells.

```
                                    (SEQ ID NO: 11)
(M)SRDPLPFFPPPLYLGGPEITTENCEREPIHIPG

SIQPHGALLTADGHSGEVLQMSLNAATFLGQEPTV

LRGQTLAALLPEQWPALQAALPPGCPDALQYRATL

DWPAAGHLSLTVHRVGELLILEFEPTEAWDSTGPH

ALRNAMFALESAPNLRALAEVATQTVRELTGFDRV

MLYKFAPDATGEVIAEARREGLHAFLGHRFPASDI

PAQARALYTRHLLRLTADTRAAAVPLDPVENPQTN

APTPLGGAVLRATSPMHMQYLRNMGVGSSLSVSVV

VGGQLWGLIACHHQTPYVLPPDLRTTLEYLGRLLS

LQVQVKEAADVAAFRQSLREHHARVALAAAHSLSP

HDTLSDPALDLLGLMRAGGLILRFEGRWQTLGEVP

PAPAVDALLAWLETQPGALVQTDALGQLWPAGADL

APSAAGLLAISVGEGWSECLVWLRPELRLEVAWGG

ATPDQAKDDLGPRHSFDTYLEEKRGYAEPWHPGEI

EEAQDLRDTLTGAL
```

As described herein, the kits disclosed can be used, for example, as a light-induced dimerization (LID) system. As detailed in the examples, an LID system comprises two separate proteins or domains which serve as a sensor and an effector (dimerization binder). The antibodies of the present disclosure can, for example, serve as the effector protein when a sensor comprising the photosensory module of Deinococcus radiodurans bacteriophytochrome (DrBphP). The polypeptides of the present disclosure specifically bind to DrBphP in its light form, and can be used, in non-limiting examples, to optogenetically control CAR-T cell activation in specific organ and tissue regions, such as a solid tumor region, the LID system can be used to control the expression of chimeric TCR genes or the interaction of the chimeric TCR and a costimulatory domain, such as CD3ζ, to activate the TCR signaling pathway by separately fusing the photoreceptor and the antibody to the TCR and the costimulatory domain.

In one aspect, the disclosure provides methods for use of the antibodies, kits, nucleic acids, expression vectors, or host cell of any embodiment or combination of embodiments disclosed herein for any suitable purpose, including but not limited to use of an LID system for any purpose, including but not limited to control light activated gene expression and spatiotemporal activation of chimeric antigen receptor T (CAR-T) cells, or precisely controlling the split Cre recombinase in genetically modified animals, etc.

In another aspect, the disclosure provides methods for making light induced dimerization (LID) systems. The methods are described in detail in the examples, and comprise:
(1) phage display to enrich binders (such as nanobodies) that only bind to the light form of a conformation switcher (i.e.: changes conformation when exposed to light); and
(2) yeast two-hybrid (Y2H) screening of the enriched sub-library to select for in vivo activity (See FIG. 1b).

Such LID systems may be constructed using polypeptides selected from a vastly diverse synthetic combinatorial library. The combinatorial library may comprise DNA sequences chemically synthesized by a combinatorial method, such as a trinucleotide mutagenesis technology (PMID: 7838712), to obtain the diversity higher than $10^9$. The DNA sequences may encode polypeptides consisting of a consensus sequence, typically providing a structural scaffold, such as an immunoglobulin, non-immunoglobulin (PMID: 25931178), or computationally designed scaffold, and variable loop sequences, similar to complementarity determining regions (CDRs) of antibodies, which are structurally flexible and thus can be rationally randomized by incorporating a combination of amino acids under a given ratio into each loop sequence positions. Since both the polypeptides that form a LID system can be selected from a combinatorial library, this selection method may be applicable to generate LID systems for a wide range of light-induced conformation switching sensor molecules. These methods are a significant improvement over prior methods which rely on the using naturally occurring LID systems and their derivatives with intrinsic limitations, such as complex structures and the high dark activity, which requires further engineering of protein structures and activities.

In one embodiment, the methods comprise (a) screening a synthetic combinatorial polypeptide library with a light form of a conformation switcher to identify binding polypeptides; and (b) screening a synthetic combinatorial polypeptide library with a dark form of a conformation switcher (conformation assumed when not exposed to light) to identify dimerization polypeptides in the library that (i) bind to the light form of a conformation switcher, and (ii) do not bind to the dark form of a conformation switcher. In one embodiment, the polypeptide library may comprise a synthetic combinatorial immunoglobulin, non-immunoglobulin, or computationally designed library, such as a single-domain antibody library. In another embodiment, the screening in step (a) is carried out 1, 2, 3, 4, 5, 6, or more times. In a further embodiment, the screening in step (b) is carried out 1, 2, 3, 4, 5, 6, or more times. The methods may further comprise any other suitable steps, including but not limited to any step or combination of steps disclosed in the examples.

EXAMPLES

Summary: Protein dimerization systems that can be controlled by red light with increased tissue penetration depth are a highly needed tool for clinical applications such as cell and gene therapies. However, existing red light-induced dimerization systems are all based on phytochrome photoreceptors and naturally occurring binding partners with complex structures and suboptimal in vivo performance, limiting mammalian applications. Here, we introduce an efficient, generalizable method combinatorial binders-enabled selection of light induced dimerization (COMBINES-LID) for creating highly specific light-induced dimerization systems. It involves a two-step binder screen (phage display and yeast two-hybrid) of a combinatorial nanobody library to obtain binders that selectively engage a light-activated form of a photoswitchable protein or domain not the dark form. Proof-of-principle was provided by creating nanobody-based, red light-induced dimerization (nanoReD) systems comprising a truncated bacterial phytochrome sensory module using a mammalian endogenous chromophore, biliverdin, and a light-form specific nanobody. Selected nanoReD systems were biochemically characterized and exhibited low dark activity and high induction specificity for in vivo activation of gene expression. Overall, COMBINES-LID opens new opportunities for creating genetically encoded actuators for the optimal manipulation of biological processes Different from single-component actuator systems such as microbial opsins, light-induced protein dimerization (LID) systems comprises two separate proteins or domains which serve as a sensor and an effector. The sensory function is initiated by i) light-induced chromophore isomerization or chromophore-protein bond formation triggering a conformational change of a chromophore-bound photosensory protein (hereafter named 'conformation switcher'), or ii) photolytic release of a caged ligand or isomerization of a photoswitchable ligand that serves as a dimerization inducer. Naturally occurring conformation switchers widely exist in all kingdoms of life and many have been identified and characterized in the past three decades (Table 1). They have diverse structural and optical properties, offering flexible choices for in vivo applications. Many use widely shared metabolites from bacteria to humans as chromophores; for example, riboflavin-5'-phosphate bound to light-oxygen-voltage (LOV) sensing domains and biliverdin, a heme-derived linear tetrapyrrole found in bacteriophytochrome (BphP).

TABLE 1

Summary of photoswitchable proteins or domains that can potentially be used as conformational switchers in LID systems.

| Photo-switchable proteins (or domains) | Example(s) | Chromophore(s) | Excitation λ (nm) | Reversion λ (nm) | Oligomeric state | | Natural light induced binder(s) | Reference(s) |
| --- | --- | --- | --- | --- | --- | --- | --- | --- |
| | | | | | Dark form | Light form | | |
| UV receptors | UVR8 | Trp | ~300 | Dark | Dimer | Monomer | COP1 | 5-7 |
| Cyanobacterio-chromes | CcaS | PCB | ~535 | ~672/dark | Monomer | Monomer | CcaR | 8-9 |
| | cPAC | PCB | ~410 | ~520/dark | Dimer | Dimer | Unknown | 10 |
| | UirS | PCB | ~400 | ~530/dark | Monomer | Monomer | UirR | 11-12 |
| Sensors of blue-light using FAD (BLUF) domains | PixD | FAD or FMN | ~450 | Dark | Decamer | Dimer | PixE | 13-15 |
| | bPAC | FAD or FMN | ~450 | Dark | Dimer | Dimer | Unknown | 16-18 |

TABLE 1-continued

Summary of photoswitchable proteins or domains that can potentially
be used as conformational switchers in LID systems.

| Photo-switchable proteins (or domains) | Example(s) | Chromophore(s) | Excitation λ (nm) | Reversion λ (nm) | Oligomeric state | | Natural light induced binder(s) | Reference(s) |
|---|---|---|---|---|---|---|---|---|
| | | | | | Dark form | Light form | | |
| LOV domains | AsLOV2 | FMN | ~450 | Dark | Monomer | Monomer | Unknown | 19-21 |
| | YtvA | FAD, FMN, or riboflavin | ~450 | Dark | Dimer | Dimer | Unknown | 22-24 |
| | VVD | FAD or FMN | ~450 | Dark | Monomer | Dimer | VVD | 25-27 |
| | FKF1 | FMN | ~450 | Dark | Monomer | Dimer | GI | 28-30 |
| | EL222 | FMN | ~450 | Dark | Monomer | Dimer | Unknown | 31-32 |
| Cryptochromes | CRY2 | FAD | ~450 | Dark | Monomer | Monomer | CIB1 | 33-34 |
| Fluorescent protein domains | Dronpa1 45K/N | p-HBI | ~400 | ~500/dark | Monomer | Dimer | Unknown | 35-36 |
| | PYP | p-coumaric acid | ~450 | Dark | Monomer | Monomer | Unknown | 37-38 |
| Opsins | BeCyclOp | Retinal | ~530 | Dark | Dimer | Dimer | Unknown | 39 |
| Cobalamin binding domains (CBDs) | TtCBD | AdoCbl, MetCbl, or CNCbl | ~545 | Dark | Tetramer | Monomer | Unknown | 40 |
| | MxCBD | AdoCbl, MetCbl, or CNCbl | ~545 | Dark | Tetramer | Monomer | Unknown | 40 |
| Phytochromes | RpBphP1 | BV | ~740 | ~636/dark | Dimer | Dimer | PpsR2 | 41-42 |
| | DrBphP | BV | ~655 | ~780/dark | Dimer | Dimer | Unknown | 4, 43-44 |
| | Cph1 | PCB or PΦB | ~657 | ~731/dark | Dimer | Dimer | Unknown | 45-47 |
| | PhyB | PCB | ~660 | ~740/dark | Monomer | Monomer | PIF3/PIF6 | 48-50 |

Figure 1:
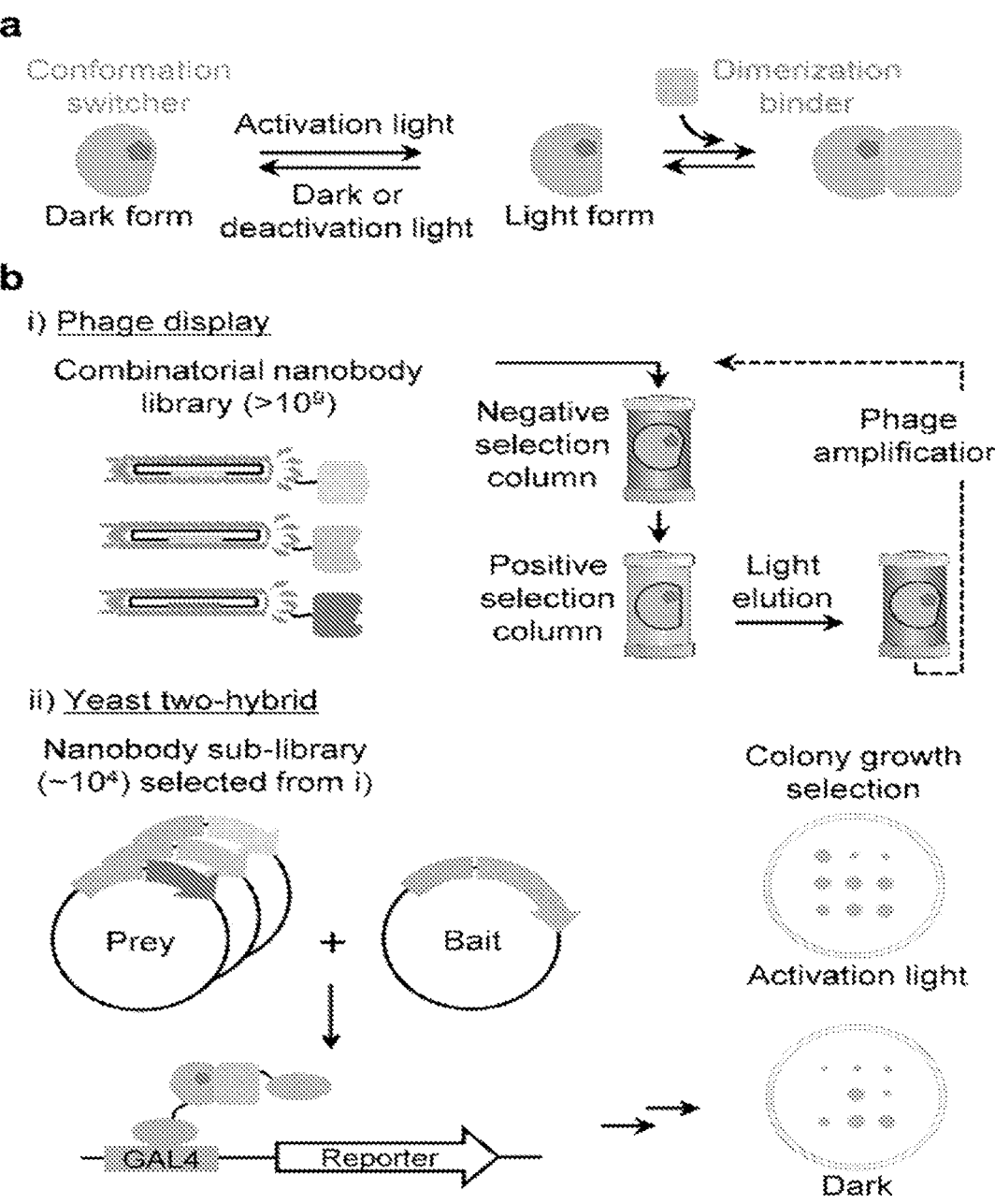
FIG. 1($a$-$b$). Schematics of LID (a) and the COMBINES-LID method (b).

The effector function of LID is executed by a 'dimerization binder' which specifically binds to the conformation switcher in its light form—the state after a light-induced conformational change occurring to its thermally stable state in the dark, or the dark form (FIG. 1a). Many natural conformation switchers do not modulate protein-protein interaction and are not associated with any known dimerization binders; for example, in phytochromes, conformation switcher domains (known as a photosensory module) are typically fused with an enzymatic domain or module to allosterically regulate catalytic activity. Although a few natural dimerization binders have been identified (Table 1), they are limited by the basal activity in the dark (or dark activity) and other undesirable properties. It is yet difficult to design new dimerization binders with suitable specificity, sensitivity, and kinetics.

For deep-tissue applications in animals, LID is required to sense an optical input in the 650-900 nm region, known as a tissue transparency window, because tissue absorbance, autofluorescence, and light scattering are minimized in this region.

Results and Discussion

Screening of Dimerization Binders for DrBphP. We devised a two-step screening method, combinatorial binders-enabled selection of LID (COMBINES-LID), which involves phage display to enrich binders that only bind to the BphP light form and then yeast two-hybrid (Y2H) screening of the enriched sub-library to select for in vivo activity (FIG. 1b). A high-quality synthetic combinatorial nanobody library generated in our previous work was used. These nanobodies have an optimized scaffold and rationally randomized CDRs with an estimated sequence diversity of 1.23 to $7.14 \times 10^9$.

To simplify the structure of the conformation switcher, the photosensory module of Deinococcus radiodurans bacterio-phytochrome (DrBphP) was chosen. Its light and dark forms can be photoconverted by activating far-red (e.g., 654 nm) and deactivating NIR (e.g., 775 nm) illuminations, respectively, and then stably maintained in a screening assay. The photoswitching efficiency is close to that of the full-length DrBphP. By contrast, the excised module of RpBphP1 showed impaired photoconversion.[10] The tridomain module (hereafter named DrBphP for simplicity) comprising a Per-ARNT-Sim (PAS), a cGMP phosphodiesterase-adenylate cyclase-FhlA (GAF), and a phytochrome-specific (PHY) domains was expressed as a ~60 kDa fusion bearing a C-terminal AviTag and HisTag, incubated with biliverdin, purified, and biotinylated (FIG. 8) to serve as a bait for phage display. The photoconversion of the purified protein was confirmed by measuring the spectra of the light and dark forms (FIG. 9).

We hypothesized that specific and reversible dimerization binders are critical for the in vivo performance of LID, such as a low dark activity. To enhance selection efficiency, we used column chromatography to continuously separate phage-displayed nanobodies between the stationary and mobile phases as they passed through a column. Binding specificity was selected by loading the library onto two connected transparent columns, the first (negative selection) preloaded with biotinylated DrBphP in the dark form and the second (positive selection) with the light form (FIG. 10a). Thus, nanobodies captured in the second column should have zero or very low affinity to the dark form. Next, reversible binders were collected by eluting only dissociated nanobodies from the second column after switching the light to dark form by the 775-nm illumination. After four-round phage binding and elution with gradually decreased illumination times (FIG. 10b), the final eluent was estimated to contain ~90% light-eluted clones (Table 2) with the sequence diversity of ~$10^4$.

TABLE 2

Enrichment of phage titers following each round of
biopanning for the dimerization binder selection.

| Round | Input count | Pre-elution count* | 775 nm light elution count** |
|---|---|---|---|
| 1 | $\sim 1 \times 10^{14}$ | $\sim 5.4 \times 10^6$ | $\sim 2.0 \times 10^6$ |
| 2 | $\sim 1 \times 10^{13}$ | $\sim 1.2 \times 10^5$ | $\sim 2.3 \times 10^5$ |
| 3 | $\sim 1 \times 10^{13}$ | $\sim 1.8 \times 10^5$ | $\sim 7.3 \times 10^5$ |
| 4 | $\sim 1 \times 10^{13}$ | $\sim 1.5 \times 10^7$ | $\sim 1.4 \times 10^8$ |

Note:
After phage binding, the positive selection column was washed with ~30 mL 0.05% PBST buffer. 2 mL pre-elution fraction (*) was collected at 0.5 mL/min immediately before the 775 nm-illumination at 0 mL/min. 2 mL elution fraction (**) was collected at 0.5 mL/min immediately after the illumination. Phage titers of the collected fractions were measured to determine the enrichment of clones specifically eluted by the light for each selection round.

In vitro selected nanobodies were subcloned into a Y2H sub-library for the cell-based screening of cytoplasmic expression and binding specificity. Y2H was selected for the sub-library screening due to its suitable throughput and cost-effectiveness. Y2HGold cells were co-transformed with plasmids carrying genes of DrBphP and nanobodies and selected on SD/-Ade/-His/-Leu/-Trp agar plates under the 654-nm illumination. ~2,000 fully grown colonies were picked, inoculated into 1-mL SD/-Leu/-Trp medium, and replica spotted onto the agar plates to compare colony growth under the illumination and in the dark (FIG. 11a). Five candidates grew only under the illumination (FIG. 2a) and with diverse CDR sequences (Table 3) were selected for further characterization.

TABLE 3

CDR sequences of light-induced dimerization
binders (LDBs) characterized in the work.

| Nanobody | CDR1 | CDR2 | CDR3* | SEQ ID NOs: |
|---|---|---|---|---|
| LDB-3 | FTWDHYI | ENGDAWN | IGFDVPSGR SWQGSHFWM | 1, 2, 3 |
| LDB-4 | DTSYLYS | WWWNLTQ | WSIYFPPGN DYNGYH | 12, 13 ,14 |
| LDB-6 | FFSNWSD | FWADGTE | WYGPVNGFY MFD | 15, 16, 17 |
| LDB-7 | STSDFES | SWFTNPP | HRSIWYHPT | 18, 19, 20 |
| LDB-14 | TTSRWES | WQNNSVP | AQHNFLGHR | 4, 5, 6 |

To confirm the binding specificity and reversibility, we assayed selected nanobodies by single phage enzyme-linked immunosorbent assay (ELISA). Phage displayed-nanobodies were first bound to the dark and light forms of biotinylated DrBphP immobilized in streptavidin-coated microtiter plates. To maintain the dark or light form, or to convert the light to dark form, the plates were under 654- and/or 775-nm illumination during the phage binding and wash steps. As expected, all candidates showed light-form binding specificity with non-detectable (LDB-3 and LDB-6) to relatively low (LDB-4, LDB-7, and LDB-14) binding to the dark form (FIG. 2b). Bound nanobodies were almost completely (LDB-3, LDB-4, and LDB-6) or partially (LDB-7 and LDB-14) washed off after converting the light to dark form.

Specificity Validation in a Mammalian Cell line. To determine whether nanobody candidates are suitable for mammalian applications, we tested their expression in human embryonic kidney 293T (HEK293T) cells. It is known that the same protein-protein interaction (PPI) found in yeast might not be detected in mammalian cells due to protein expression or stability issues; for example, a recent comparison of PPI assays in different hosts found that only half of human PPIs detected in yeast were also seen in HEK293T, and vice versa.[24] Thus, we were interested to know the success rate of nanobodies selected by COMBINES-LID that can be functionally expressed in mammalian cells.

To compare in vivo activity, we assayed proteins by mammalian two-hybrid (M2H) 25 under a standardized condition. Specifically, DrBphP was fused with an N-terminal GAL4 DNA binding domain (BD) and nanobodies with a C-terminal p65 transcriptional activation domain (AD) to control the expression of a firefly luciferase reporter (FIG. 3a). After transient co-transfection with the BD and AD, and reporter plasmids, cells were cultured for 24 hours in the dark to express the DrBphP and nanobodies, and then maintained in the dark or under the 654-nm illumination for another 24 hours to compare the luciferase expression. Dark activity and specificity were analyzed by comparing the dark expression with a negative control (i.e., only DrBphP was expressed) and the light-induced expression with the dark expression, respectively. All candidates showed low dark activities, and the dark expression levels were close to the control (FIG. 3b). LDB-3 and LDB-14 showed the high specificity; their light-induced expression levels were increased by ~19.5 and ~19.1 folds, respectively. The other three candidates did not show obvious light activation. To understand their loss of the expected activity, we investigated protein stability in HEK293T. Specifically, all nanobodies bearing a C-terminal SNAP-tag were expressed, fluorescently labelled, and analyzed by sodium dodecyl sulfate gel electrophoresis (SDS-PAGE) to detect full-length proteins and degraded forms. All nanobodies were found with degraded fragments; however, compared with LDB-3 and LDB-14, the other three nanobodies showed drastically decreased levels of full-length proteins, suggesting that they might not be stable in the host cells (FIG. 12).

We compared the specificity of the nanobody-based LIDs with the RpBphP1-PpsR2 and RpBphP1-Q-PASI systems by M2H. The RpBphP1-based LIDs showed light-enhanced expression (FIG. 3b). Light-induced expression was increased by ~2.95 and ~2.02 folds. As suggested by a mathematical model of LID, the specificity is determined by not only relative binding affinities of dimerization binders to dark and light forms of a conformation switcher, but also by their effective cellular concentrations. Our comparison with the same transfection and culture condition suggests that LDB-3 and LDB-14 offer significantly enhanced dimerization specificity.

Biochemical Characterization of LDB-3 and LDB-14. We biochemically assessed selected nanobodies to understand their binding mechanisms. We first sought to detect light-induced DrBphP-nanobody complexes using analytical size-exclusion chromatography (SEC). LDB-3 and LDB-14 were bacterially expressed and purified with yields of ~2-3 milligrams per liter of culture. SEC data showed that LDB-3 was mixture of the monomer and dimer and LDB-14 mainly the monomer and both nanobodies dimerized at increased concentrations (FIG. 13a). Both the light and dark forms of DrBphP were eluted mainly as homodimers (FIG. 13b). After DrBphP was illuminated and then incubated with LDB-3 or LDB-14 in the dark, split SEC peaks of DrBphP were observed only for the light form (FIG. 4a), implying complex formation. Complexes were confirmed by SDS- PAGE detection of coeluted DrBphP and nanobodies (FIG. 4b). Interestingly, gel analysis revealed that LDB-3 was co-eluted with DrBphP later than LDB-14, suggesting that they might have different binding configurations or affinities. Consistent with the single phage ELISA result (FIG. 2b), LDB-14 appeared to weakly interact with the dark form since a faint nanobody band was detected in the dark-form DrBphP factions.

We next studied the thermodynamics of nanobody binding by isothermal titration calorimetry (ITC). Binding data obtained by titrating LDB-3 or LDB-14 into a photoconverted light-form sample were fitted using a one-site model ($R^2 = \sim 0.99$) to give apparent dissociation constants ($K_D^{app}$s) of 1.01 and 0.47 µM, respectively (FIG. 5 and Table 4). The binding site number of DrBphP was calculated to be ~0.6, consistent with a previous small-angle X-ray scattering result that only 64% of the protein molecules in the photo-converted sample adopted the light-state conformation. Unexpectedly, the thermograph of LDB-3 titration into the dark form showed significant heat exchange: a clear transition from heat release to absorption when more LDB-3 was added, which was not observed for LDB-3 titration into the light form (FIG. 5a). This transition suggests that the exothermic binding of LDB-3 to the dark form might be coupled to an endothermic process, which is likely to be the LDB-3 dimer dissociation (FIG. 14). In other words, LDB-3 binding to the dark form might be inhibited by LDB-3 dimerization, thus providing a mechanism to explain the observed low dark activity of LDB-3 (refer to the thermodynamic simulation in Materials and Methods). LDB-14 was found to only bind to a small fraction (~15%) of DrBphP in the dark-form sample but did not generate measurable heat of binding with the major population (FIG. 5b). The minor fraction was likely the protein switched to the light form during our assay.

TABLE 4

ITC-derived thermodynamic parameters for LDB-3 and LDB-14 binding to the DrBphP light form.

|  | n (stoichiometry) | $K_D^{app}$ (µM) | ΔH (kJ/mol) | ΔG (kJ/mol) | -TΔS (kJ/mol) |
|---|---|---|---|---|---|
| LDB-3 | 0.605 | 1.01 | −37.0 | −34.2 | 2.78 |
| LDB-14 | 0.556 | 0.47 | −112.8 | −36.1 | 76.7 |

The binding kinetics of LDB-3 and LDB-14 were measured by Bio-Layer Interferometry (BLI). The assay was performed by incubating the light or dark form with nanobodies immobilized on streptavidin biosensors (refer to Supplementary Methods). The result revealed that, compared with LDB-14, LDB-3 has a weaker binding affinity to the light form mainly due to a ~4.9-fold faster dissociation from the DrBphP ($k_{off} = \sim 18.5 \times 10^{-2} \text{s}^{-1}$) (FIG. 15 and Table 5). Theoretically, the fast dissociation could offer higher temporal resolution for the reversible control of LID. The BLI analysis of the dark form binding was not straightforward because the white light signal used by this optical technique might partially convert the biosensor-bound DrBphP to the light form.

TABLE 5

Kinetic parameters of selected dimerization binders binding to the light and dark forms.

|  | Molar ratio | $K_D^{app}$ ($10^{-6}$ M) | $K_{on}^{app}$ ($10^4$ M$^{-1}$ s$^{-1}$) | $K_{off}^{app}$ ($10^{-2}$ s$^{-1}$) |
|---|---|---|---|---|
|  |  | LDB-3 | | |
| Light form | 1:1 | 7.7 | 2.4 | 18.5 |
| Dark form* | 1:1 | 25 | 1.06 | 26.5 |
|  |  | LDB-14 | | |
| Light form | 1:1 | 2.4 | 1.56 | 3.74 |
| Dark form* | 1:1 | 10 | 0.607 | 6.07 |

Note:
*The dark form binding data are not reliable because the white light conducted to BLI biosensors might partially convert DrBphP to the light form.

Since DrBphP photoconversion and nanobody binding might reciprocally affect each other, we asked whether the nanobody binding can slow the photoconversion to the dark state. To test this, we illuminated DrBphP with different exposure times and light intensities and measured the percentage of the dark state in the protein by the ratio of absorption at 750 nm ($A_{750}$) to 700 nm ($A_{700}$) (FIG. 16a). Compared with unbound DrBphP, the nanobody-bound DrBphP had decreased photoconversion rates (FIG. 16b), suggesting that the nanobody binding can stabilize the light state. At a relatively low light intensity (0.05 mW/cm$^2$), the LDB-3-bound DrBphP had a slightly faster relaxation to the dark state than the LDB-14-bound DrBphP, likely due to the faster dissociation of the DrBphP-LDB-3 complex. Together, our biochemical data support the high specificity and reversibility of the nanobody-based LID systems.

Red Light-Activated Gene Expression. To develop in vivo applications, we focused on light-induced gene expression. We first determined the time-course response of light-induced activation of luciferase expression in HEK293T cells. Under the same culture and transfection condition, luciferase levels with or without 654-nm illumination were measured at seven time points up to 72 hours. For both LDB-3 and LDB-14, luciferase levels after illumination reached half maximum and maximum at 12 and 24 hours, respectively (FIG. 17). The half-maximum and maximum luciferase levels in cells expressing LDB-3 were ~2.5-fold higher than those of cells expressing LDB-14, which seems to be correlated with in vivo nanobody stability (FIG. 12).

The luciferase assay required releasing the protein by cell lysis, so we also measured in situ green fluorescent protein (GFP) expression by fluorescence imaging. Specifically, HEK293T cells were transiently co-transfected with LID genes to control the transcription of a chromosomally integrated GFP gene. Imaging analysis showed zero to very low GFP expression in cells kept in the dark (FIG. 6a). In LDB-3- and LDB-14-expressing cells, light-induced GFP levels were close and, compared with the expression in the dark, increased by ~44 and ~39 folds, respectively (FIG. 6b).

CONCLUSIONS

Our work demonstrated that COMBINES-LID is efficient for creating LID systems. This method screened a generic combinatorial nanobody library using fast and cost-effective phage display and Y2H techniques to obtain high-quality, mammalian-applicable binders without need for further engineering of binding affinity and specificity, thus offering a short turnaround time (FIG. 18). It relies on using protein targets with photo-induced light or dark-state specific conformational changes to select binder specificity, and theoretically can be applied to a large array of photoswitchable proteins (Table 2) to create orthogonal LID systems with diverse optical and structural properties. Applicable dimerization binders can also include those with other scaffolds such as non-immunoglobulin[28] and computationally designed scaffolds.

The LDB-3 and LDB-14-DrBphP LID systems, now named 'nanoReD1' and 'nanoReD2', respectively, have simplified structures and improved in vivo performance, overcoming the intrinsic limitations of naturally occurring BphP LID and its derivatives. These systems have been tested for light-activated gene expression, and are also useful for controlling other cellular processes, for example, the spatiotemporal activation of chimeric antigen receptor T (CAR-T) cells. Their use of the mammalian endogenous metabolite as chromophore and the compatibility of deep tissue penetration offer the unique potential to address clinical challenges such as CAR-T therapy targeting solid tumors.

Abbreviations

LID, light-induced protein dimerization; CID, chemically induced dimerization; COMBINES-LID, combinatorial binders-enabled selection of LID; nanoReD, nanobody-based, red light-induced dimerization; LOV, light-oxygen-voltage; NIR, near-infrared; BphP, bacterial phytochrome; CDR, complementarity-determining region; Y2H, yeast two-hybrid; ELISA, enzyme-linked immunosorbent assay; HEK293T, human embryonic kidney 293T cell; PPI, protein-protein interaction; BD, DNA binding domain; AD, activation domain; SDS-PAGE, sodium dodecyl sulfate gel electrophoresis; SEC, size-exclusion chromatography; ITC, isothermal titration calorimetry; $K_D^{app}$, apparent dissociation constant; BLI, Bio-Layer Interferometry; GFP, green fluorescent protein; CAR-T, chimeric antigen receptor T cell.

REFERENCES (1) Zhang, F.; Vierock, J.; Yizhar, O.; Fenno, L. E.; Tsunoda, S.; Kianianmomeni, A.; Prigge, M.; Berndt, A.; Cushman, J.; Polle, J.; Magnuson, J.; Hegemann, P.; Deisseroth, K. The Microbial Opsin Family of Optogenetic Tools. *Cell* 2011, 147, 1446-1457.

(2) Mayer, G.; Heckel, A. Biologically active molecules with a "light switch". *Angew. Chem. Int. Ed. Engl.* 2006, 45, 4900-4921.

(3) Christie, J. M.; Salomon, M.; Nozue, K.; Wada, M.; Briggs, W. R. LOV (light, oxygen, or voltage) domains of the blue-light photoreceptor phototropin (nph1): Binding sites for the chromophore flavin mononucleotide. *Proc. Natl. Acad. Sci. U.S.A* 1999, 96, 8779-8783.

(4) Bhoo, S. H.; Davis, S. J.; Walker, J.; Karniol, B.; Vierstra, R. D. Bacteriophytochromes are photochromic histidine kinases using a biliverdin chromophore. *Nature* 2001, 414, 776-779.

(5) Rockwell, N. C.; Su, Y. S.; Lagarias, J. C. Phytochrome structure and signaling mechanisms. *Annu. Rev. Plant Biol.* 2006, 57, 837-858.

(6) Weissleder, R. A clearer vision for in vivo imaging. *Nat. Biotechnol.* 2001, 19, 316-317.

(7) Weissleder, R.; Ntziachristos, V. Shedding light onto live molecular targets. *Nat. Med.* 2003, 9, 123-128.

(8) Jobsis, F. F. Noninvasive, infrared monitoring of cerebral and myocardial oxygen sufficiency and circulatory parameters. *Science* 1977, 198, 1264-1267.

(9) Chernov, K. G.; Redchuk, T. A.; Omelina, E. S.; Verkhushaa, V. V. Near-infrared fluorescent proteins, biosensors, and optogenetic tools engineered from phytochromes. *Chem. Rev.* 2017, 117, 6423-6446.

(10) Bellini, D.; Papiz, M. Z. Structure of a bacteriophytochrome and light-stimulated protomer swapping with a gene repressor. *Structure* 2012, 20, 1436-1446.

(11) Winkler, A.; Heintz, U.; Lindner, R.; Reinstein, J.; Shoeman, R. L.; Schlichting, I. A ternary AppA-PpsR-DNA complex mediates light regulation of photosynthesis-related gene expression. *Nat. Struct. Mol. Biol.* 2013, 20, 859-867.

(12) Kaberniuk, A. A.; Shemetov, A. A.; Verkhusha, V. V. A bacterial phytochrome-based optogenetic system controllable with near-infrared light. *Nat. Methods* 2016, 13, 591-597.

(13) Redchuk, T. A.; Omelina, E. S.; Chernov, K. G.; Verkhusha, V. V. Near-infrared optogenetic pair for protein regulation and spectral multiplexing. Nat. Chem. Biol. 2017, 13, 633-639.

(14) Kojadinovic, M.; Laugraud, A.; Vuillet, L.; Fardoux, J.; Hannibal, L.; Adriano, J. M.; Bouyer, P.; Giraud, E.; Vermeglio, A. Dual role for a bacteriophytochrome in the bioenergetic control of Rhodopsdeudomonas *palustris*: Enhancement of photosystem synthesis and limitation of respiration. *Biochim. Biophys. Acta* 2008, 1777, 163-172.

(15) Wagner, J. R.; Zhang, J. R.; Brunzelle, J. S.; Vierstra, R. D.; Forest, K. T. High resolution structure of Deinococcus bacteriophytochrome yields new insights into phytochrome architecture and evolution. *J. Biol. Chem.* 2007, 282, 12298-12309.

(16) Yang, X.; Kuk, J.; Moffat, K. Crystal structure of *Pseudomonas aeruginosa* bacteriophytochrome: Photoconversion and signal transduction. *Proc. Natl. Acad. Sci. U.S.A.* 2008, 105, 14715-14720.

(17) Guntas, G.; Hallett, R. A.; Zimmerman, S. P.; Williams, T.; Yumerefendi, H.; Bear, J. E.; Kuhlman, B. Engineering an improved light-induced dimer (iLID) for controlling the localization and activity of signaling proteins. *Proc. Natl. Acad. Sci. U.S.A.* 2015, 112, 112-117.

(18) Reis, J. M.; Xu, X. L.; McDonald, S.; Woloschuk, R. M.; Jaikaran, A. S. I.; Vizeacoumar, F. S.; Woolley, G. A.; Uppalapati, M. Discovering selective binders for photoswitchable proteins using phage display. *ACS Synth. Biol.* 2018, 7, 2355-2364.

(19) Muyldermans, S. Nanobodies: natural single-domain antibodies. *Annu. Rev. Biochem.* 2013, 82, 775-797.

(20) Kang, S.; Davidsen, K.; Gomez-Castillo, L.; Jiang, H.; Fu, X.; Li, Z.; Liang, Y.; Jahn, M.; Moussa, M.; DiMaio, F.; Gu, L. COMBINES-CID: An efficient method for de novo engineering of highly specific chemically induced protein dimerization systems. *J. Am. Chem. Soc.* 2019, 141, 10948-10952.

(21) Moutel, S.; Bery, N.; Bernard, V.; Keller, L.; Lemesre, E.; de Marco, A.; Ligat, L.; Rain, J. C.; Favre, G.; Olichon, A.; Perez, F. NaLi-H1: A universal synthetic library of humanized nanobodies providing highly functional antibodies and intrabodies. *eLife* 2016, 5, e16228.

(22) Wagner, J. R.; Zhang, J. R.; von Stetten, D.; Guenther, M.; Murgida, D. H.; Mroginski, M. A.; Walker, J. M.; Forest, K. T.; Hildebrandt, P.; Vierstra, R. D. Mutational analysis of Deinococcus radiodurans bacteriophytochrome reveals key amino acids necessary for the photochromicity and proton exchange cycle of phytochromes. *J. Biol. Chem.* 2008, 283, 12212-12226.

(23) Takala, H.; Bjorling, A.; Berntsson, O.; Lehtivuori, H.; Niebling, S.; Hoernke, M.; Kosheleva, I.; Henning, R.; Menzel, A.; Ihalainen, J. A.; Westenhoff, S. Signal amplification and transduction in phytochrome photosensors. *Nature* 2014, 509, 245-248.

(24) Choi, S. G.; Olivet, J.; Cassonnet, P.; Vidalain, P. O.; Lucks, K.; Lambourne, L.; Spirohn, K.; Lemmens, I.; Dos Santos, M.; Demeret, C.; Jones, L.; Rangarajan, S.; Bian, W.; Coutant, E. P.; Janin, Y. L.; van Der Werf, S.; Trepte, P.; Wanke, E. E.; De Las Rivas, J.; Tavernier, J.; Twizere, J. C.; Hao, T.; Hill, D. E.; Vidal, M.; Calderwood, M. A.; Jacob, Y. Maximizing binary interactome mapping with a minimal number of assays. *Nat. Commun.* 2019, 10, 3907.

(25) Lievens, S.; Lemmens, I.; Tavernier, J. Mammalian two-hybrids come of age. *Trends Biochem. Sci.* 2009, 34, 579-588.

(26) Ong, N. T.; Olson, E. J.; Tabor, J. J. Engineering an *E. coli* near-infrared light sensor. *ACS Synth. Biol.* 2018, 7, 240-248.

(27) Niu, J.; Ben Johny, M.; Dick, I. E.; Inoue, T. Following optogenetic dimerizers and quantitative prospects. *Biophys. J.* 2016, 111, 1132-1140.

(28) Skrlec, K.; Strukelj, B.; Berlec, A. Non-immunoglobulin scaffolds: a focus on their targets. *Trends Biotechnol.* 2015, 33, 408-418.

(29) Chevalier, A.; Silva, D. A.; Rocklin, G. J.; Hicks, D. R.; Vergara, R.; Murapa, P.; Bernard, S. M.; Zhang, L.; Lam, K. H.; Yao, G.; Bahl, C. D.; Miyashita, S. I.; Goreshnik, I.; Fuller, J. T.; Koday, M. T.; Jenkins, C. M.; Colvin, T.; Carter, L.; Bohn, A.; Bryan, C. M.; Fernández-Velasco, D. A.; Stewart, L.; Dong, M.; Huang, X.; Jin, R.; Wilson, I. A.; Fuller, D. H.; Baker, D. Massively parallel de novo protein design for targeted therapeutics. *Nature* 2017, 550, 74-79.

(30) Wu, C. Y.; Roybal, K. T.; Puchner, E. M.; Onuffer, J.; Lim, W. A. Remote control of therapeutic T cells through a small molecule-gated chimeric receptor. *Science* 2015, 350, aab4077.

(31) Huang, Z. L.; Wu, Y. Q.; Allen, M. E.; Pan, Y. J.; Kyriakakis, P.; Lu, S. Y.; Chang, Y. J.; Wang, X.; Chien, S.; Wang, Y. X. Engineering light-controllable CAR T cells for cancer immunotherapy. *Sci. Adv.* 2020, eaay9209

Supplementary Methods

Plasmid Construction

Primers and protein coding sequence (CDSs) for plasmid construction were synthesized by Integrated DNA Technologies (IDT) or amplified from other plasmids. CDSs, non-commercial plasmid sequences, and subcloning insertion sites are listed in Table 7. The subcloning was performed using a Gibson assembly protocol recently described.

TABLE 7

Protein coding sequences (CDSs) and
noncommercial vector used in this work.

| Purpose | Name | CDS or vector sequence | Subcloning note |
|---------|------|------------------------|-----------------|
| *E. coli* expression | DrBp hP-Avi-His | ATGAGTCGTGACCCTTTGCCATTCTTTCCTCCTCTTTATC TGGGTGGACCCGAGATTACAACAGAAAACTGCGAACGCGA ACCAATTCACATCCCGGGATCTATTCAACCACACGGTGCA TTGCTGACGGCAGACGGACATTCCGGAGAGGTTTTACAGA TGTCGCTTAACGCAGCAACGTTTCTGGGACAAGAGCCTAC GGTTTTGCGCGGCCAGACGTTAGCGGCTCTGTTGCCAGAG CAATGGCCGGCCTTACAGGCGGCATTGCCTCCAGGGTGCC CCGATGCATTGCAATACCGCGCGACACTGGATTGGCCGGC GGCAGGACATCTTTCTCTGACAGTCCACCGCGTGGGCGAG CTGTTGATCCTGGAGTTTGAACCTACGGAGGCCTGGGACT CGACTGGCCCGCACGCGTTACGCAATGCGATGTTCGCTCT TGAATCAGCGCCAAACTTGCGCGCGTTAGCTGAAGTGGCC ACACAAACCGTACGCGAGCTTACAGGCTTTGACCGCGTGA TGTTATACAAATTCGCACCCGATGCGACAGGCGAGGTAAT CGCCGAAGCCCGCCGCGAGGGGTTGCATGCCTTTCTTGGC CATCGTTTTCCGGCCTCAGATATTCCCGCCCAAGCGCGCG CCCTTTACACTCGCCATCTGCTTCGTTTGACTGCGGACAC GCGCGCGGCGGCCGTTCCCTTAGACCCAGTACTTAATCCT CAGACTAACGCTCCTACCCCCTTAGGGGGGGCAGTGCTGC GTGCGACGTCGCCTATGCACATGCAGTACCTTCGCAATAT GGGCGTCGGCTCCTCTTTAAGTGTATCAGTGGTAGTTGGG GGGCAGTTATGGGGTCTGATTGCGTGCCATCATCAGACCC CCTATGTTTTGCCACCAGACCTTCGTACTACTCTTGAATA CTTGGGGCGTTTATTAAGCCTTCAGGTGCAAGTCAAGGAA GCCGCGGACGTTGCTGCATTCCGTCAGTCACTTCGCGAAC ACCATGCGCGCGTCGCCTTAGCGGCAGCGCATTCCCTGTC GCCGCACGATACTCTTTCCGACCCTGCACTTGATCTTCTG GGTCTGATGCGTGCTGGGGGCTTAATCCTGCGTTTTGAAG GTCGTTGGCAGACGTTAGGAGAAGTCCCGCCCGCTCCCGC AGTCGATGCACTGCTTGCATGGCTTGAAACCCAACCAGGG GCGCTTGTTCAGACTGATGCATTGGGGCAGTTGTGGCCGG CGGGGGCTGATTTGGCTCCCTCAGCCGCGGGTCTGCTTGC CATTTCAGTAGGGGAGGGATGGAGTGAGTGCTTGGTTTGG TTACGTCCCGAACTGCGCCTTGAGGTTGCGTGGGGTGGAG CAACTCCAGACCAGGCCAAGGACGACCTGGGCCCTCGTCA CAGTTTCGATACTTACTTAGAAGAGAAGCGTGGGTATGCA | The CDS was inserted into pBAD (Addgene #80341) using BamHI/EcoRI restriction sites. |

TABLE 7-continued

Protein coding sequences (CDSs) and
noncommercial vector used in this work.

| Purpose | Name | CDS or vector sequence | Subcloning note |
|---|---|---|---|
| | | GAACCCTGGCATCCCGGAGAGATTGAGGAAGCTCAGGATT TGCGCGACACTCTTACTGGCGCATTAAAGCTTGGTGGCGG TAGCGAGAATTTGTATTTTCAGGGTGGCGGTGGCAGTAGC TTATCCACCCCGCCGACCCCGAGCACTCCTCCTACCGGTC TGAACGACATCTTCGAGGCTCAGAAAATCGAATGGCACGA ACATCATCACCACCATCAC (SEQ ID NO: 21) | |
| | DrBp hP- His | (DrBphP)-GAATTCCATCATCACCATCACCAT (SEQ ID NO: 22) | The sequence of DrBphP is the same as above. The CDS was inserted into pBAD (Addgene #80341) using BamHI/EcoRI restriction sites. |
| | LDB- 3-His | GAAGTTCAGCTGCAGGCAAGCGGTGGTGGTTTTGTTCAGC CTGGTGGTAGCCTGCGTCTGAGCTGTGCAGCCAGCGGTTT TACCTGGGATCATTACATCATGGGCTGGTTTCGCCAGGCA CCGGGTAAAGAACGTGAATTTGTTAGCGCAATCAGCGAAA ATGGTGATGCATGGAATTATTATGCCGATAGCGTGAAAGG TCGCTTTACCATTAGCCGTGATAATAGCAAAAATACCGTT TACCTGCAGATGAATAGTCTGCGTGCAGAAGATACCGCAA CCTATTATTGTGCAATCGGTTTTGATGTTCCATCTGGTCG TTCTTGGCAGGGTTCTCATTTTTGGATGTATTGGGGTCAG GGCACCCAGGTTACCGTTAGCAGCAGCCCGGGAGGCCAAC ACCATCACCACCATCAT (SEQ ID NO: 23) | The CDS was inserted into pADL-23c (Antibody Design Labs) using a BgII restriction site. |
| | LDB- 3-Avi- His | (LDB-3)- AGCCCGGGAGGCCAAAGCTTATCCACCCCGAGTGTAGATC TCGGTGGTCGCCGTATCATTGGTCTGAACGACATCTTCGA GGCTCAGAAAATCGAATGGCACGAACATCATCACCACCAT CACTCT (SEQ ID NO: 24) | The sequence of LDB-3 is the same as above. The CDS was inserted into pADL-23c using a BgII restriction site. |
| | LDB- 14- His | GAAGTTCAGCTGCAGGCAAGCGGTGGTGGTTTTGTTCAGC CTGGTGGTAGCCTGCGTCTGAGCTGTGCAGCCAGCGGTAC CACCTCTCGTTGGGAATCTATGGGCTGGTTTCGCCAGGCA CCGGGTAAAGAACGTGAATTTGTTAGCGCAATCAGCTGGC AGAATAATTCTGTTCCATATTATGCCGATAGCGTGAAAGG TCGCTTTACCATTAGCCGTGATAATAGCAAAAATACCGTT TACCTGCAGATGAATAGTCTGCGTGCAGAAGATACCGCAA CCTATTATTGTGCAGCACAGCATAACTTTCTGGGTCATCG TTATTGGGGTCAGGGCACCCAGGTTACCGTTAGCAGCAGC CCGGGAGGCCAACACCATCACCACCATCAT (SEQ ID NO: 25) | The CDS was inserted into pADL-23c using a BgII restriction site. |
| | LDB- 14- Avi- His | (LDB-14)- AGCCCGGGAGGCCAAAGCTTATCCACCCCGAGTGTAGATC TCGGTGGTCGCCGTATCATTGGTCTGAACGACATCTTCGA GGCTCAGAAAATCGAATGGCACGAACATCATCACCACCAT CACTCT (SEQ ID NO: 26) | The sequence of LDB-14 is the same as above. The CDS was inserted into pADL-23c using a BgII restriction site. |
| Yeast two- hybrid | GAL4- DrBp hP | ATGAAGCTACTGTCTTCTATCGAACAAGCATGCGATATTT GCCGACTTAAAAAGCTCAAGTGCTCCAAAGAAAAACCGAA GTGCGCCAAGTGTCTGAAGAACAACTGGGAGTGTCGCTAC TCTCCCAAAACCAAAAGGTCTCCGCTGACTAGGGCACATC TGACAGAAGTGGAATCAAGGCTAGAAAGACTGGAACAGCT ATTTCTACTGATTTTTCCTCGAGkAGACCTTGACATGATT TTGAAAATGGATTCTTTACAGGATATAAAAGCATTGTTAA CAGGATTATTTGTACAAGATAATGTGAATAAAGATGCCGT CACAGATAGATTGGCTTCAGTGGGAGACTGATATGCCTCTA ACATTGAGACAGCATAGAATAAGTGCGACATCATCATCGG AAGAGAGTAGTAACAAAGGTCAAAGACAGTTGACTGTATC GCCGGAATTTGTAATACGACTCACTATAGGGCGAGCCGCC ATCATGGAGGAGCAGAAGCTGATCTCAGAGGAGGACCTGC AT-(DrBphP) (SEQ ID NO: 27) | The sequence of DrBphP is the same as above. The CDS was inserted into pGBKT7 vector (Clontech) using NdeI/BamHI restriction sites. |

TABLE 7-continued

Protein coding sequences (CDSs) and
noncommercial vector used in this work.

| Purpose | Name | CDS or vector sequence | Subcloning note |
|---|---|---|---|
| | AD-<br>LDB-<br>3 | ATGGATAAAGCGGAATTAATTCCCGAGCCTCCAAAAAAGA<br>AGAGAAAGGTCGAATTGGGTACCGCCGCCAATTTTAATCA<br>AAGTGGGAATATTGCTGATAGCTCATTGTCCTTCACTTTC<br>ACTAACAGTAGCAACGGTCCGAACCTCATAACAACTCAAA<br>CAAATTCTCAAGCGCTTTCACAACCAATTGCCTCCTCTAA<br>CGTTCATGATAACTTCATGAATAATGAAATCACGGCTAGT<br>AAAATTGATGATGGTAATAATTCAAAACCACTGTCACCTG<br>GTTGGACGGACCAAACTGCGTATAACGCGTTTGGAATCAC<br>TACAGGGATGTTTAATACCACTACAATGGATGATGTATAT<br>AACTATCTATTCGATGATGAAGATACCCCACCAAACCCAA<br>AAAAAGAGATCTTTAATACGACTCACTATAGGGCGAGCGC<br>CGCCATGGAGTACCCATACGACGTACCAGATTACGCTCAT<br>ATGGGAGGCGGTTCCGGTGGCGGTTCT-(LDB-3) (SEQ<br>ID NO: 28) | The sequence<br>of LDB-3 is the<br>same as above.<br>The CDS was<br>inserted into<br>pGADT7<br>(Clontech)<br>using<br>NdeI/BamHI<br>restriction sites. |
| | AD-<br>LDB-<br>4 | (AD)-<br>ATCTTTAATACGACTCACTATAGGGCGAGCGCCGCCATGG<br>AGTACCCATACGACGTACCAGATTACGCTCATATGGGAGG<br>CGGTTCCGGTGGCGGTTCTGAAGTTCAGCTGCAGGCAAGC<br>GGTGGTGGTTTTGTTCAGCCTGGTGGTAGCCTGCGTCTGA<br>GCTGTGCAGCCAGCGGTGATACCTCTTACCTGTACTCTAT<br>GGGCTGGTTTCGCCAGGCACCGGGTAAAGAACGTGAATTT<br>GTTAGCGCAATCAGCTGGTGGTGGAATCTGACTCAGTATT<br>ATGCCGATAGCGTGAAAGGTCGCTTTACCATTAGCCGTGA<br>TAATAGCAAAAATACCGTTTACCTGCAGATGAATAGTCTG<br>CGTGCAGAAGATACCGCAACCTATTATTGTGCATGGTCTA<br>TCTACTTTCCACCAGGTAACGATTACAACGGTTACCATTA<br>TTGGGGTCAGGGCACCCAGGTTACCGTTAGCAGC(SEQ<br>ID NO: 29) | The CDS was<br>inserted into<br>pGADT7 using<br>NdeI/BamHI<br>restriction sites.<br>The sequences<br>of AD and LDB-<br>14 are the same<br>as above. |
| | AD-<br>LDB-<br>6 | (AD)-<br>ATCTTTAATACGACTCACTATAGGGCGAGCGCCGCCATGG<br>AGTACCCATACGACGTACCAGATTACGCTCATATGGGAGG<br>CGGTTCCGGTGGCGGTTCTGAAGTTCAGCTGCAGGCAAGC<br>GGTGGTGGTTTTGTTCAGCCTGGTGGTAGCCTGCGTCTGA<br>GCTGTGCAGCCAGCGGTTTTTTTTTCTAACTGGTCTGATAT<br>GGGCTGGTTTCGCCAGGCACCGGGTAAAGAACGTGAATTT<br>GTTAGCGCAATCAGCTTTTGGGCAGATGGTACTGAATATT<br>ATGCCGATAGCGTGAAAGGTCGCTTTACCATTAGCCGTGA<br>TAATAGCAAAAATACCGTTTACCTGCAGATGAATAGTCTG<br>CGTGCAGAAGATACCGCAACCTATTATTGTGCATGGTACG<br>GTCCAGTTAACGGTTTTTACATGTTTGATTATTGGGGTCA<br>GGGCACCCAGGTTACCGTTAGCAGC(SEQ ID NO: 30) | |
| | AD-<br>LDB-<br>7 | (AD)-<br>ATCTTTAATACGACTCACTATAGGGCGAGCGCCGCCATGG<br>AGTACCCATACGACGTACCAGATTACGCTCATATGGGAGG<br>CGGTTCCGGTGGCGGTTCTGAAGTTCAGCTGCAGGCAAGC<br>GGTGGTGGTTTTGTTCAGCCTGGTGGTAGCCTGCGTCTGA<br>GCTGTGCAGCCAGCGGTTCTACCTCTGATTTTGAATCTAT<br>GGGCTGGTTTCGCCAGGCACCGGGTAAAGAACGTGAATTT<br>GTTAGCGCAATCAGCTCTTGGTTTACTAATCCACCATATT<br>ATGCCGATAGCGTGAAAGGTCGCTTTACCATTAGCCGTGA<br>TAATAGCAAAAATACCGTTTACCTGCAGATGAATAGTCTG<br>CGTGCAGAAGATACCGCAACCTATTATTGTGCACATCGTT<br>CTATCTGGTACCATCCAACCTATTGGGGTCAGGGCACCCA<br>GGTTACCGTTAGCAGC(SEQ ID NO: 31) | |
| | AD-<br>LDB-<br>14 | (AD)-<br>ATCTTTAATACGACTCACTATAGGGCGAGCGCCGCCATGG<br>AGTACCCATACGACGTACCAGATTACGCTCATATGGGAGG<br>CGGTTCCGGTGGCGGTTCT-(LDB-14) (SEQ ID NO:<br>32) | |

TABLE 7-continued

Protein coding sequences (CDSs) and
noncommercial vector used in this work.

| Purpose | Name | CDS or vector sequence | Subcloning note |
|---|---|---|---|
| Mammalian two-hybrid | GAL4 DrBp hP | GAL4-DrBphP | The sequence ofGAL4-DrBphP is the same as above. The CDS was inserted into pBobi (see below for the sequence) using BamHI/XhoI restriction sites. |
| | NLS-LDB-3-p65 | ATGGGATCCCCCAAGAAGAAGCGCAAGGTGGAAGCTAGCG CTTCCCCGAAGAAAAAGCGGAAAGTCGAGGCCTCCGCATC TCCAAAAAAAAAAAAGCAAGGTTGAAGCATCTGGATCCGGT ACCGGAGGAAGTGGCAGCTCTGGCGGCAGTGGAGGGTCTG GTGGCAGCGGA-(LDB-3)- AGCGGCGGCGGTGGCAGTCAGTACCTGCCAGATACAGACG ATCGTCACCGGATTGAGGAGAAACGTAAAAGGACATATGA GACCTTCAAGAGCATCATGAAGAAGAGTCCTTTCAGCGGA CCCACCGACCCCCGGCCTCCACCTCGACGCATTGCTGTGC CTTCCCGCAGCTCAGCTTCTGTCCCCAAGCCAGCACCCCA GCCCTATCCCTTTACGTCATCCCTGAGCACCATCAACTAT GATGAGTTTCCCACCATGGTGTTTCCTTCTGGGCAGATCA GCCAGGCCTCGGCCTTGGCCCCGGCCCCTCCCCAAGTCCT GCCCCAGGCTCCAGCCCCTGCCCCTGCTCCAGCCATGGTA TCAGCTCTGGCCCAGGCCCCAGCCCCTGTCCCAGTCCTAG CCCCAGGCCCTCCTCAGGCTGTGGCCCCACCTGCCCCCAA GCCCACCCAGGCTGGGGAAGGAACGCTGTCAGAGGCCCTG CTGCAGCTGCAGTTTGATGATGAAGACCTGGGGGCCTTGC TTGGCAACAGCACAGACCCAGCTGTGTTCACAGACCTGGC ATCCGTCGACAACTCCGAGTTTCAGCAGCTGCTGAACCAG GGCATACCTGTGGCCCCCCACACAACTGAGCCCATGCTGA TGGAGTACCCTGAGGCTATAACTCGCCTAGTGACAGGGGC CCAGAGGCCCCCCGACCCAGCTCCTGCTCCACTGGGGGCC CCGGGGCTCCCCAATGGCCTCCTTTCAGGAGATGAAGACT TCTCCTCCATTGCGGACATGGACTTCTCAGCCCTGCTGAG TCAGATCAGCTCC(SEQ ID NO: 33) | The CDS was inserted into pBobi vector using BamHI/XhoI restriction sites. The sequence of LDB-3 is the same as above. |
| | NLS-LDB-4-p65 | (NLS)- GGATCCGGTACCGGAGGAAGTGGCAGCTCTGGCGGCAGTG GAGGGTCTGGTGGCAGCGGA-(LDB-4)- AGCGGCGGCGGTGGCAGT-(p65) (SEQ ID NO: 34) | The sequences of NLS, nanobody and p65 are the same as above. The CDS was inserted into pBobi using BamHI/XhoI restriction sites. |
| | NLS-LDB-6-p65 | (NLS)- GGATCCGGTACCGGAGGAAGTGGCAGCTCTGGCGGCAGTG GAGGGTCTGGTGGCAGCGGA-(LDB-6)- AGCGGCGGCGGTGGCAGT-(p65) (SEQ ID NO: 35) | |
| | NLS-LDB-7-p65 | (NLS)- GGATCCGGTACCGGAGGAAGTGGCAGCTCTGGCGGCAGTG GAGGGTCTGGTGGCAGCGGA-(LDB-7)- AGCGGCGGCGGTGGCAGT-(p65) (SEQ ID NO: 36) | |
| | NLS-LDB-14-p65 | ATGCCCAAGAAGAAGCGCAAGGTGGAAGCTAGCGCTTCCC CGAAGAAAAAGCGGAAAGTCGAGGCCTCCGCATCTCCAAA AAAAAAAGCAAGGTTGAAGCATCTGGATCCGGAGGCGGT TCCGGTGGCGGTTCT-(LDB-14)- GGTACCGGAGGAAGTGGCAGCTCTGGCGGCAGTGGAGGGT CTGGTGGCAGCGGA-(p65)- GGAGGAAGTGGCAGCTCTGGCGGCAGTGGA(SEQ ID NO: 37) | The CDS was inserted into pcDNA3 (Invitrogen) using HindIII/XhoI restriction sites. The sequences of LDB-14 and p65 are the same as above. |

TABLE 7-continued

Protein coding sequences (CDSs) and
noncommercial vector used in this work.

| Purpose | Name | CDS or vector sequence | Subcloning note |
|---|---|---|---|
| | GAL4 RpBp hP1 | (GAL4)-<br>CCGGAATTTGTAATACGACTCACTATAGGGCGAGCCGCCA<br>TCATGGAGGAGCAGAAGCTGATCTCAGAGGAGGACCTGCA<br>TGTGGCAGGTCATGCCTCTGGCAGCCCCGCATTCGGGACC<br>GCCGATCTTTCGAATTGCGAACGTGAAGAGATCCACCTCG<br>CCGGCTCGATCCAGCCGCATGGCGCGCTTCTGGTCGTCAG<br>CGAGCCGGATCATCGCATCATCCAGGCGCAGCGCCAACGCC<br>GCGGAATTTCTGAATCTCGGAAGCGTGCTCGGCGTTCCGC<br>TCGCCGAGATCGACGGCGATCTGTTGATCAAGATCCTGCC<br>GCATCTCGATCCCACCGCCGAAGGCATGCCGGTCGCGGTG<br>CGCTGCCGGATCGGCAATCCCTCCACGGAGTACGACGGTC<br>TGATGCATCGGCCTCCGGAAGGCGGGCTGATCATCGAGCT<br>CGAACGTGCCGGCCCGCCGATCGATCTGTCCGGCACGCTG<br>GCGCCGGCGCTGGAGCGGATCCGCACGGCGGGCTCGCTGC<br>GCGCGCTGTGCGATGACACCGCGCTGCTGTTTCAGCAGTG<br>CACCGGCTACGACCGGGTGATGGTGTATCGCTTCGACGAG<br>CAGGGCCACGGCGAAGTGTTCTCCGAGCGCCACGTGCCCG<br>GGCTCGAATCCTATTTCGGCAACCGCTATCCGTCGTCGGA<br>CATTCCGCAGATGGCGCGGCGGCTGTACGAGCGGCAGCGC<br>GTCCGCGTGCTGGTCGACGTCAGCTATCAGCCGGTGCCGC<br>TGGAGCCGCGGCTGTCGCCGCTGACCGGGCGCGATCTCGA<br>CATGTCGGGCTGCTTCCTGCGCTCGATGTCGCCGATCCAT<br>CTGCAGTACCTGAAGAACATGGGCGTGCGCGCCACCCTGG<br>TGGTGTCGCTGGTGGTCGGCGGCAAGCTGTGGGGCCTGGT<br>TGCCTGTCACCATTATCTGCCGCGCTTCATCCATTTCGAG<br>CTGCGGGCGATCTGCGAACTGCTCGCCGAAGCGATCGCGA<br>CGCGGATCACCGCGCTTGAGAGCTTCGCGCAGAGCCAGTC<br>GGAGCTGTTCGTGCAGCGGCTCGAACAGCGCATGATCGAA<br>GCGATCACCCGTGAAGGCGATTGGCGCGCAGCGATTTTCG<br>ACACCAGCCAATCGATCCTGCAGCCGCTGCACGCCGACGG<br>TTGCGCGCTGGTGTACGAAGACCAGATCAGGACCATCGGT<br>GACGTACCTTCCACGCAGGATGTTCGCGAGATCGCCGGGT<br>GGCTCGATCGCCAGCCACGTGCGGCGGTGACCTCGACCGC<br>GTCGCTCGGTCTCGACGTGCCGGAGCTCGCGCATCTGACG<br>CGGATGGCGAGCGGCGTGGTCGCGGCGCCGATTTCGGATC<br>ATCGCGGCGAGTTTCTGATGTGGTTCCGCCCCGAGCGCGT<br>CCACACCGTTACCTGGGGCGGCGATCCGAAGAAGCCGTTC<br>ACGATGGGCGATACACCGGCGGATCTGTCGCCGCGGCGCT<br>CCTTCGCCAAATGGCATCAGGTTGTCGAAGGCACGTCCGA<br>TCCGTGGACGGCCGCCGATCTCGCCGCGGCTCGCACCATC<br>GGTCAGACCGTCGCCGACATCGTGCTGCAATTCCGCGCGG<br>TGCGGACACTGATCGCCCGCGAACAGTACGAACAGTTTTC<br>GTCCCAGGTGCACGCTTCGATGCAGCCGGTGCTGATCACC<br>GACGCCGAAGGCCGCATCCTGCTGATGAACGACTCGTTCC<br>GCGACATGTTGCCGGCGGGGTCGCCATCCGCCGTCCATCT<br>CGACGATCTCGCCGGGTTCTTCGTCGAATCGAACGATTTC<br>CTGCGCAACGTCGCCGAACTGATCGATCACGGCCGCGGGT<br>GGCGCGGCGAAGTTCTGCTGCGCGGCGCAGGTAATCGCCC<br>GTTGCCGCTGGCAGTGCGCGCCGATCCGGTGACGCGCACG<br>GAGGACCAGTCGCTCGGCTTCGTGCTGATCTTCAGCGACG<br>CTACCGATCGTCGCACCGCAGATGCCGCACGCACGCGTTT<br>CCAGGAAGGCATTCTTGCCAGCGCACGTCCCGGCGTGCGG<br>CTCGACTCCAAGTCCGACCTCTTGCACGAGAAGCTGCTGT<br>CCGCGCTGGTCGAGAACGCGCAGCTTGCCGCATTGGAAAT<br>TACTTACGGCGTCGAGACCGGACGCATCGCCGAGCTGCTC<br>GAAGGCGTTCGCCAGTCGATGCTGCGCACCGCCGAAGTGC<br>TCGGCCATCTGGTGCAGCACGCGGCGCGCACGGCCGGCAG<br>CGACAGCTCGAGCAATGGCTCGCAGAACAAGAAG<br>(SEQ ID NO: 38) | The CDS was subcloned into pcDNA3 using HindIII/XhoI restriction sites. The sequence ofGAL4 is the same as above. |
| | NLS-<br>PpsR<br>2-p65 | ATGCCCAAGAAGAAGCGCAAGGTGGAAGCTAGCGCTTCCC<br>CGAAGAAAAAGCGGAAAGTCGAGGCCTCCGCATCTCCAAA<br>AAAAAAAAGCAAGGTTGAAGCATCTGGATCCGGAGGCGGT<br>TCCGGTGGCGGTTCTGTGGCGTCAAAGTCCGTTCATGCCG<br>ACATCACCCTTCTGCTCGATATGGAGGGTGTGATTCGCGA<br>AGCCACCCTGTCTCCGACGATGGCGGCCGAGAGCGTGGAC<br>GGTTGGCTGGGGCGTCGCTGGAGCGACATCGCCGGCGCCG<br>AAGGCGGCGACAAGGTTCGCCGCATGGTCGAAGACGCCCG<br>CCCGCAGCGGCATCTCGGCTTTCCGCCAGATCAATCAGCCT<br>TTCCCGAGCGGCGTCGAAATCCCGATCGAATTCACCACGA<br>TGCTGCTGGGCGACCGCACCGGCATGATCGCGGTCGGCAA<br>GAACATGCAGGCGGTCACCGAGCTGCATTCCCGGCTGATC<br>GCTGCGCAGCAGGCGATGGAGCGCGACTATTGGCGGTTGC<br>GTGAATTGGAGACTCGCTACCGCCTGGTGTTCGACGCTGC | The CDSs were inserted into pcDNA3 using HindIII/XhoI restriction sites. The sequence of p65 is the same as above. |

TABLE 7-continued

Protein coding sequences (CDSs) and
noncommercial vector used in this work.

| Purpose | Name | CDS or vector sequence | Subcloning note |
|---|---|---|---|
| | | CGCCGATGCGGTGATGATCGTCTCCGCCGGCGACATGCGC ATCGTCGAAGCCAACCGGGCGGCGGTGAATGCGATCAGCC GCGTCGAGCGCGGCAATGACGACCTTGCGGGGCGTGATTT CCTCGCCGAAGTGGCGGCTGCCGATCGCGATGCGGTGCGC GACATGCTGGCCCAGGTGCGTCAGCGCGGCACCGCACTCA GCGTCCTCGTTCATCTCGGCCGTTACGACCGCGCCTGGAT GCTGCGCGGTTCGCTGATGTCGTCCGAGCGTCGTCAGGTT TTCCTGCTGCACTTCACCCCGGTGACCACGACTCCCGCGA TCGACGACGTCGACGATGATGCCGTGCTGCGCGGGCTGAT CGATCGCATTCCCGACGGGTTCGTCGCACTGGATTCGGAA GGCGTCGTTCGTCACGCCAACCAGGCGTTTCTCGATCTGG TCCAGATCGGCTCCAAGCCTGCGGCGGTCGGACGATCGCT GGGCGTCTGGATGGGTCGTCCGGGCGCCGATCTGTCCAGC TTGCTGACGCTGCTGCGGCGCTACAAGACGGTGCGGCTGT TCCAAACGACGATCCGCGGCGAGCTCGGCACCGAGACTGA AGTCGAGGTCTCGGCCGTCGACGGCGAGGACGACCAATAC ATCGGCGTTCTGATGCGCAATGTCGCGCGACGCCTCGACG CTGCGGACGACCACGATGCCTTGCGTCAGGCGCTCGGCCC GATCAGCAAGCAGCTCGGGCGATCCTCGCTGCGCAAGCTG GTGAAGAACGCCGTGAGCATTGTCGAGCAGCACTACGTGA AGGAAGCGCTGTTGCGATCCAAGGGCAATCGCACGGCAAC TGCCGAACTGCTCGGATTGAGCCGGCAGAGCCTTTATGCA AAACTCAACTCCTACGGCTTCGACGACAAAGGTGTCGTTG CTTCTGCTGCCGACGGTGCAGAGGGCGCCTCAGACGACGC AGAGGATGGTACCGGAGGAAGTGGCAGCTCTGGCGGCAGT GGAGGGTCTGGTGGCAGCGGA-(p65)- GGAGGAAGTGGCAGCTCTGGCGGCAGTGGA (SEQ ID NO: 39) | |
| | NLS- Q- PAS1 -p65 | ATGCCCAAGAAGAAGCGCAAGGTGGAAGCTAGCGCTTCCC CGAAGAAAAAGCGGAAAGTCGAGGCCTCCGCATCTCCAAA AAAAAAAGCAAGGTTGAAGCATCTGGATCCGGAGGCGGT TCCGGTGGCGGTTCTGGCAAGAACATGCAGGCGGTCACCG AGCTGCATTCCCGGCTGATCGCTGCGCAGCAGGCGATGGA GCGCGACTATTGGCGGTTGCGTGAATTGGAGACTCGCTAC CGCCTGGTGTTCGACGCTGCCGCCGATGCGGTGATGATCG TCTCCGCCGGCGACATGCGCATCGTCGAAGCCAACCGGGC GGCGGTGAATGCGATCAGCCGCGTCGAGCGCGGCAATGAC GACCTTGCGGGGCGTGATTTCCTCGCCGAAGTGGCGGCTG CCGATCGCGATGCGGTGCGCGACATGCTGGCCCAGGTGCG TCAGCGCGGCACCGCACTCAGCGTCCTCGTTCATCTCGGC CGTTACGACCGCGCCTGGATGCTGCGCGGTTCGCTGATGT CGTCCGAGCGTCGTCAGGTTTTCCTGCTGCACTTCACCCC GGTGACCACGACTCCCGCGATCGACGACGGTACCGGAGGA AGTGGCAGCTCTGGCGGCAGTGGAGGGTCTGGTGGCAGCG GA-(p65)-GGAGGAAGTGGCAGCTCTGGCGGCAGTGGA (SEQ ID NO: 40) | |
| Detection of nanobody expression in mammalian cells | LDB- 3- SNA P | ATGGGGATCC-(LDB-3)- GTTAACGGCGGCGGTGGCAGTGACAAAGACTGCGAAATGA AGCGCACCACCCTGGATAGCCCTCTGGGCAAGCTGGAACT GTCTGGGTGCGAACAGGGCCTGCACCGTATCATCTTCCTG GGCAAAGGAACATCTGCCGCCGACGCCGTGGAAGTGCCTG CCCCAGCCGCCGTGCTGGGCGGACCAGAGCCACTGATGCA GGCCACCGCCTGGCTCAACGCCTACTTTCACCAGCCTGAG GCCATCGAGGAGTTCCCTGTGCCAGCCCTGCACCACCCAG TGTTCCAGCAGGAGAGCTTTACCCGCCAGGTGCTGTGGAA ACTGCTGAAAGTGGTGAAGTTCGGAGAGGTCATCAGCTAC AGCCACCTGGCCGCCCTGGCCGGCAATCCCGCCGCCACCG CCGCCGTGAAAACCGCCCTGAGCGGAAATCCCGTGCCCAT TCTGATCCCCTGCCACCGGGTGGTGCAGGGCGACCTGGAC GTGGGGGGCTACGAGGGCGGGCTCGCCGTGAAAGAGTGGC TGCTGGCCCACGAGGGCCACAGACTGGGCAAGCCTGGGCT GGGT (SEQ ID NO: 41) | The CDS was inserted into pBobi vector using BamHI/XhoI restriction sites. The sequence of LDB-3 is the same as above. |

TABLE 7-continued

Protein coding sequences (CDSs) and
noncommercial vector used in this work.

| Purpose | Name | CDS or vector sequence | Subcloning note |
|---|---|---|---|
| | LDB-4-SNAP | ATGGGATCC-(LDB-4)-GTTAACGGCGGCGGTGGCAGT-(SNAP) (SEQ ID NO: 42) | The CDSs were inserted into pBobi using BamHI/XhoI restriction sites. The sequences of nanobodies and SNAP are the same as above. |
| | LDB-6-SNAP | ATGGGATCC-(LDB-6)-GTTAACGGCGGCGGTGGCAGT-(SNAP) (SEQ ID NO: 43) | |
| | LDB-7-SNAP | ATGGGATCC-(LDB-7)-GTTAACGGCGGCGGTGGCAGT-(SNAP) (SEQ ID NO: 44) | |
| | LDB-14-SNAP | ATGGGATCC-(LDB-14)-GTTAACGGCGGCGGTGGCAGT-(SNAP) (SEQ ID NO: 45) | |

Protein Expression and Purification

DrBphP-Avi-His and DrBphP-His were expressed in *Escherichia coli* and purified by Ni-affinity and size-exclusion chromatography. In brief, *Escherichia coli* C41 (DE3) cells (Lucigen) were transformed with a DrBphP-Avi-His or DrBphP-His expression construct and grown in 2×YT medium at 37° C. to an $OD_{600}$ of ~0.6 before induction with 0.1% arabinose at 25° C. for overnight. Harvested cell pellets from 1-liter cultures were resuspended in 40 mL ice-cold lysis buffer (50 mM sodium phosphate, pH 8.0, 300 mM NaCl, 10 mM imidazole, 10% glycerol) for sonication. The supernatant after centrifugation at 15,000×g, 4° C. for 30 min was loaded onto a 5 mL HisTrap™ column (GE Healthcare) pre-equilibrated with the lysis buffer. The column was washed with a washing buffer (50 mM sodium phosphate, pH 8.0, 300 mM NaCl, 20 mM imidazole, 10% glycerol) and then His-tagged DrBphP was eluted with an elution buffer (50 mM sodium phosphate, pH 8.0, 300 mM NaCl, 500 mM imidazole, 10% glycerol). Eluates were desalted with a HiPrep™ 26/10 column (GE Healthcare) pre-equilibrated with a storage buffer (1×PBS, 5% glycerol). Fractions were pooled and incubated with biliverdin (Frontier Scientific) with molar ratio of 1:20 at 4° C. overnight and then loaded onto a HiPrep™ 26/10 desalting column (GE Healthcare) pre-equilibrated with a storage buffer (1×PBS, 5% glycerol). Eluates were concentrated with Amicon Ultra-15 centrifugal filter units (30 kDa cutoff; Millipore). Concentrated proteins were loaded onto a HiLoad™ 16/600 Superdex 200 µg column (GE Healthcare) pre-equilibrated with a storage buffer (1×PBS, 5% glycerol). Eluted proteins were concentrated, examined by SDS-PAGE, and quantified by a Bradford assay (BioRad), then flash frozen by liquid $N_2$ and stored at −80° C.

His-tagged or Avi-Tagged nanobodies were expressed in *Escherichia coli* strain WK6 and purified by Ni-affinity and size-exclusion chromatography.

Protein Biotinylation

DrBphP-Avi-His was biotinylated by BirA using a BirA-500 kit (Avidity). Typically, 200 µL BiomixA™ (10× concentration: 0.5 M bicine buffer, pH 8.3), 200 µL BiomixB (10× concentration: 100 mM ATP, 100 mM Mg (OAc)$_2$, 500 µM d-biotin), 200 µL BIO200 (10× concentration: 500 µM d-biotin), 20 µL 1 mg/mL BirA, and DrBphP-Avi-His (final concentration at ~2.4 mg/mL) were mixed with $H_2O$ to a final volume of 2 mL. The biotinylation mixture was incubated at 37° C. for 1 h and then loaded onto a HiPrep™ 26/10 desalting column (GE Healthcare) pre-equilibrated with a storage buffer (1×PBS, 5% glycerol). Eluted proteins were concentrated, examined by SDS-PAGE, and quantified by the Bradford assay, flash frozen by liquid $N_2$, and stored at −80° C. LDB-3-Avi-His and LDB-14-Avi-His were biotinylated similarly as DrBphP.

Phage Display Selection

The combinatorial nanobody phage library was prepared as previously described. Dimerization binders were selected using 775-nm and 654-nm illuminations for the negative and positive selections, respectively. Briefly, 1.2 mL 20 µM biotinylated DrBphP-Avi-His was bound to 600 µL streptavidin agarose resin (Thermo Scientific) and blocked with 1% casein and 1% BSA in 1×PBS pH 7.4 for 30 min at 4° C. in the dark. The resins were divided by a 2:1 ratio to pack the negative and positive selection columns (HR 5/5, GE Healthcare), respectively. As shown in FIG. 10, both columns were connected to AKTA FPLC system and equilibrated with ~10 mL PBS buffer at 0.5 mL/min. The negative and positive selection columns were illuminated with 775±14 nm light (FC-LED-780M, Prizmatix) at 0.8 mW/cm$^2$ for 10 min and 654±11 nm light (FC-LED-655A, Prizmatix) at 0.3 mW/cm$^2$ for 10 min and then wrapped with aluminum foil. The light intensity was measured with an optical power meter (PM100D, Thorlabs) connected to a S130C probe (Thorlabs). In each round, phage-displayed nanobodies were loaded onto the columns equilibrated with 1×PBS at a flow rate of 0.04 mL/min. Next, the negative selection column was removed and the positive selection column washed with ~30 mL 0.05% PBST (1×PBS with 0.05% v/v Tween 20) at a flow rate at 0.5 mL/min until the UV 280 nm baseline became stable (i.e., non-bound phages were washed out). Prior to the illumination, 2 mL flow through was collected as a "pre-elution fraction" at 0.5 mL/min immediately. The flow rate was decreased to 0 and then the positive selection column was illuminated with the 775-nm light (0.8 mW/cm$^2$) for a given time (refer to FIG. 10). A 2-mL fraction was collected as a "light-elution fraction" at 0.5 mL/min immediately after the illumination. The percentage of phages specifically eluted by the light was estimated by comparing phage counts in the pre-elution and light-elution fractions. The light eluted phages were amplified and used as an input for next round biopanning.

Y2H Screening

CDSs of the enriched nanobody library after four rounds of the biopanning were subcloned into pGADT7 to create a sub-library as preys. DrBphP was inserted to pGBKT7 as the bait. Y2HGold cells were co-transformed with bait and prey plasmids, plated onto SD/-Ade/-His/-Leu/-Trp plates under the 654-nm illumination (0.03 mW/cm$^2$), and incubated at 30° C. for 4-5 days. ~2,000 well-grown clones were picked and grew in 1-mL SD/-Leu/-Trp medium in deep 96-well plates under the 654-nm illumination (0.03 mW/cm$^2$) for 24 h. 1-μL cells of each clone were replica spotted to SD/-Ade/-His/-Leu/-Trp plates and incubated under the 654-nm illumination (0.03 mW/cm$^2$) or in the dark for 2-3 days. Clones showing significantly faster growth under the illumination were picked for further analysis. Because clones picked from the plates were often contaminated with a small amount of other clones, plasmids were purified from yeast, transformed into an E. coli DH5a strain to select clones carrying pGADT7 on LB Agar plates with Ampicillin (100 μg/mL) and then identify those carrying correct nanobody genes by Sanger sequencing. To further confirm the gene activation specificity, sequenced preys and the bait were again co-transformed into Y2HGold cells; non-diluted and diluted (1/10 and 1/100) cells were spotted onto SD/-Ade/-His/-Leu/-Trp plates to compare colony growth under the illumination and in the dark. Sequence- and specificity-validated clones were chosen for further analyses.

Phage ELISA

E. coli electrocompetent TG1 cells were transformed with pADL-23c inserted with selected nanobody candidates. Colonies were inoculated into 250 μL media (2×TY, 2% glucose, 100 μg/mL ampicillin) in deep 96-well plates and grown at 37° C. for overnight. 10-μL cultures were inoculated into 500 μL fresh media and cells were grown to OD$_{600}$=~0.5 and infected by CM13 helper phage with the multiplicity of infection (MOI) of ~18. Cells were shaken at 37° C. for 45 min, added with kanamycin (50 μg/mL, the final concentration), and grown at 25° C. for overnight. Plates were centrifuged for 30 min at 3,000×g and phage-containing supernatants were transferred to fresh plates for an ELISA assay. Specifically, ELISA plates (Nunc Max-iSorp™, Thermo Fisher Scientific) were coated with 100 μL 5 μg/mL streptavidin in a coating buffer (100 mM carbonate buffer, pH 8.6) at 4° C. for overnight. After washing five times with 0.05% PBST (1×PBS with 0.05% v/v Tween 20), each well was added with 100 μL 2 μM biotinylated DrBphP-Avi-His and incubated at room temperature (r.t.) for 1 h in the dark. Wells were washed five times with 0.05% PBST, blocked with 1% casein in 1× PBS, and then illuminated by the 654-nm (0.3 mW/cm$^2$) or 775-nm (0.2 mW/cm$^2$) light for 10 min. 100 μL phage supernatants were added and incubated at r.t. for 1 h in dark. Wells were washed 10 times with 0.05% PBST and then illuminated with corresponding light (654 nm at 0.3 mW/cm$^2$ or 775 nm at 0.2 mW/cm$^2$) for 10 min before washing five times with 0.05% PBST. Wells were added with 100 μL HRP-M13 major coat protein antibody (RL-ph1, Santa Cruz Biotechnology; 1:10,000 dilution with 1×PBS, 1% casein) and incubated at r.t. for 1 h in the dark. A colorimetric detection was performed using a 1-Step Ultra TMB ELISA substrate solution (Thermo Fisher Scientific); OD$_{450}$ was measured with a SpectraMax™ Plus 384 microplate reader (Molecular Devices).

Mammalian Two-Hybrid Assay

HEK293T cells (ATCC, CRL-3216) were grown in a Dulbecco's modified Eagle's medium (DMEM) supplemented with 10% fetal bovine serum (FBS; Thermo Fisher Scientific) in a humidified incubator (Forma Scientific) under 5% CO$_2$ at 37° C. For a firefly luciferase assay, cells were grown in 24-well plates (Greiner Bio-One) to ~60% confluence and transiently co-transfected with the DrBphP bait and nanobody preys, and a luciferase reporter plasmid (Addgene, #64125) in a 1:1:1 ratio (0.25 μg each into a ~500 μL medium). After the transfection, culture medium was changed in 6 h and then cells were kept in the darkness for another 18 h prior to the transcription activation. The activation was performed by continuously illuminating cells with the 654-nm light at 0.2 mW/cm$^2$ for 24 h; cells were kept in the dark as the control. The time-course luciferase assay was performed as described above with different transcription induction times.

Luciferase levels were measured with a firefly luciferase glow assay kit (Pierce) following the manual. Briefly, after the transcription activation, cells were washed with 1× PBS, added with 150 μl of 1× cell lysis buffer, and incubated at 4° C. for 30 min. 20 μl cell lysate from each well was transferred into a black 96-well plate (CELLSTAR™, Greiner Bio-One, Cat #655079) and mixed with 50 μl of a Working Solution. Bioluminescence signals were measured with a SpectraMax™ i3 plate reader (Molecular Devices) after incubation in the dark at r.t. for 10 min.

The luciferase assay of RpBphP1-based systems was performed under the same condition, except that the transcription activation was performed with the 775-nm (0.2 mW/cm$^2$) illumination, because different from DrBphP, RpBphP1 is converted to the light form by NIR illumination.

Analysis of Nanobody Stability in Mammalian Cells

~2×10$^5$ HEK293T cells were seeded in 6-well plates (Thermo Fisher Scientific, catalog #140675) in DMEM supplemented with 10% FBS, and incubated under 5% CO$_2$ at 37° C. for overnight. Cells in a 1.5-mL medium were transiently transfected with plasmids (2.5 ug each) encoding nanobody-SNAP-tag fusions using lipofectamine 2000 (Thermo Fisher Scientific). After 36-h incubation, the medium was removed and cells were washed with 1x PBS twice, dissociated from the plate by digestion with a 1x Trypsin-EDTA Solution (Thermo Fisher Scientific, catalog #R001100), and collected in 15-mL conical tubes. Cells were washed with 1 mL 1×PBS and re-suspended in 250 μL ice cold 1× PBS for sonication. After centrifugation at 20,000 g for 10 min, ~50 μL supernatants were incubated with 1 μM (final concentration) SNAP™-Surface 649 (New England Biolabs, catalog #S9159S) for 1 h at r.t. to label SNAP™-tagged proteins. Labelled samples were boiled for 10 min at 95° C. in an SDS sample loading buffer before loaded onto an SDS-PAGE gel. The gel was scanned by an Odyssey CLx™ imaging system (Li-cor Biosciences).

Analytical SEC

Interactions of DrBphP with LDB-3 and LDB-14 were analyzed by analytical SEC. Samples were loaded onto a Superdex™ 200 Increase 10/300 GL column (GE Health-care) pre-equilibrated with 1× PBS and eluted at 0.75 mL/min at 4° C. The column was calibrated with molecular weight standards (Bio-Rad, catalog #1511901). Light-sensitive samples were prepared in a dark room and the column and sample syringes were all covered by aluminum foil to avoid light exposure.

To detect the complex formation, DrBphP-His was photoconverted to the dark and light forms by the 775-nm (0.8 mW/cm², 10 min) and 654-nm (0.2 mW/cm², 5 min) illumination, respectively. ~6 µM (final concentration) DrBphP-His was added with ~5 µM (final concentration) LDB-3-His or LDB-14-His and incubated at r.t. for 30 min in the dark before loading a 500 µL mixture onto the column. 500-µL fractions with an elution volume between 8 and 16 mL were collected and proteins in each fraction were precipitated by trichloroacetic acid (TCA) for SDS-PAGE analysis. Briefly, 55 µL 100% TCA was mixed with each fraction and incubated at −20° C. for 30 min. After centrifugation at 20,000× g, 4° C. for 15 min, supernatants were removed, and pellets were washed with 600 µL ice-cold acetone three times and then dried in air. Pellets were resuspended and boiled in the SDS loading buffer and analyzed by SDS-PAGE.

Isothermal Titration Calorimetry

Binding affinities and thermodynamics of LDB-3 and LDB-14 to DrBphP were measured by a MicroCal™ PEAQ-ITC device (Malvern) at 25° C. Specifically, ~210 µL of or 5 µM DrBphP-His was loaded to a sample cell and then illuminated by the 654-nm (0.2 mW/cm², 5 min) or 775-nm (0.8 mW/cm², 15 min) light. ~38 µL 80 µM LDB-3-His and 50 µM LDB-14-His were titrated into 10 and 5 µM DrBphP-His in the cell, respectively, by 19 injections (2 µL each) from a syringe. Background heat transfer caused by the nanobody dilution was measured by conducting a titration of LDB-3-His (80 µM) or LDB-14-His (50 µM) into a 1× PBS buffer alone. Titration of 1× PBS buffer into DrBphP-His (10 µM) was also conducted as the control.

Raw ITC data were analyzed by NITPIC version 1.2.7. To find a suitable range for each injection, cut-off differentials for the injection end was changed to 0.1. The fitting equation for a one-site model is $$y = \frac{L}{1 + e^{-k(x-x_0)}} + b,$$

where y represents the heat of injection, x represents the molar ratio, and b, k, L, xo are related parameters. The integrated data of LDB-3 and LDB-14 titrated to the light form were fitted with the above equation by using a "curve fit" function in the Python-SciPy package, which generated $K_D{}^{app}$ and other thermodynamic parameters in Table 4.

Bio-Layer Interferometry

LDB-3 and LDB-14 binding kinetics were analyzed using an Octet™ RED96 system (ForteBio) and Streptavidin (SA) biosensors. Briefly, 20 µg/mL biotinylated LDB-3-Avi-His or LDB-14-Avi-His was immobilized on SA biosensors in 1×PBS buffer (pH 7.4). A duplicate set of sensors was incubated in the buffer without any protein to measure background binding. All sensors were blocked with a buffer (1×PBS, pH 7.4, 0.05% Tween-20, 0.2% BSA, and 10 ng/mL biocytin) before the binding assay. Serial dilutions of DrBphP-His in an assay buffer (1×PBS, pH 7.4, 0.05% Tween-20, and 0.2% BSA) were illuminated with the 654-nm (0.3 mW cm 2, 5 min) or 775-nm (0.2 mW cm⁻², 10 min) light before binding to the nanobodies. The assay was performed in black 96-well plates with a total working volume of 0.2 mL per well at r.t. Raw data were analyzed by an Octet™ data analysis software V9.0 (ForteBio) using a double-reference-subtraction protocol to subtract signals related to nonspecific binding, background, and signal drift caused by sensor variability.

Apparent dissociation constants ($K_D{}^{app}$s) were calculated by the steady-state analysis and the fitting with a global 1:1 model. The fitting of apparent dissociation rate constant ($K_{off}{}^{app}$) was found to be more reliable (or less DrBphP-His concentration dependent) than the fitting of apparent binding rate constant ($k_{on}{}^{app}$), so only $k_{off}{}^{app}$ was calculated by fitting with the equation, $C=C_0+A(1-e^{-k_{off}t})$, where C represents the level of binding, $C_0$ the binding at the start of dissociation, A an asymptote, and t time. $k_{off}{}^{app}$ for each binding was calculated using the "curve_fit" function in the Python-SciPy package. After obtaining $K_D{}^{app}$ and $k_{off}{}^{app}$, $K_{on}{}^{app}$ was calculated by $$k_{on} = \frac{k_{off}}{K_D}.$$

Of note, compared with the fitting result, the dissociation curves were slightly tailed (FIG. 15), likely due to the contribution from DrBphP dimer dissociation.

DrBphP Photoconversion Analysis

The DrBphP thermal relaxation efficiency was analyzed by absorption spectroscopy. Absorption spectra (500-900 nm) of DrBphP samples were obtained using a Spectra-Max™ Plus 384 microplate reader (Molecular Devices). DrBphP-His was added in a quartz micro cuvette (Yixing Purshee Optical Elements) and then converted to the light or dark form by the 654-nm (0.5 mW/cm², 2 min) or 775-nm (0.3 mW/cm², 10 min) illumination before collecting spectra. To monitor the real-time thermal relaxation to the dark form, ~400 µL 5 µM (final concentration) DrBphP-His samples added with or without 5 µM (final concentration) LDB-3-His or LDB-14-His in the cuvette were first converted to the light form by the 654-nm (0.5 mW/cm²) illumination for 2 min and then immediately relaxed by the 775-nm (0.3 or 0.05 mW/cm²) illumination with different exposure times before collecting spectra. The ratio of $A_{750}/A_{700}$ was normalized to the range (0-1) to monitor the relaxation process.

GFP Imaging

HEK293T cells were seeded in 10 cm Nunclon™ Delta Surface culture dishes (Thermo Scientific) in DMEM supplemented with 10% FBS in the humidified incubator under 5% $CO_2$ at 37° C. They were co-transfected with 10 µg a pGreenFirel-Gal4 lentivector (System Biosciences, catalog #TR017PA-1) and lentivirus-packing plasmids (5 µg each) including PMDL, REV and VSVG by a calcium phosphate transfection method. The medium was changed in 6 h after the transfection and the virus was harvested after incubation for another 72 h. To separate the virus from the medium, the medium was centrifuged at 500×g for 5 min and the supernatant was passing through a Millex-HV filter (0.45 µm, Merck Millipore). 2.5 out of 10 mL filtered virus was used to infect HEK293T cells cultured in another 10 cm dish under 50% confluence, with 10 µg/mL polybrene (Merck Millipore), for 24 h.

Lentivirus-transduced HEK293T cells were seeded in 35 mm glass bottom microwell dishes coated with poly-D-lysine (MatTek, catalog #P35GC-0-10-C) at a density of 1×10⁵ cells per dish. On the second day, cells were transiently co-transfected with the GAL4-BD-DrBphP and nanobody-p65 plasmids (1.25 µg each) using lipofectamine 2000 (Thermo Fisher Scientific) and incubated for overnight. For each nanobody candidate, two dishes were needed for the illumination and the dark control; after the transfection, dishes were immediately covered by aluminum foil to avoid light exposure. On the third day, cells were under the 654-nm (0.2 mW/cm²) illumination or maintained in the dark for another 48 h. Prior to fluorescence imaging, cells were fixed by 4% paraformaldehyde for 10 min and washed with 1× PBS.

GFP images were acquired using a Nikon Ti-E™ automated inverted microscope equipped with a Perfect Focus System, a Nikon 20×/0.75-NA Plan Apo Lambda objective, a linear encoded motorized stage (Nikon Ti-S-ER), and an Andor iXon Ultra 888 EMCCD camera (16-bit dynamic range, 1,024×1,024 array with 13-µm pixels). Cells were illuminated by a SPECTRA X™ LED illuminator (Lumencor) coupled with an excitation filter (448±19 nm) and a filter cube mounted with a dichroic mirror (506 nm) and an emission filter (510±20 nm) (Chroma). Culture dishes were scanned under the GFP and a brightfield channels. Acquired GFP images (dark and light condition) were analyzed by MATLAB for quantifying the fluorescence intensity. Specifically, fluorescence signals in all pixels were subtracted by an average background value (i.e., the median of the pixel intensity distribution in each field-of-view (FOV)) and integrated for each FOV. For each condition, 78 FOVs were sampled for statistical analysis.

Thermodynamic Modeling of Competitive Hetero- and Homo-Dimerization

A simplified thermodynamic model was used to understand the observed transition of heat transfer from heat release to absorption when titrating LDB-3 to the dark-form DrBphP (FIG. 5a). We assume that the dark-form DrBphP-LDB-3 binding and LDB-3 dimerization are competitive (FIG. 7a): $2L\leftrightarrow L_2$, and $L+R\leftrightarrow LR$, where L represents the monomeric LDB-3 and R the dark-form DrBphP. The dissociation constants are $$K_{D1} = \frac{[L]^2}{[L_2]} = \frac{1}{K_{a1}} \text{ and } K_{D2} = \frac{[L][R]}{[LR]} = \frac{1}{K_{a2}},$$

where [L], [L₂], [R], and [LR] are equilibrium concentrations, and $K_{a1}$ and $K_{a2}$ are association constants. The relationships of these concentrations are $[L_T]=[L]+[LR]+2[L_2]$, and $[R_T]=[R]+[LR]$, where $[L_T]$ represents the initial total concentration of LDB-3 and $[R_T]$ represents the initial total concentration of DrBphP. So, the equilibrium dissociation constants can also be expressed as $$K_{D1} = \frac{([L_T]-2[L_2]-[LR])^2}{[L_2]}, \text{ and}$$

$$K_{D2} = \frac{([L_T]-2[L_2]-[LR])([R_T]-[LR])}{[LR]}.$$

[L₂] and [LR] could be determined if [$K_{D1}$], [$K_{D2}$], [$L_T$] and [$R_T$] are known.

The equilibrium dissociation constant is associated with the Gibbs energy of dissociation, $\Delta G_D$, and can be expressed in terms of the enthalpy ($\Delta H_D$) and entropy ($\Delta S_D$) changes in the process: $\Delta G_D=-RT \ln K_D=\Delta H_D-T\Delta S_D$. During the ITC assay, we assume that the whole heat transfer is the sum of $\Delta H_{D1}$ and $\Delta H_{D2}$ which could be calculated by concentration changes of each component using above equations. To simulate a titration process, the dissociation of the LDB-3 homodimer was set to be endothermic ($\Delta H_{D1}>0$) while the formation of the LDB-3-DrBphP complex was exothermic ($\Delta H_{D2}<0$), which is consistent with our experimental results (FIG. 5a and S7). To calculate heat transfer of the whole system, $K_{D2}/K_{D1}$ was set as a variable, and $$\frac{|\Delta H_{D1}|}{|\Delta H_{D2}|}$$

was set to be 1:1, 1:2, or 1:3. Thermographs were generated to show the integration of heat transfer in an titration experiment.

The simulation result showed that the clear transition from the heat release to absorption was found when KD2>>KD1 (e.g., KD2/KD1>100). The LDB-3 dimer is expected to a relatively weak complex because, in the SEC experiment, a large percentage of the dimer was dissociated at the low-µM concentrations (FIG. 13a). Based on our simulation and observed data (FIG. 5a), the dark-form DrBphP-LDB-3 complex (KD2) should be much weaker than the LDB-3 dimer (KD1), 3. It should be noted that this simplified model did not consider DrBphP dimerization and possible binding cooperativity in higher-order complexes. The fitting of the dark form binding data was found to be difficult due to the complexity of protein-protein interactions, so we did not calculate the KDapp. Nevertheless, the ITC experimental data and the modeling supports the low dark activity of LDB-3 observed in other assays.

REFERENCES (1) Xia, Y. Z.; Li, K.; Li, J. J.; Wang, T. Q.; Gu, L. C.; Xun, L. Y., T5 exonuclease-dependent assembly offers a low-cost method for efficient cloning and site-directed mutagenesis. Nucleic Acids Res. 2019, 47.

(2) Kang, S.; Davidsen, K.; Gomez-Castillo, L.; Jiang, H.; Fu, X.; Li, Z.; Liang, Y.; Jahn, M.; Moussa, M.; DiMaio, F.; Gu, L., COMBINES-CID: An efficient method for de novo engineering of highly specific chemically induced protein dimerization systems. J. Am. Chem. Soc. 2019, 141, 10948-10952.

(3) Scheuermann, T. H.; Brautigam, C. A., High-precision, automated integration of multiple isothermal titration calorimetric thermograms: New features of NITPIC. Methods 2015, 76, 87-98.

(4) Takala, H.; Bjorling, A.; Berntsson, O.; Lehtivuori, H.; Niebling, S.; Hoernke, M.; Kosheleva, I.; Henning, R.; Menzel, A.; Ihalainen, J. A.; Westenhoff, S., Signal amplification and transduction in phytochrome photosensors. Nature 2014, 509, 245-248.

(5) Kliebenstein, D. J.; Lim, J. E.; Landry, L. G.; Last, R. L., Arabidopsis UVR8 regulates ultraviolet-B signal transduction and tolerance and contains sequence similarity to human Regulator of Chromatin Condensation 1. Plant Physiol. 2002, 130, 234-243.

(6) Wu, D.; Hu, Q.; Yan, Z.; Chen, W.; Yan, C. Y.; Huang, X.; Zhang, J.; Yang, P. Y.; Deng, H. T.; Wang, J. W.; Deng, X. W.; Shi, Y. G., Structural basis of ultraviolet-B perception by UVR8. Nature 2012, 484, 214-U96.

(7) Chen, D.; Gibson, E. S.; Kennedy, M. J., A light-triggered protein secretion system. J. Cell Biol. 2013, 201, 631-640.

(8) Hirose, Y.; Shimada, T.; Narikawa, R.; Katayama, M.; Ikeuchi, M., Cyanobacteriochrome CcaS is the green light receptor that induces the expression of phycobilisome linker protein. Proc. Natl. Acad. Sci. U.S.A 2008, 105, 9528-9533.

(9) Abe, K.; Miyake, K.; Nakamura, M.; Kojima, K.; Ferri, S.; Ikebukuro, K.; Sode, K., Engineering of a green-light inducible gene expression system in *Synechocystis* sp PCC6803. Microb. Biotechnol. 2014, 7, 177-183.

(10) Blain-Hartung, M.; Rockwell, N. C.; Moreno, M. V.; Martin, S. S.; Gan, F.; Bryant, D. A.; Lagarias, J. C., Cyanobacteriochrome-based photoswitchable adenylyl cyclases (cPACs) for broad spectrum light regulation of cAMP levels in cells. J. Biol. Chem. 2018, 293, 8473-8483.

(11) Song, J. Y.; Cho, H. S.; Cho, J. I.; Jeon, J. S.; Lagarias, J. C.; Park, Y. I., Near-UV cyanobacteriochrome signaling system elicits negative phototaxis in the cyanobacterium *Synechocystis* sp PCC 6803. Proc. Natl. Acad. Sci. U.S.A 2011, 108, 10780-10785.

(12) Ramakrishnan, P.; Tabor, J. J., Repurposing *synechocystis* PCC6803 UirS-UirR as a UV-violet/green photoreversible transcriptional regulatory tool in *E. coli*. ACS Synth. Biol. 2016, 5, 733-740.

(13) Okajima, K.; Yoshihara, S.; Fukushima, Y.; Geng, X. X.; Katayama, M.; Higashi, S.; Watanabe, M.; Sato, S.; Tabata, S.; Shibata, Y.; Itoh, S.; Ikeuchi, M., Biochemical and functional characterization of BLUF-type flavin-binding proteins of two species of cyanobacteria. J. Biochem. 2005, 137, 741-750.

(14) Yuan, H.; Dragnea, V.; Wu, Q.; Gardner, K. H.; Bauer, C. E., Mutational and structural studies of the PixD BLUF output signal that affects light-regulated interactions with PixE. Biochemistry 2011, 50, 6365-6375.

(15) Masuda, S.; Nakatani, Y.; Ren, S. K.; Tanaka, M., Blue light-mediated manipulation of transcription factor activity in vivo. ACS Chem. Biol. 2013, 8, 2649-2653.

(16) Stierl, M.; Stumpf, P.; Udwari, D.; Gueta, R.; Hagedorn, R.; Losi, A.; Gartner, W.; Petereit, L.; Efetova, M.; Schwarzel, M.; Oertner, T. G.; Nagel, G.; Hegemann, P., Light modulation of cellular cAMP by a small bacterial photoactivated adenylyl cyclase, bPAC, of the soil bacterium Beggiatoa. J. Biol. Chem. 2011, 286, 1181-1188.

(17) Lindner, R.; Hartmann, E.; Tarnawski, M.; Winkler, A.; Frey, D.; Reinstein, J.; Meinhart, A.; Schlichting, I., Photoactivation mechanism of a bacterial light-regulated adenylyl cyclase. J. Mol. Biol. 2017, 429, 1336-1351.

(18) Ryu, M. H.; Moskvin, O. V.; Siltberg-Liberles, J.; Gomelsky, M., Natural and engineered photoactivated nucleotidyl cyclases for optogenetic applications. J. Biol. Chem. 2010, 285, 41501-41508.

(19) Salomon, M.; Christie, J. M.; Knieb, E.; Lempert, U.; Briggs, W. R., Photochemical and mutational analysis of the FMN-binding domains of the plant blue light receptor, phototropin. Biochemistry 2000, 39, 9401-9410.

(20) Halavaty, A. S.; Moffat, K., N- and C-terminal flanking regions modulate light-induced signal transduction in the LOV2 domain of the blue light sensor phototropin 1 from *Avena sativa*. Biochemistry 2007, 46, 14001-14009.

(21) Strickland, D.; Moffat, K.; Sosnick, T. R., Light-activated DNA binding in a designed allosteric protein. Proc. Natl. Acad. Sci. U.S.A 2008, 105, 10709-10714.

(22) Losi, A.; Polverini, E.; Quest, B.; Gartner, W., First evidence for phototropin-related blue-light receptors in prokaryotes. Biophys. J. 2002, 82, 2627-2634.

(23) Moglich, A.; Moffat, K., Structural basis for light-dependent signaling in the dimeric LOV domain of the photosensor YtvA. J. Mol. Biol. 2007, 373, 112-126.

(24) Moglich, A.; Ayers, R. A.; Moffat, K., Design and signaling mechanism of light-regulated histidine kinases. J. Mol. Biol. 2009, 385, 1433-1444.

(25) Heintzen, C.; Loros, J. J.; Dunlap, J. C., The PAS protein VIVID defines a clock-associated feedback loop that represses light input, modulates gating, and regulates clock resetting. Cell 2001, 104, 453-464.

(26) Zoltowski, B. D.; Schwerdtfeger, C.; Widom, J.; Loros, J. J.; Bilwes, A. M.; Dunlap, J. C.; Crane, B. R., Conformational switching in the fungal light sensor vivid. Science 2007, 316, 1054-1057.

(27) Wang, X.; Chen, X. J.; Yang, Y., Spatiotemporal control of gene expression by a light-switchable transgene system. Nat. Methods 2012, 9, 266-U64.

(28) Nelson, D. C.; Lasswell, J.; Rogg, L. E.; Cohen, M. A.; Bartel, B., FKF1, a clock-controlled gene that regulates the transition to flowering in *Arabidopsis*. Cell 2000, 101, 331-340.

(29) Nakasako, M.; Zikihara, K.; Matsuoka, D.; Katsura, H.; Tokutomi, S., Structural basis of the LOVI dimerization of *Arabidopsis* phototropins 1 and 2. J. Mol. Biol. 2008, 381, 718-733.

(30) Yazawa, M.; Sadaghiani, A. M.; Hsueh, B.; Dolmetsch, R. E., Induction of protein-protein interactions in live cells using light. Nat. Biotechnol. 2009, 27, 941-U105.

(31) Nash, A. I.; McNulty, R.; Shillito, M. E.; Swartz, T. E.; Bogomolni, R. A.; Luecke, H.; Gardner, K. H., Structural basis of photosensitivity in a bacterial light-oxygen-voltage/helix-turn-helix (LOV-HTH) DNA-binding protein. Proc. Natl. Acad. Sci. U.S.A 2011, 108, 9449-9454.

(32) Motta-Mena, L. B.; Reade, A.; Mallory, M. J.; Glantz, S.; Weiner, O. D.; Lynch, K. W.; Gardner, K. H., An optogenetic gene expression system with rapid activation and deactivation kinetics. Nat. Chem. Biol. 2014, 10, 196-202.

(33) Guo, H. W.; Yang, W. Y.; Mockler, T. C.; Lin, C. T., Regulations of flowering time by *Arabidopsis* photoreceptors. Science 1998, 279, 1360-1363.

(34) Kennedy, M. J.; Hughes, R. M.; Peteya, L. A.; Schwartz, J. W.; Ehlers, M. D.; Tucker, C. L., Rapid blue-light-mediated induction of protein interactions in living cells. Nat. Methods 2010, 7, 973-U48.

(35) Zhou, X. X.; Chung, H. K.; Lam, A. J.; Lin, M. Z., Optical control of protein activity by Ffuorescent protein domains. Science 2012, 338, 810-814.

(36) Mizuno, H.; Mal, T. K.; Walchli, M.; Kikuchi, A.; Fukano, T.; Ando, R.; Jeyakanthan, J.; Taka, J.; Shiro, Y.; Ikura, M.; Miyawaki, A., Light-dependent regulation of structural flexibility in a photochromic fluorescent protein. Proc. Natl. Acad. Sci. U.S.A 2008, 105, 9227-9232.

(37) Baca, M.; Borgstahl, G. E. O.; Boissinot, M.; Burke, P. M.; Williams, D. R.; Slater, K. A.; Getzoff, E. D., Complete chemical structure of photoactive yellow protein: novel thioester-linked 4-hydroxycinnamyl chromophore and photocycle chemistry. Biochemistry 1994, 33, 14369-14377.

(38) Ali, A. M.; Reis, J. M.; Xia, Y.; Rashid, A. J.; Mercaldo, V.; Walters, B. J.; Brechun, K. E.; Borisenko, V.; Josselyn, S. A.; Karanicolas, J.; Woolley, G. A., Optogenetic inhibitor of the transcription factor CREB. Chem. Biol. 2015, 22, 1531-1539.

(39) Scheib, U.; Stehfest, K.; Gee, C. E.; Korschen, H. G.; Fudim, R.; Oertner, T. G.; Hegemann, P., The rhodopsin-

US 12,679,884 B2

43 guanylyl cyclase of the aquatic fungus Blastocladiella *emersonii* enables fast optical control of cGMP signaling. Sci. Signal. 2015, 8.

(40) Kainrath, S.; Stadler, M.; Reichhart, E.; Distel, M.; Janovjak, H., Green-light-induced inactivation of receptor signaling using cobalamin-binding domains. Angew. Chem. Int. Ed. Engl. 2017, 56, 4608-4611.

(41) Kaberniuk, A. A.; Shemetov, A. A.; Verkhusha, V. V., A bacterial phytochrome-based optogenetic system controllable with near-infrared light. Nat. Methods 2016, 13, 591-597.

(42) Bellini, D.; Papiz, M. Z., Structure of a bacteriophytochrome and light-stimulated protomer swapping with a gene repressor. Structure 2012, 20, 1436-1446.

(43) Davis, S. J.; Vener, A. V.; Vierstra, R. D., Bacteriophytochromes: Phytochrome-like photoreceptors from non-photosynthetic eubacteria. Science 1999, 286, 2517-2520.

(44) Shu, X. K.; Royant, A.; Lin, M. Z.; Aguilera, T. A.; Lev-Ram, V.; Steinbach, P. A.; Tsien, R. Y., Mammalian expression of infrared fluorescent proteins engineered from a bacterial phytochrome. Science 2009, 324, 804-807.

(45) Hughes, J.; Lamparter, T.; Mittmann, F.; Hartmann, E.; Gartner, W.; Wilde, A.; Borner, T., A prokaryotic phytochrome. Nature 1997, 386, 663-663.

44

(46) Essen, L. O.; Mailliet, J.; Hughes, J., The structure of a complete phytochrome sensory module in the Pr ground state. Proc. Natl. Acad. Sci. U.S.A 2008, 105, 14709-14714.

(47) Levskaya, A.; Chevalier, A. A.; Tabor, J. J.; Simpson, Z. B.; Lavery, L. A.; Levy, M.; Davidson, E. A.; Scouras, A.; Ellington, A. D.; Marcotte, E. M.; Voigt, C. A., Engineering *Escherichia coli* to see light—These smart bacteria 'photograph' a light pattern as a high-definition chemical image. Nature 2005, 438, 441-442.

(48) Sharrock, R. A.; Quail, P. H., Novel phytochrome sequences in *Arabidopsis thaliana*: structure, evolution, and differential expression of a plant regulatory photoreceptor family. Genes Dev. 1989, 3, 1745-1757.

(49) Burgie, E. S.; Bussell, A. N.; Walker, J. M.; Dubiel, K.; Vierstra, R. D., Crystal structure of the photosensing module from a red/far-red light-absorbing plant phytochrome. Proc. Natl. Acad. Sci. U.S.A 2014, 111, 10179-10184.

(50) Shimizu-Sato, S.; Huq, E.; Tepperman, J. M.; Quail, P. H., A light-switchable gene promoter system. Nat. Biotechnol. 2002, 20, 1041-1044.

We claim:

1. A *Deinococcus radiodurans* bacteriophytochrome (DrBphP) light form-binding single chain antibody, comprising a set of complementarity-determining regions (CDRs) selected from the group consisting of:
    (a) SEQ ID NO:1 (CDR1), SEQ ID NO:2 (CDR2), and SEQ ID NO:3 (CDR3); or
    (b) SEQ ID NO:4 (CDR1), SEQ ID NO:5 (CDR2), and SEQ ID NO:6 (CDR3).

2. The antibody of claim 1, comprising an amino acid sequence at least 40% identical to the amino acid sequence of SEQ ID NO:9 or SEQ ID NO:10.

3. A nucleic acid encoding the antibody of claim 2.

4. An expression vector comprising the nucleic acid of claim 3, operatively linked to a control sequence.

5. A solid support, comprising the antibody of claim 1 bound to the solid support.

6. A nucleic acid encoding the antibody of claim 1.

7. An expression vector comprising the nucleic acid of claim 6, operatively linked to a control sequence.

8. A cell that comprises the expression vector of claim 7.

9. The antibody of claim 1, comprising an amino acid sequence at least 60% identical to the amino acid sequence of SEQ ID NO:9 or SEQ ID NO:10.

10. The antibody of claim 1, comprising an amino acid sequence at least 90% identical to the amino acid sequence of SEQ ID NO:9 or SEQ ID NO: 10.

11. A nucleic acid encoding the antibody of claim 10.

12. An expression vector comprising the nucleic acid of claim 11, operatively linked to a control sequence.

13. The antibody of claim 1, comprising an amino acid sequence at least 80% identical to the amino acid sequence of SEQ ID NO:9.

14. The antibody of claim 1, comprising an amino acid sequence at least 80% identical to the amino acid sequence of SEQ ID NO:10.

15. The antibody of claim 1, comprising an amino acid sequence at least 90% identical to the amino acid sequence of SEQ ID NO:9.

16. The antibody of claim 1, comprising an amino acid sequence at least 90% identical to the amino acid sequence of SEQ ID NO:10.

17. The antibody of claim 1, comprising the amino acid sequence of SEQ ID NO:9.

18. The antibody of claim 1, comprising the amino acid sequence of SEQ ID NO:10.

* * * * *

SEQUENCE LISTING

```
<160> NUMBER OF SEQ ID NOS: 52

<210> SEQ ID NO 1
<211> LENGTH: 7
<212> TYPE: PRT
<213> ORGANISM: Artificial Sequence
<220> FEATURE:
<223> OTHER INFORMATION: Synthetic

<400> SEQUENCE: 1

Phe Thr Trp Asp His Tyr Ile
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic

<400> SEQUENCE: 2

Glu Asn Gly Asp Ala Trp Asn
1               5

<210> SEQ ID NO 3
<211> LENGTH: 18
<212> TYPE: PRT
<213> ORGANISM: Artificial Sequence
<220> FEATURE:
<223> OTHER INFORMATION: Synthetic

<400> SEQUENCE: 3

Ile Gly Phe Asp Val Pro Ser Gly Arg Ser Trp Gln Gly Ser His Phe
1               5                   10                  15

Trp Met

<210> SEQ ID NO 4
<211> LENGTH: 7
<212> TYPE: PRT
<213> ORGANISM: Artificial Sequence
```

```
<220> FEATURE:
<223> OTHER INFORMATION: Synthetic

<400> SEQUENCE: 4

Thr Thr Ser Arg Trp Glu Ser
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic

<400> SEQUENCE: 5

Trp Gln Asn Asn Ser Val Pro
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic

<400> SEQUENCE: 6

Ala Gln His Asn Phe Leu Gly His Arg
1               5

<210> SEQ ID NO 7

<400> SEQUENCE: 7

000

<210> SEQ ID NO 8

<400> SEQUENCE: 8

000

<210> SEQ ID NO 9
<211> LENGTH: 128
<212> TYPE: PRT
<213> ORGANISM: Artificial Sequence
<220> FEATURE:
<223> OTHER INFORMATION: Synthetic

<400> SEQUENCE: 9

Glu Val Gln Leu Gln Ala Ser Gly Gly Gly Phe Val Gln Pro Gly Gly
1               5                   10                  15

Ser Leu Arg Leu Ser Cys Ala Ala Ser Gly Phe Thr Trp Asp His Tyr
                20                  25                  30

Ile Met Gly Trp Phe Arg Gln Ala Pro Gly Lys Glu Arg Glu Phe Val
            35                  40                  45

Ser Ala Ile Ser Glu Asn Gly Asp Ala Trp Asn Tyr Tyr Ala Asp Ser
        50                  55                  60

Val Lys Gly Arg Phe Thr Ile Ser Arg Asp Asn Ser Lys Asn Thr Val
65                  70                  75                  80

Tyr Leu Gln Met Asn Ser Leu Arg Ala Glu Asp Thr Ala Thr Tyr Tyr
                85                  90                  95

Cys Ala Ile Gly Phe Asp Val Pro Ser Gly Arg Ser Trp Gln Gly Ser
            100                 105                 110
```

```
His Phe Trp Met Tyr Trp Gly Gln Gly Thr Gln Val Thr Val Ser Ser
        115                 120                 125
```

```
<210> SEQ ID NO 10
<211> LENGTH: 119
<212> TYPE: PRT
<213> ORGANISM: Artificial Sequence
<220> FEATURE:
<223> OTHER INFORMATION: Synthetic

<400> SEQUENCE: 10

Glu Val Gln Leu Gln Ala Ser Gly Gly Gly Phe Val Gln Pro Gly Gly
1               5                   10                  15

Ser Leu Arg Leu Ser Cys Ala Ala Ser Gly Thr Thr Ser Arg Trp Glu
            20                  25                  30

Ser Met Gly Trp Phe Arg Gln Ala Pro Gly Lys Glu Arg Glu Phe Val
        35                  40                  45

Ser Ala Ile Ser Trp Gln Asn Asn Ser Val Pro Tyr Tyr Ala Asp Ser
        50                  55                  60

Val Lys Gly Arg Phe Thr Ile Ser Arg Asp Asn Ser Lys Asn Thr Val
65                  70                  75                  80

Tyr Leu Gln Met Asn Ser Leu Arg Ala Glu Asp Thr Ala Thr Tyr Tyr
                85                  90                  95

Cys Ala Ala Gln His Asn Phe Leu Gly His Arg Tyr Trp Gly Gln Gly
            100                 105                 110

Thr Gln Val Thr Val Ser Ser
        115
```

```
<210> SEQ ID NO 11
<211> LENGTH: 502
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 11

Met Ser Arg Asp Pro Leu Pro Phe Phe Pro Pro Leu Tyr Leu Gly Gly
1               5                   10                  15

Pro Glu Ile Thr Thr Glu Asn Cys Glu Arg Glu Pro Ile His Ile Pro
            20                  25                  30

Gly Ser Ile Gln Pro His Gly Ala Leu Leu Thr Ala Asp Gly His Ser
        35                  40                  45

Gly Glu Val Leu Gln Met Ser Leu Asn Ala Ala Thr Phe Leu Gly Gln
        50                  55                  60

Glu Pro Thr Val Leu Arg Gly Gln Thr Leu Ala Ala Leu Leu Pro Glu
65                  70                  75                  80

Gln Trp Pro Ala Leu Gln Ala Ala Leu Pro Pro Gly Cys Pro Asp Ala
                85                  90                  95

Leu Gln Tyr Arg Ala Thr Leu Asp Trp Pro Ala Ala Gly His Leu Ser
            100                 105                 110

Leu Thr Val His Arg Val Gly Glu Leu Leu Ile Leu Glu Phe Glu Pro
        115                 120                 125

Thr Glu Ala Trp Asp Ser Thr Gly Pro His Ala Leu Arg Asn Ala Met
    130                 135                 140

Phe Ala Leu Glu Ser Ala Pro Asn Leu Arg Ala Leu Ala Glu Val Ala
```

```
145                150                155                160

Thr Gln Thr Val Arg Glu Leu Thr Gly Phe Asp Arg Val Met Leu Tyr
                165                170                175

Lys Phe Ala Pro Asp Ala Thr Gly Glu Val Ile Ala Glu Ala Arg Arg
                180                185                190

Glu Gly Leu His Ala Phe Leu Gly His Arg Phe Pro Ala Ser Asp Ile
                195                200                205

Pro Ala Gln Ala Arg Ala Leu Tyr Thr Arg His Leu Leu Arg Leu Thr
        210                215                220

Ala Asp Thr Arg Ala Ala Ala Val Pro Leu Asp Pro Val Leu Asn Pro
225                230                235                240

Gln Thr Asn Ala Pro Thr Pro Leu Gly Gly Ala Val Leu Arg Ala Thr
                245                250                255

Ser Pro Met His Met Gln Tyr Leu Arg Asn Met Gly Val Gly Ser Ser
                260                265                270

Leu Ser Val Ser Val Val Val Gly Gly Gln Leu Trp Gly Leu Ile Ala
                275                280                285

Cys His His Gln Thr Pro Tyr Val Leu Pro Pro Asp Leu Arg Thr Thr
        290                295                300

Leu Glu Tyr Leu Gly Arg Leu Leu Ser Leu Gln Val Gln Val Lys Glu
305                310                315                320

Ala Ala Asp Val Ala Ala Phe Arg Gln Ser Leu Arg Glu His His Ala
                325                330                335

Arg Val Ala Leu Ala Ala Ala His Ser Leu Ser Pro His Asp Thr Leu
                340                345                350

Ser Asp Pro Ala Leu Asp Leu Leu Gly Leu Met Arg Ala Gly Gly Leu
                355                360                365

Ile Leu Arg Phe Glu Gly Arg Trp Gln Thr Leu Gly Glu Val Pro Pro
        370                375                380

Ala Pro Ala Val Asp Ala Leu Leu Ala Trp Leu Glu Thr Gln Pro Gly
385                390                395                400

Ala Leu Val Gln Thr Asp Ala Leu Gly Gln Leu Trp Pro Ala Gly Ala
                405                410                415

Asp Leu Ala Pro Ser Ala Ala Gly Leu Leu Ala Ile Ser Val Gly Glu
                420                425                430

Gly Trp Ser Glu Cys Leu Val Trp Leu Arg Pro Glu Leu Arg Leu Glu
                435                440                445

Val Ala Trp Gly Gly Ala Thr Pro Asp Gln Ala Lys Asp Asp Leu Gly
        450                455                460

Pro Arg His Ser Phe Asp Thr Tyr Leu Glu Glu Lys Arg Gly Tyr Ala
465                470                475                480

Glu Pro Trp His Pro Gly Glu Ile Glu Glu Ala Gln Asp Leu Arg Asp
                485                490                495

Thr Leu Thr Gly Ala Leu
                500
```

<210> SEQ ID NO 12
<211> LENGTH: 7
<212> TYPE: PRT
<213> ORGANISM: Artificial Sequence
<220> FEATURE:
<223> OTHER INFORMATION: Synthetic

<400> SEQUENCE: 12

Asp Thr Ser Tyr Leu Tyr Ser

-continued

```
1               5

<210> SEQ ID NO 13
<211> LENGTH: 7
<212> TYPE: PRT
<213> ORGANISM: Artificial Sequence
<220> FEATURE:
<223> OTHER INFORMATION: Synthetic

<400> SEQUENCE: 13

Trp Trp Trp Asn Leu Thr Gln
1               5

<210> SEQ ID NO 14
<211> LENGTH: 15
<212> TYPE: PRT
<213> ORGANISM: Artificial Sequence
<220> FEATURE:
<223> OTHER INFORMATION: Synthetic

<400> SEQUENCE: 14

Trp Ser Ile Tyr Phe Pro Pro Gly Asn Asp Tyr Asn Gly Tyr His
1               5                   10                  15

<210> SEQ ID NO 15
<211> LENGTH: 7
<212> TYPE: PRT
<213> ORGANISM: Artificial Sequence
<220> FEATURE:
<223> OTHER INFORMATION: Synthetic

<400> SEQUENCE: 15

Phe Phe Ser Asn Trp Ser Asp
1               5

<210> SEQ ID NO 16
<211> LENGTH: 7
<212> TYPE: PRT
<213> ORGANISM: Artificial Sequence
<220> FEATURE:
<223> OTHER INFORMATION: Synthetic

<400> SEQUENCE: 16

Phe Trp Ala Asp Gly Thr Glu
1               5

<210> SEQ ID NO 17
<211> LENGTH: 12
<212> TYPE: PRT
<213> ORGANISM: Artificial Sequence
<220> FEATURE:
<223> OTHER INFORMATION: Synthetic

<400> SEQUENCE: 17

Trp Tyr Gly Pro Val Asn Gly Phe Tyr Met Phe Asp
1               5                   10

<210> SEQ ID NO 18
<211> LENGTH: 7
<212> TYPE: PRT
<213> ORGANISM: Artificial Sequence
<220> FEATURE:
<223> OTHER INFORMATION: Synthetic

<400> SEQUENCE: 18

Ser Thr Ser Asp Phe Glu Ser
1               5
```

```
<210> SEQ ID NO 19
<211> LENGTH: 7
<212> TYPE: PRT
<213> ORGANISM: Artificial Sequence
<220> FEATURE:
<223> OTHER INFORMATION: Synthetic

<400> SEQUENCE: 19

Ser Trp Phe Thr Asn Pro Pro
1               5

<210> SEQ ID NO 20
<211> LENGTH: 9
<212> TYPE: PRT
<213> ORGANISM: Artificial Sequence
<220> FEATURE:
<223> OTHER INFORMATION: Synthetic

<400> SEQUENCE: 20

His Arg Ser Ile Trp Tyr His Pro Thr
1               5

<210> SEQ ID NO 21
<211> LENGTH: 1659
<212> TYPE: DNA
<213> ORGANISM: Artificial Sequence
<220> FEATURE:
<223> OTHER INFORMATION: Synthetic

<400> SEQUENCE: 21
atgagtcgtg accctttgcc attctttcct cctctttatc tgggtggacc cgagattaca      60
acagaaaact gcgaacgcga accaattcac atcccgggat ctattcaacc acacggtgca     120
ttgctgacgg cagacggaca ttccggagag gttttacaga tgtcgcttaa cgcagcaacg     180
tttctgggac aagagcctac ggttttgcgc ggccagacgt tagcggctct gttgccagag     240
caatggccgg ccttacaggc ggcattgcct ccagggtgcc ccgatgcatt gcaataccgc     300
gcgacactgg attggccggc ggcaggacat ctttctctga cagtccaccg cgtgggcgag     360
ctgttgatcc tggagtttga acctacggag gcctgggact cgactggccc gcacgcgtta     420
cgcaatgcga tgttcgctct tgaatcagcg ccaaacttgc gcgcgttagc tgaagtggcc     480
acacaaaccg tacgcgagct tacaggcttt gaccgcgtga tgttatacaa attcgcaccc     540
gatgcgacag gcgaggtaat cgccgaagcc cgccgcgagg ggttgcatgc ctttcttggc     600
catcgttttc cggcctcaga tattcccgcc caagcgcgcg ccctttacac tcgccatctg     660
cttcgtttga ctgcggacac gcgcgcggcg gccgttccct tagacccagt acttaatcct     720
cagactaacg ctcctacccc cttaggggg gcagtgctgc gtgcgacgtc gcctatgcac     780
atgcagtacc ttcgcaatat gggcgtcggc tcctctttaa gtgtatcagt ggtagttggg     840
gggcagttat ggggtctgat tgcgtgccat catcagaccc cctatgtttt gccaccagac     900
cttcgtacta ctcttgaata cttggggcgt ttattaagcc ttcaggtgca agtcaaggaa     960
gccgcggacg ttgctgcatt ccgtcagtca cttcgcgaac accatgcgcg cgtcgcctta    1020
gcggcagcgc attccctgtc gccgcacgat actctttccg accctgcact tgatcttctg    1080
ggtctgatgc gtgctggggg cttaatcctg cgttttgaag gtcgttggca gacgttagga    1140
gaagtcccgc ccgctcccgc agtcgatgca ctgcttgcat ggcttgaaac ccaaccaggg    1200
gcgcttgttc agactgatgc attggggcag ttgtggccgg cggggctga tttggctccc    1260
```

```
tcagccgcgg gtctgcttgc catttcagta ggggagggat ggagtgagtg cttggtttgg     1320
ttacgtcccg aactgcgcct tgaggttgcg tggggtggag caactccaga ccaggccaag     1380
gacgacctgg gccctcgtca cagtttcgat acttacttag aagagaagcg tgggtatgca     1440
gaaccctggc atcccggaga gattgaggaa gctcaggatt tgcgcgacac tcttactggc     1500
gcattaaagc ttggtggcgg tagcgagaat ttgtattttc agggtggcgg tggcagtagc     1560
ttatccaccc cgccgacccc gagcactcct cctaccggtc tgaacgacat cttcgaggct     1620
cagaaaatcg aatggcacga acatcatcac caccatcac                            1659
```

```
<210> SEQ ID NO 22
<211> LENGTH: 24
<212> TYPE: DNA
<213> ORGANISM: Artificial Sequence
<220> FEATURE:
<223> OTHER INFORMATION: Synthetic

<400> SEQUENCE: 22
gaattccatc atcaccatca ccat                                            24
```

```
<210> SEQ ID NO 23
<211> LENGTH: 417
<212> TYPE: DNA
<213> ORGANISM: Artificial Sequence
<220> FEATURE:
<223> OTHER INFORMATION: Synthetic

<400> SEQUENCE: 23
gaagttcagc tgcaggcaag cggtggtggt tttgttcagc ctggtggtag cctgcgtctg     60
agctgtgcag ccagcggttt tacctgggat cattacatca tgggctggtt tcgccaggca     120
ccgggtaaag aacgtgaatt tgttagcgca atcagcgaaa atggtgatgc atggaattat     180
tatgccgata gcgtgaaagg tcgctttacc attagccgtg ataatagcaa aaataccgtt     240
tacctgcaga tgaatagtct gcgtgcagaa gataccgcaa cctattattg tgcaatcggt     300
tttgatgttc catctggtcg ttcttggcag ggttctcatt tttggatgta ttggggtcag     360
ggcacccagg ttaccgttag cagcagcccg ggaggccaac accatcacca ccatcat        417
```

```
<210> SEQ ID NO 24
<211> LENGTH: 126
<212> TYPE: DNA
<213> ORGANISM: Artificial Sequence
<220> FEATURE:
<223> OTHER INFORMATION: Synthetic

<400> SEQUENCE: 24
agcccgggag gccaaagctt atccaccccg agtgtagatc tcggtggtcg ccgtatcatt     60
ggtctgaacg acatcttcga ggctcagaaa atcgaatggc acgaacatca tcaccaccat     120
cactct                                                                126
```

```
<210> SEQ ID NO 25
<211> LENGTH: 390
<212> TYPE: DNA
<213> ORGANISM: Artificial Sequence
<220> FEATURE:
<223> OTHER INFORMATION: Synthetic

<400> SEQUENCE: 25
gaagttcagc tgcaggcaag cggtggtggt tttgttcagc ctggtggtag cctgcgtctg     60
agctgtgcag ccagcggtac cacctctcgt tgggaatcta tgggctggtt tcgccaggca     120
```

```
ccgggtaaag aacgtgaatt tgttagcgca atcagctggc agaataattc tgttccatat      180
tatgccgata gcgtgaaagg tcgctttacc attagccgtg ataatagcaa aaataccgtt      240
tacctgcaga tgaatagtct gcgtgcagaa gataccgcaa cctattattg tgcagcacag      300
cataactttc tgggtcatcg ttattggggt cagggcaccc aggttaccgt tagcagcagc      360
ccgggaggcc aacaccatca ccaccatcat                                       390

<210> SEQ ID NO 26
<211> LENGTH: 126
<212> TYPE: DNA
<213> ORGANISM: Artificial Sequence
<220> FEATURE:
<223> OTHER INFORMATION: Synthetic

<400> SEQUENCE: 26
agcccgggag gccaaagctt atccaccccg agtgtagatc tcggtggtcg ccgtatcatt       60
ggtctgaacg acatcttcga ggctcagaaa atcgaatggc acgaacatca tcaccaccat      120
cactct                                                                 126

<210> SEQ ID NO 27
<211> LENGTH: 522
<212> TYPE: DNA
<213> ORGANISM: Artificial Sequence
<220> FEATURE:
<223> OTHER INFORMATION: Synthetic

<400> SEQUENCE: 27
atgaagctac tgtcttctat cgaacaagca tgcgatattt gccgacttaa aaagctcaag       60
tgctccaaag aaaaaccgaa gtgcgccaag tgtctgaaga acaactggga gtgtcgctac      120
tctcccaaaa ccaaaaggtc tccgctgact agggcacatc tgacagaagt ggaatcaagg      180
ctagaaagac tggaacagct atttctactg attttttcctc gagaagacct tgacatgatt      240
ttgaaaatgg attctttaca ggatataaaa gcattgttaa caggattatt tgtacaagat      300
aatgtgaata aagatgccgt cacagataga ttggcttcag tggagactga tatgcctcta      360
acattgagac agcatagaat aagtgcgaca tcatcatcgg aagagagtag taacaaaggt      420
caaagacagt tgactgtatc gccggaattt gtaatacgac tcactatagg gcgagccgcc      480
atcatggagg agcagaagct gatctcagag gaggacctgc at                        522

<210> SEQ ID NO 28
<211> LENGTH: 507
<212> TYPE: DNA
<213> ORGANISM: Artificial Sequence
<220> FEATURE:
<223> OTHER INFORMATION: Synthetic

<400> SEQUENCE: 28
atggataaag cggaattaat tcccgagcct ccaaaaaaga agagaaaggt cgaattgggt       60
accgccgcca attttaatca aagtgggaat attgctgata gctcattgtc cttcactttc      120
actaacagta gcaacggtcc gaacctcata acaactcaaa caaattctca agcgctttca      180
caaccaattg cctcctctaa cgttcatgat aacttcatga ataatgaaat cacggctagt      240
aaaattgatg atggtaataa ttcaaaacca ctgtcacctg gttggacgga ccaaactgcg      300
tataacgcgt ttggaatcac tacagggatg tttaatacca ctacaatgga tgatgtatat      360
aactatctat tcgatgatga agataccccca ccaaacccaa aaaagagat ctttaatacg      420
```

-continued

```
actcactata gggcgagcgc cgccatggag tacccatacg acgtaccaga ttacgctcat    480
atgggaggcg gttccggtgg cggttct                                      507

<210> SEQ ID NO 29
<211> LENGTH: 474
<212> TYPE: DNA
<213> ORGANISM: Artificial Sequence
<220> FEATURE:
<223> OTHER INFORMATION: Synthetic

<400> SEQUENCE: 29
atctttaata cgactcacta tagggcgagc gccgccatgg agtacccata cgacgtacca     60
gattacgctc atatgggagg cggttccggt ggcggttctg aagttcagct gcaggcaagc    120
ggtggtggtt ttgttcagcc tggtggtagc ctgcgtctga gctgtgcagc cagcggtgat    180
acctcttacc tgtactctat gggctggttt cgccaggcac cgggtaaaga acgtgaattt    240
gttagcgcaa tcagctggtg gtggaatctg actcagtatt atgccgatag cgtgaaaggt    300
cgctttacca ttagccgtga taatagcaaa aataccgttt acctgcagat gaatagtctg    360
cgtgcagaag ataccgcaac ctattattgt gcatggtcta tctactttcc accaggtaac    420
gattacaacg gttaccatta ttggggtcag ggcacccagg ttaccgttag cagc          474

<210> SEQ ID NO 30
<211> LENGTH: 465
<212> TYPE: DNA
<213> ORGANISM: Artificial Sequence
<220> FEATURE:
<223> OTHER INFORMATION: Synthetic

<400> SEQUENCE: 30
atctttaata cgactcacta tagggcgagc gccgccatgg agtacccata cgacgtacca     60
gattacgctc atatgggagg cggttccggt ggcggttctg aagttcagct gcaggcaagc    120
ggtggtggtt ttgttcagcc tggtggtagc ctgcgtctga gctgtgcagc cagcggtttt    180
ttttctaact ggtctgatat gggctggttt cgccaggcac cgggtaaaga acgtgaattt    240
gttagcgcaa tcagcttttg gcagatggt actgaatatt atgccgatag cgtgaaaggt    300
cgctttacca ttagccgtga taatagcaaa aataccgttt acctgcagat gaatagtctg    360
cgtgcagaag ataccgcaac ctattattgt gcatggtacg gtccagttaa cggttttttac    420 atgtttgatt attggggtca gggcacccag gttaccgtta gcagc                    465

<210> SEQ ID NO 31
<211> LENGTH: 456
<212> TYPE: DNA
<213> ORGANISM: Artificial Sequence
<220> FEATURE:
<223> OTHER INFORMATION: Synthetic

<400> SEQUENCE: 31
atctttaata cgactcacta tagggcgagc gccgccatgg agtacccata cgacgtacca     60
gattacgctc atatgggagg cggttccggt ggcggttctg aagttcagct gcaggcaagc    120
ggtggtggtt ttgttcagcc tggtggtagc ctgcgtctga gctgtgcagc cagcggttct    180
acctctgatt ttgaatctat gggctggttt cgccaggcac cgggtaaaga acgtgaattt    240
gttagcgcaa tcagctcttg gtttactaat ccaccatatt atgccgatag cgtgaaaggt    300
cgctttacca ttagccgtga taatagcaaa aataccgttt acctgcagat gaatagtctg    360
cgtgcagaag ataccgcaac ctattattgt gcacatcgtt ctatctggta ccatccaacc    420
```

```
tattggggtc agggcaccca ggttaccgtt agcagc                                    456

<210> SEQ ID NO 32
<211> LENGTH: 99
<212> TYPE: DNA
<213> ORGANISM: Artificial Sequence
<220> FEATURE:
<223> OTHER INFORMATION: Synthetic

<400> SEQUENCE: 32
atctttaata cgactcacta tagggcgagc gccgccatgg agtacccata cgacgtacca         60
gattacgctc atatgggagg cggttccggt ggcggttct                                99

<210> SEQ ID NO 33
<211> LENGTH: 984
<212> TYPE: DNA
<213> ORGANISM: Artificial Sequence
<220> FEATURE:
<223> OTHER INFORMATION: Synthetic

<400> SEQUENCE: 33
atgggatccc ccaagaagaa gcgcaaggtg gaagctagcg cttccccgaa gaaaaagcgg         60
aaagtcgagg cctccgcatc tccaaaaaaa aaaagcaagg ttgaagcatc tggatccggt        120 accgaggaa gtggcagctc tggcggcagt ggagggtctg gtggcagcgg aagcggcggc        180
ggtggcagtc agtacctgcc agatacagac gatcgtcacc ggattgagga gaaacgtaaa        240
aggacatatg agaccttcaa gagcatcatg aagaagagtc ctttcagcgg acccaccgac        300
ccccggcctc cacctcgacg cattgctgtg ccttcccgca gctcagcttc tgtccccaag        360
ccagcacccc agcccatcc ctttacgtca tccctgagca ccatcaacta tgatgagttt        420
cccaccatgg tgtttccttc tgggcagatc agccaggcct cggccttggc cccggcccct        480
ccccaagtcc tgccccaggc tccagcccct gccctgctc cagccatggt atcagctctg        540
gcccaggccc cagcccctgt cccagtccta gccccaggcc ctcctcaggc tgtggcccca        600 cctgcccca agcccaccca ggctggggaa ggaacgctgt cagaggccct gctgcagctg        660
cagtttgatg atgaagacct ggggggccttg cttggcaaca gcacagaccc agctgtgttc        720
acagacctgg catccgtcga caactccgag tttcagcagc tgctgaacca gggcatacct        780 gtggccccc acacaactga gcccatgctg atggagtacc ctgaggctat aactcgccta        840
gtgacagggg cccagaggcc ccccgaccca gctcctgctc cactgggggc cccggggctc        900
cccaatggcc tcctttcagg agatgaagac ttctcctcca ttgcggacat ggacttctca        960
gccctgctga gtcagatcag ctcc                                                984

<210> SEQ ID NO 34
<211> LENGTH: 78
<212> TYPE: DNA
<213> ORGANISM: Artificial Sequence
<220> FEATURE:
<223> OTHER INFORMATION: Synthetic

<400> SEQUENCE: 34
ggatccggta ccgaggaag tggcagctct ggcggcagtg agggtctgg tggcagcgga         60 agcggcggcg gtggcagt                                                       78

<210> SEQ ID NO 35
<211> LENGTH: 78
<212> TYPE: DNA
```

<213> ORGANISM: Artificial Sequence
<220> FEATURE:
<223> OTHER INFORMATION: Synthetic

<400> SEQUENCE: 35
ggatccggta ccggaggaag tggcagctct ggcggcagtg gagggtctgg tggcagcgga      60
agcggcggcg gtggcagt                                                    78

<210> SEQ ID NO 36
<211> LENGTH: 78
<212> TYPE: DNA
<213> ORGANISM: Artificial Sequence
<220> FEATURE:
<223> OTHER INFORMATION: Synthetic

<400> SEQUENCE: 36
ggatccggta ccggaggaag tggcagctct ggcggcagtg gagggtctgg tggcagcgga      60
agcggcggcg gtggcagt                                                    78

<210> SEQ ID NO 37
<211> LENGTH: 219
<212> TYPE: DNA
<213> ORGANISM: Artificial Sequence
<220> FEATURE:
<223> OTHER INFORMATION: Synthetic

<400> SEQUENCE: 37
atgcccaaga agaagcgcaa ggtggaagct agcgcttccc cgaagaaaaa gcggaaagtc      60
gaggcctccg catctccaaa aaaaaaaagc aaggttgaag catctggatc cggaggcggt     120
tccggtggcg gttctggtac cggaggaagt ggcagctctg gcggcagtgg agggtctggt     180
ggcagcggag gaggaagtgg cagctctggc ggcagtgga                            219

<210> SEQ ID NO 38
<211> LENGTH: 2274
<212> TYPE: DNA
<213> ORGANISM: Artificial Sequence
<220> FEATURE:
<223> OTHER INFORMATION: Synthetic

<400> SEQUENCE: 38
ccggaatttg taatacgact cactataggg cgagccgcca tcatggagga gcagaagctg      60
atctcagagg aggacctgca tgtggcaggt catgcctctg gcagcccgc attcgggacc      120 gccgatcttt cgaattgcga acgtgaagag atccacctcg ccggctcgat ccagccgcat     180
ggcgcgcttc tggtcgtcag cgagccggat catcgcatca tccaggccag cgccaacgcc     240
gcggaatttc tgaatctcgg aagcgtgctc ggcgttccgc tcgccagat cgacggcgat      300 ctgttgatca agatcctgcc gcatctcgat cccaccgccg aaggcatgcc ggtcgcggtg      360
cgctgccgga tcggcaatcc ctccacggag tacgacggtc tgatgcatcg gcctccggaa      420
ggcgggctga tcatcgagct cgaacgtgcc ggcccgccga tcgatctgtc cggcacgctg      480
gcgccggcgc tggagcggat ccgcacggcg ggctcgctgc gcgcgctgtg cgatgacacc      540
gcgctgctgt ttcagcagtg caccggctac gaccgggtga tggtgtatcg cttcgacgag      600
cagggccacg gcgaagtgtt ctccgagcgc cacgtgcccg ggctcgaatc ctatttcggc      660
aaccgctatc cgtcgtcgga cattccgcag atggcgcggc ggctgtacga gcggcagcgc      720
gtccgcgtgc tggtcgacgt cagctatcag ccggtgccgc tggagccgcg cctgtcgccg      780
ctgaccgggc gcgatctcga catgtcgggc tgcttcctgc gctcgatgtc gccgatccat      840

-continued

```
ctgcagtacc tgaagaacat gggcgtgcgc gccaccctgg tggtgtcgct ggtggtcggc      900
ggcaagctgt ggggcctggt tgcctgtcac cattatctgc cgcgcttcat ccatttcgag      960
ctgcgggcga tctgcgaact gctcgccgaa gcgatcgcga cgcggatcac cgcgcttgag     1020
agcttcgcgc agagccagtc ggagctgttc gtgcagcggc tcgaacagcg catgatcgaa     1080
gcgatcaccc gtgaaggcga ttggcgcgca gcgattttcg acaccagcca atcgatcctg     1140
cagccgctgc acgccgacgg ttgcgcgctg gtgtacgaag accagatcag gaccatcggt     1200
gacgtacctt ccacgcagga tgttcgcgag atcgccgggt ggctcgatcg ccagccacgt     1260
gcggcggtga cctcgaccgc gtcgctcggt ctcgacgtgc cggagctcgc gcatctgacg     1320
cggatggcga gcggcgtggt cgcggcgccg atttcggatc atcgcggcga gtttctgatg     1380
tggttccgcc ccgagcgcgt ccacaccgtt acctggggcg cgcgatccga a gaagccgttc     1440 acgatgggcg atacaccggc ggatctgtcg ccgcggcgct ccttcgccaa atggcatcag     1500
gttgtcgaag gcacgtccga tccgtggacg gccgccgatc tcgccgcggc tcgcaccatc     1560
ggtcagaccg tcgccgacat cgtgctgcaa ttccgcgcgg tgcggacact gatcgcccgc     1620
gaacagtacg aacagttttc gtcccaggtg cacgcttcga tgcagccggt gctgatcacc     1680
gacgccgaag gccgcatcct gctgatgaac gactcgttcc gcgacatgtt gccggcgggg     1740
tcgccatccg ccgtccatct cgacgatctc gccgggttct tcgtcgaatc gaacgatttc     1800
ctgcgcaacg tcgccgaact gatcgatcac ggccgcgggt ggcgcggcga gttctgctg      1860 cgcggcgcag gtaatcgccc gttgccgctg gcagtgcgcg ccgatccggt gacgcgcacg     1920
gaggaccagt cgctcggctt cgtgctgatc ttcagcgacg ctaccgatcg tcgcaccgca     1980
gatgccgcac gcacgcgttt ccaggaaggc attcttgcca gcgcacgtcc cggcgtgcgg     2040
ctcgactcca agtccgacct cttgcacgag aagctgctgt ccgcgctggt cgagaacgcg     2100
cagcttgccg cattggaaat tacttacggc gtcgagaccg gacgcatcgc cgagctgctc     2160
gaaggcgttc gccagtcgat gctgcgcacc gccgaagtgc tcggccatct ggtgcagcac     2220
gcggcgcgca cggccggcag cgacagctcg agcaatggct cgcagaacaa gaag           2274
```

<210> SEQ ID NO 39
<211> LENGTH: 1611
<212> TYPE: DNA
<213> ORGANISM: Artificial Sequence
<220> FEATURE:
<223> OTHER INFORMATION: Synthetic

<400> SEQUENCE: 39

```
atgcccaaga agaagcgcaa ggtggaagct agcgcttccc cgaagaaaaa gcggaaagtc       60
gaggcctccg catctccaaa aaaaaaaagc aaggttgaag catctggatc cggaggcggt      120
tccggtggcg gttctgtggc gtcaaagtcc gttcatgccg acatcaccct tctgctcgat      180
atggagggtg tgattcgcga agccaccctg tctccgacga tggcggccga gagcgtggac      240
ggttggctgg ggcgtcgctg gagcgacatc gccggcgccg aaggcggcga caaggttcgc      300
cgcatggtcg aagacgcccg ccgcagcggc atctcggctt ccgccagat caatcagcct       360 ttcccgagcg gcgtcgaaat cccgatcgaa ttcaccacga tgctgctggg cgaccgcacc      420
ggcatgatcg cggtcggcaa gaacatgcag gcggtcaccg agctgcattc ccggctgatc      480
gctgcgcagc aggcgatgga gcgcgactat tggcggttgc gtgaattgga gactcgctac      540
cgcctggtgt tcgacgctgc cgccgatgcg gtgatgatcg tctccgccgg cgacatgcgc      600
```

-continued

```
atcgtcgaag ccaaccgggc ggcggtgaat gcgatcagcc gcgtcgagcg cggcaatgac      660
gaccttgcgg ggcgtgattt cctcgccgaa gtggcggctg ccgatcgcga tgcggtgcgc      720
gacatgctgg cccaggtgcg tcagcgcggc accgcactca gcgtcctcgt tcatctcggc      780
cgttacgacc gcgcctggat gctgcgcggt tcgctgatgt cgtccgagcg tcgtcaggtt      840
ttcctgctgc acttcacccc ggtgaccacg actcccgcga tcgacgacgt cgacgatgat      900
gccgtgctgc gcgggctgat cgatcgcatt cccgacgggt tcgtcgcact ggattcggaa      960
ggcgtcgttc gtcacgccaa ccaggcgttt ctcgatctgg tccagatcgg ctccaagcct     1020
gcggcggtcg gacgatcgct gggcgtctgg atgggtcgtc cgggcgccga tctgtccagc     1080
ttgctgacgc tgctgcggcg ctacaagacg gtgcggctgt ccaaacgac gatccgcggc      1140 gagctcggca ccgagactga agtcgaggtc tcggccgtcg acggcgagga cgaccaatac     1200
atcggcgttc tgatgcgcaa tgtcgcgcga cgcctcgacg ctgcggacga ccacgatgcc     1260
ttgcgtcagg cgctcggccc gatcagcaag cagctcgggc gatcctcgct gcgcaagctg     1320
gtgaagaacg ccgtgagcat tgtcgagcag cactacgtga aggaagcgct gttgcgatcc     1380
aagggcaatc gcacggcaac tgccgaactg ctcggattga gccggcagag cctttatgca     1440
aaactcaact cctacggctt cgacgacaaa ggtgtcgttg cttctgctgc cgacggtgca     1500
gagggcgcct cagacgacgc agaggatggt accggaggaa gtggcagctc tggcggcagt     1560
ggagggtctg gtggcagcgg aggaggaagt ggcagctctg cggcagtgg a               1611
```

```
<210> SEQ ID NO 40
<211> LENGTH: 672
<212> TYPE: DNA
<213> ORGANISM: Artificial Sequence
<220> FEATURE:
<223> OTHER INFORMATION: Synthetic

<400> SEQUENCE: 40
atgcccaaga agaagcgcaa ggtggaagct agcgcttccc cgaagaaaaa gcggaaagtc       60
gaggcctccg catctccaaa aaaaaaaagc aaggttgaag catctggatc cggaggcggt      120
tccggtggcg gttctggcaa gaacatgcag gcggtcaccg agctgcattc ccggctgatc      180
gctgcgcagc aggcgatgga gcgcgactat tggcggttgc gtgaattgga gactcgctac      240
cgcctggtgt cgacgctgc cgccgatgcg gtgatgatcg tctccgccgg cgacatgcgc      300
atcgtcgaag ccaaccgggc ggcggtgaat gcgatcagcc gcgtcgagcg cggcaatgac      360
gaccttgcgg ggcgtgattt cctcgccgaa gtggcggctg ccgatcgcga tgcggtgcgc      420
gacatgctgg cccaggtgcg tcagcgcggc accgcactca gcgtcctcgt tcatctcggc      480
cgttacgacc gcgcctggat gctgcgcggt tcgctgatgt cgtccgagcg tcgtcaggtt      540
ttcctgctgc acttcacccc ggtgaccacg actcccgcga tcgacgacgg taccggagga     600
agtggcagct ctggcggcag tggagggtct ggtggcagcg gaggaggaag tggcagctct     660
ggcggcagtg ga                                                          672
```

```
<210> SEQ ID NO 41
<211> LENGTH: 573
<212> TYPE: DNA
<213> ORGANISM: Artificial Sequence
<220> FEATURE:
<223> OTHER INFORMATION: Synthetic

<400> SEQUENCE: 41
atgggatccg ttaacggcgg cggtggcagt gacaaagact gcgaaatgaa gcgcaccacc       60
```
ctggatagcc ctctgggcaa gctggaactg tctgggtgcg aacagggcct gcaccgtatc     120
atcttcctgg gcaaaggaac atctgccgcc gacgccgtgg aagtgcctgc cccagccgcc     180
gtgctgggcg gaccagagcc actgatgcag gccaccgcct ggctcaacgc ctactttcac     240
cagcctgagg ccatcgagga gttccctgtg ccagccctgc accacccagt gttccagcag     300
gagagcttta cccgccaggt gctgtggaaa ctgctgaaag tggtgaagtt cggagaggtc     360
atcagctaca gccacctggc cgccctggcc ggcaatcccg ccgccaccgc cgccgtgaaa     420
accgccctga gcggaaatcc cgtgcccatt ctgatccect gccaccgggt ggtgcagggc     480
gacctggacg tggggggcta cgagggcggg ctcgccgtga aagagtggct gctggcccac     540
gagggccaca gactgggcaa gcctgggctg ggt                                  573

<210> SEQ ID NO 42
<211> LENGTH: 30
<212> TYPE: DNA
<213> ORGANISM: Artificial Sequence
<220> FEATURE:
<223> OTHER INFORMATION: Synthetic

<400> SEQUENCE: 42
atgggatccg ttaacggcgg cggtggcagt                                       30

<210> SEQ ID NO 43
<211> LENGTH: 30
<212> TYPE: DNA
<213> ORGANISM: Artificial Sequence
<220> FEATURE:
<223> OTHER INFORMATION: Synthetic

<400> SEQUENCE: 43
atgggatccg ttaacggcgg cggtggcagt                                       30

<210> SEQ ID NO 44
<211> LENGTH: 30
<212> TYPE: DNA
<213> ORGANISM: Artificial Sequence
<220> FEATURE:
<223> OTHER INFORMATION: Synthetic

<400> SEQUENCE: 44
atgggatccg ttaacggcgg cggtggcagt                                       30

<210> SEQ ID NO 45
<211> LENGTH: 30
<212> TYPE: DNA
<213> ORGANISM: Artificial Sequence
<220> FEATURE:
<223> OTHER INFORMATION: Synthetic

<400> SEQUENCE: 45
atgggatccg ttaacggcgg cggtggcagt                                       30

<210> SEQ ID NO 46
<211> LENGTH: 26
<212> TYPE: PRT
<213> ORGANISM: Artificial Sequence
<220> FEATURE:
<223> OTHER INFORMATION: Synthetic

<400> SEQUENCE: 46

Glu Val Gln Leu Gln Ala Ser Gly Gly Gly Phe Val Gln Pro Gly Gly
1               5                   10                  15

Ser Leu Arg Leu Ser Cys Ala Ala Ser Gly
            20                  25

<210> SEQ ID NO 47
<211> LENGTH: 19
<212> TYPE: PRT
<213> ORGANISM: Artificial Sequence
<220> FEATURE:
<223> OTHER INFORMATION: Synthetic

<400> SEQUENCE: 47

Met Gly Trp Phe Arg Gln Ala Pro Gly Lys Glu Arg Glu Phe Val Ser
1               5                   10                  15

Ala Ile Ser

<210> SEQ ID NO 48
<211> LENGTH: 39
<212> TYPE: PRT
<213> ORGANISM: Artificial Sequence
<220> FEATURE:
<223> OTHER INFORMATION: Synthetic

<400> SEQUENCE: 48

Tyr Tyr Ala Asp Ser Val Lys Gly Arg Phe Thr Ile Ser Arg Asp Asn
1               5                   10                  15

Ser Lys Asn Thr Val Tyr Leu Gln Met Asn Ser Leu Arg Ala Glu Asp
            20                  25                  30

Thr Ala Thr Tyr Tyr Cys Ala
        35

<210> SEQ ID NO 49
<211> LENGTH: 12
<212> TYPE: PRT
<213> ORGANISM: Artificial Sequence
<220> FEATURE:
<223> OTHER INFORMATION: Synthetic

<400> SEQUENCE: 49

Tyr Trp Gly Gln Gly Thr Gln Val Thr Val Ser Ser
1               5                   10

<210> SEQ ID NO 50
<211> LENGTH: 26
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (3)..(3)
<223> OTHER INFORMATION: X is K, Q, N, R, D, or E
<220> FEATURE:
<221> NAME/KEY: VARIANT
<222> LOCATION: (12)..(12)
<223> OTHER INFORMATION: X is D, G, E, A, V, L, or I
<220> FEATURE:
<221> NAME/KEY: VARIANT
<222> LOCATION: (13)..(13)
<223> OTHER INFORMATION: X is L, F, W, G, A, V, L, or I
<220> FEATURE:
<221> NAME/KEY: VARIANT
<222> LOCATION: (22)..(22)
<223> OTHER INFORMATION: X is K, R, D, E, N, or Q

<400> SEQUENCE: 50

Glu Val Xaa Leu Gln Ala Ser Gly Gly Gly Phe Xaa Xaa Pro Gly Gly
1               5                   10                  15

Ser Leu Arg Leu Ser Xaa Ala Ala Ser Gly
          20                25

<210> SEQ ID NO 51
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (4)..(4)
<223> OTHER INFORMATION: X is V, P, G, A, L, I, or M
<220> FEATURE:
<221> NAME/KEY: VARIANT
<222> LOCATION: (7)..(7)
<223> OTHER INFORMATION: X is T, A, S, G, V, L, or I
<220> FEATURE:
<221> NAME/KEY: VARIANT
<222> LOCATION: (9)..(9)
<223> OTHER INFORMATION: X is E, G, D, A, V, L, or I

<400> SEQUENCE: 51

Met Gly Trp Xaa Arg Gln Xaa Pro Xaa Lys Glu Arg Glu Phe Val Ser
1                5                10                15

Ala Ile Ser

<210> SEQ ID NO 52
<211> LENGTH: 39
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (3)..(3)
<223> OTHER INFORMATION: X is P, A, M, G, V, L, or I
<220> FEATURE:
<221> NAME/KEY: VARIANT
<222> LOCATION: (5)..(5)
<223> OTHER INFORMATION: X is T or S
<220> FEATURE:
<221> NAME/KEY: VARIANT
<222> LOCATION: (17)..(17)
<223> OTHER INFORMATION: X is A, S, M, G, V, L, or I
<220> FEATURE:
<221> NAME/KEY: VARIANT
<222> LOCATION: (21)..(21)
<223> OTHER INFORMATION: X is L, V, G, A, or I
<220> FEATURE:
<221> NAME/KEY: VARIANT
<222> LOCATION: (26)..(26)
<223> OTHER INFORMATION: X is S, N, Q, or T
<220> FEATURE:
<221> NAME/KEY: VARIANT
<222> LOCATION: (29)..(29)
<223> OTHER INFORMATION: X is K, R, D, or E
<220> FEATURE:
<221> NAME/KEY: VARIANT
<222> LOCATION: (30)..(30)
<223> OTHER INFORMATION: X is S, A, T, G, V, L, or I
<220> FEATURE:
<221> NAME/KEY: VARIANT
<222> LOCATION: (35)..(35)
<223> OTHER INFORMATION: X is M, T, V, L, or I
<220> FEATURE:
<221> NAME/KEY: VARIANT
<222> LOCATION: (39)..(39)
<223> OTHER INFORMATION: X is V, G, L, I, or A

<400> SEQUENCE: 52

Tyr Tyr Xaa Asp Xaa Val Lys Gly Arg Phe Thr Ile Ser Arg Asp Asn
1                5                10                15

-continued

```
Xaa Lys Asn Thr Xaa Tyr Leu Gln Met Xaa Ser Leu Xaa Xaa Glu Asp
        20                  25                  30

Thr Ala Xaa Tyr Tyr Cys Xaa
        35
```